US012760078B2

(12) United States Patent
Dotti et al.

(10) Patent No.: US 12,760,078 B2
(45) Date of Patent: Oct. 13, 2026

(54) MODIFIED T CELLS AND METHODS OF PREPARING THE SAME

(71) Applicant: The University of North Carolina at Chapel Hill, Chapel Hill, NC (US)

(72) Inventors: Gianpietro Dotti, Chapel Hill, NC (US); Yang Xu, Shenzhen (CN); Xingcong Ma, Xi'an (CN)

(73) Assignee: The University of North Carolina at Chapel Hill, Chapel Hill, NC (US)

( * ) Notice: Subject to any disclaimer, the term of this patent is extended or adjusted under 35 U.S.C. 154(b) by 1042 days.

(21) Appl. No.: 17/762,360

(22) PCT Filed: Sep. 20, 2020

(86) PCT No.: PCT/US2020/051713
§ 371 (c)(1),
(2) Date: Mar. 21, 2022

(87) PCT Pub. No.: WO2021/055915
PCT Pub. Date: Mar. 25, 2021

(65) Prior Publication Data

US 2023/0127263 A1 Apr. 27, 2023

Related U.S. Application Data

(60) Provisional application No. 62/903,717, filed on Sep. 20, 2019.

(51) Int. Cl.

| | |
|---|---|
| ***A61K 35/17*** | (2025.01) |
| ***A61K 40/11*** | (2025.01) |
| ***A61K 40/31*** | (2025.01) |
| ***A61K 40/32*** | (2025.01) |
| ***A61K 40/42*** | (2025.01) |
| ***A61P 35/00*** | (2006.01) |
| ***C07K 14/54*** | (2006.01) |
| ***C07K 14/715*** | (2006.01) |

(52) U.S. Cl.
CPC .......... *C07K 14/5434* (2013.01); *A61K 40/11* (2025.01); *A61K 40/31* (2025.01); *A61K 40/32* (2025.01); *A61K 40/42* (2025.01); *A61K 40/421* (2025.01); *A61K 40/4258* (2025.01); *A61P 35/00* (2018.01); *C07K 14/7155* (2013.01); *A61K 2239/31* (2023.05); *A61K 2239/38* (2023.05); *A61K 2239/54* (2023.05); *A61K 2239/57* (2023.05)

(58) Field of Classification Search
None
See application file for complete search history.

(56) References Cited

U.S. PATENT DOCUMENTS 8,298,790 B2 * 10/2012 Yun ........................ A61P 43/00 435/456
2017/0283775 A1 10/2017 June

FOREIGN PATENT DOCUMENTS

WO 2007/076933 A1 7/2007
WO WO2019/076489 A1 4/2019

OTHER PUBLICATIONS

Chmielewski et al. (American Association of Cancer Research, Jan. 2011, p. 5697-5706 in IDS on Dec. 12, 2022).*
Parham et al., (Journal of Immunology, p. 5699-5708 in IDS on Dec. 12, 2022).*
Liu et al. (Current Immunology Review, 2005, p. 1-33).*
Kueberuwa, et al., "CD19 CAR T Cells Expressing IL-12 Eradicate Lymphoma in Fully Lymphoreplete Mice through Induction of Host Immunity," Molecular Therapy—Oncolytics, vol. 8, pp. 41-51 (2018).
Yeku, et al., "Armored Car T cells enhance antitumor efficacy and overcome the tumor microenvironment," Scientific Reports, vol. 7, No. 1, (2017).
Chmielewski, et al., "IL-12 Release by Engineered T Cells Expressing Chimeric Antigen Receptors Can Effectively Muster an Antigen-Independent Macrophage Response on Tumor Cells That Have Shut Down Tumor Antigen Expression Elimination of Antigen-Loss Tumor Cells," *Cancer Research,* 71.17:5697-5706, (2011).
Chen, et al., "Eradication of Neuroblastoma by T Cells Redirected with an Optimized GD2-Specific Chimeric Antigen Receptor and Interleukin-15GD2. CAR-Ts-Expressing IL15 Eradicate Neuroblastoma," *Clinical Cancer Research,* 25.9:2915-2924, (2019).
Simmons, et al., "Retroviral Transduction of T cells and T cell precursors." *T-Cell Development,* Humana Press, New York, NY, pp. 99-108, (2016).
Parham, et al., "A receptor for the Heterodimeric Cytokine IL-23 is Composed of IL-12Rβ1 and a Novel Cytokine Receptor Subunit, IL-23R," *The Journal of Immunology,* 168.11:5699-5708, (2002).
Ma, et al., "ED SUM: The Efficacy of Chimeric Antigen Receptor (CAR)-T Cells in Solid Tumor Models is Enhanced by IL23 Engineering.: Interleukin-23 Engineering Improves CAR-T Cell Function in Solid Tumors," *Nature Biotechnology,* 38.4:448 (2020).
Dotti, Gianpietro, NIH Abstract for Grant No. CA193140, funded on Feb. 1, 2016.
International Search Report issued in International Application No. PCT/US2020/051713, dated Feb. 9, 2021.
Costa et al., "Adoptive Immunotherapy of Experimental Autoimmune Encephalomyelitis Via T Cell Delivery of the IL-12 p40 Subunit", Journal of Immunology, vol. 167, No. 4, Aug. 15, 2001, pp. 2379-2387.
Nakajima, et al., "Antigen-specific T cell-mediated gene therapy in collagen-induced arthritis", Journal of Clinical Investigation, vol. 107, No. 10, May 15, 2001, pp. 1293-1301.

* cited by examiner

*Primary Examiner* — Agnieszka Boesen
(74) *Attorney, Agent, or Firm* — Morse, Barnes-Brown & Pendleton, P.C.; Lisa M. Warren, Esq.; Erin E. Bryan, Esq.

(57) ABSTRACT

Disclosed herein are modified T cells comprising an IL12β p40 subunit. Also disclosed herein are methods of increasing T cell proliferation and/or methods of treating cancer by administering the modified T cells comprising an IL12β p40 subunit.

17 Claims, 58 Drawing Sheets

Specification includes a Sequence Listing.

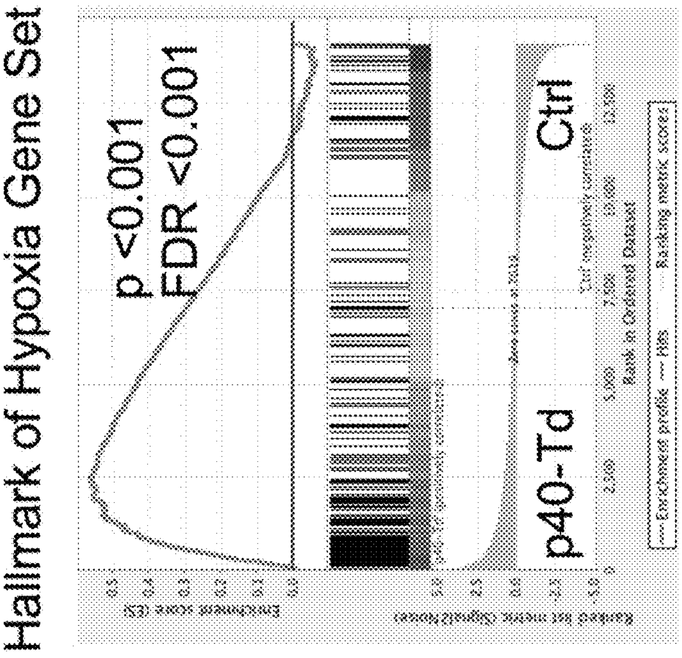
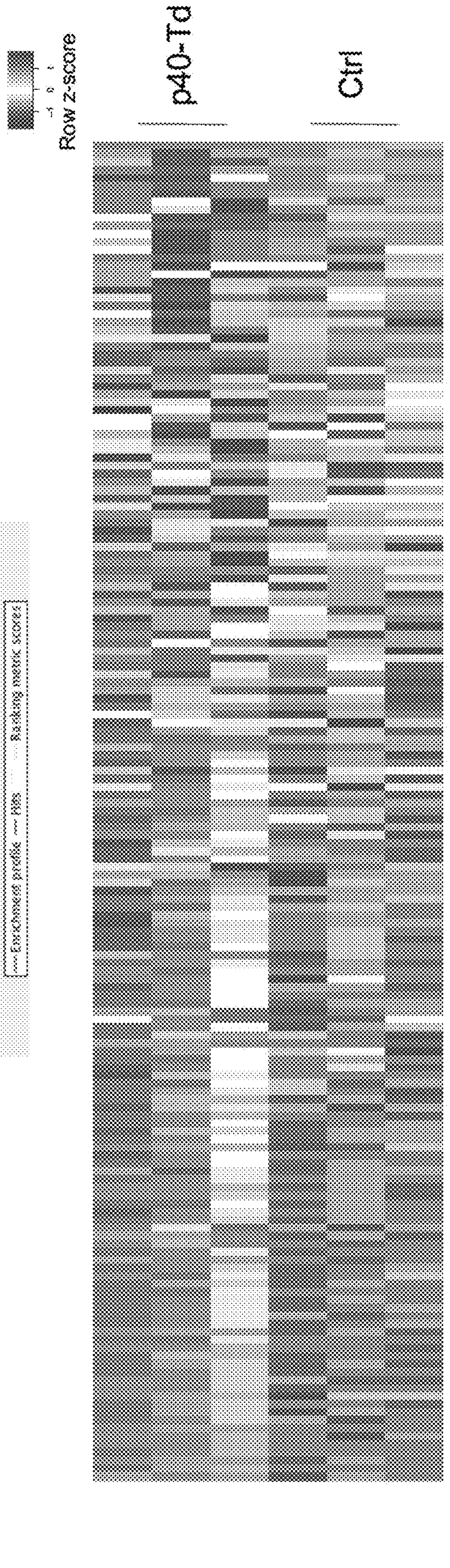
FIG. 2G

MODIFIED T CELLS AND METHODS OF PREPARING THE SAME

RELATED APPLICATIONS

This application is a national stage filing under 35 U.S.C. 371 of International Application No. PCT/US2020/051713, filed Sep. 20, 2020, which claims the benefit of U.S. Provisional Application Ser. No. 62/903,717, filed Sep. 20, 2019, the contents of which is hereby incorporated by reference in its entirety. International Application No. PCT/US2020/051713 was published under PCT Article 21 (2) in English.

GOVERNMENT SUPPORT

This invention was made with government support under Grant Number CA193140 awarded by the National Institutes of Health. The government has certain rights in the invention.

Sequence Listing associated with this application is provided in text format in lieu of a paper copy and is hereby incorporated by reference into the specification. The name of the text file containing the Sequence Listing is UNOC-002-301-ST25.txt. The text file is 6 KB, was created on Dec. 12, 2022, and is being submitted electronically via EFS-Web, concurrent with the filing of the specification.

BACKGROUND OF THE INVENTION

T cells are a main focus for cancer immunotherapies due to their potent anti-tumor activity. While most endogenous T cells in cancer patients are either non-responsive or dysfunctional [1], they can be armed via genetic engineering with a tumor-targeting T cell receptor (TCR) or a chimeric antigen receptor (CAR) [2]. TCR and CAR-engineered T cells promote substantial objective clinical responses in synovial carcinoma [3] and B cell lymphoid malignancies [4], respectively. In particular, CAR-expressing T cells expand in vivo in patients with B cell leukemia and can persist up to 24 months post infusion [5]. In contrast, T cell expansion and persistence within the tumor microenvironment (TME) is usually hindered in solid tumors by multiple factors such as checkpoint inhibition [6] and metabolic starvation [1].

T cell proliferation requires optimal T cell activation, which integrates signals downstream of the T cell receptor (TCR)/CD3 complex, engagement of costimulatory molecules and cytokines [7]. CAR-based engineering provides the first two factors, while TCR-based engineering remains challenging in providing adequate costimulation [7]. However, for both TCR and CAR engineering strategies, the cytokine component remains a significant limiting factor, as the only cytokine secreted by engineered T cells is IL2, which may support the activation and expansion of regulatory T cells (Tregs) [8]. Additional engineering of CAR T cells with common γ chain cytokines such as IL15 is effective in supporting their proliferation and effector function, while the effects on Tregs are limited [9, 10]. However, cytokine engineering can lead to side effects, as they are constitutively produced and their receptor is expressed by most T cells and natural killer (NK) cells, requiring the inclusion of safety switches to contain potential toxic effects [11-13]. Thus, the development of inducible and selective engineering processes supporting T cell expansion and survival within the TME remains critical in adoptive T cell therapies in solid tumors.

SUMMARY OF THE INVENTION

Described herein are novel strategies for incorporating a highly regulated cytokine signaling into tumor-specific T cells to improve their efficacy. This approach has significant translational potential since it can be used for both CAR- and TCR-engineered T cells. IL23 has been identified as having selective proliferative activity in activated T cells when its p40 subunit is engineered in T cells. The proposed manipulated IL23/IL23R axis not only promotes T cell proliferation and anti-tumor activity upon T cell activation, but also limits the effects on bystander cells due to a specific autocrine mode of action.

Disclosed herein are modified T cells comprising an IL12β p40 subunit.

In some embodiments the T cell expresses p40. In some embodiments the T cell exhibits increased cell division. In some embodiments the T cell exhibits reduced apoptosis. In some embodiments the T cell exhibits increased T cell proliferation. In some embodiments the T cell expresses high levels of lytic enzyme granzyme B, as compared to a control cell. In some embodiments the T cell expresses reduced levels of exhaustion markers PD1 and/or CD101, as compared to a control cell. In some embodiments the T cell maintains production of IFNγ and TNFα, as compared to a control cell.

In some embodiments, the T cell, upon activation, produces IL23. In some embodiments the T cell, upon activation, exhibits increased STAT3 phosphorylation. In some embodiments the T cell, upon activation, exhibits differentiation expression of one or more STAT3 regulated genes selected from the group consisting of: SOX2, SOCS3, CEBPD, ABCA1, IFIT1, IFIT3, USP18, CDKN2B, and combinations thereof. In some embodiments the T cell, upon activation, activates the STAT3 pathway.

In some embodiments the T cell promotes enhanced tumor control and improved survival, as compared to a control cell. In some embodiments the T cell exhibits increased anti-tumor activity. Methods for improving or increasing any of the desirable effects on T cells described herein are also encompassed by the invention.

In some embodiments the T cell is a human T cell. In some embodiments the T cell is a non-human T cell. In some embodiments the T cell is a mouse T cell. In some embodiments the T cell is a CAR or TCR-engineered T cell.

In some embodiments the T cell comprising the IL12β p40 subunit is produced by transducing a T cell with a retroviral supernatant comprising an IL12β p40 subunit.

Also disclosed herein are methods of increasing T cell proliferation. The methods comprise modifying a T cell to comprise an IL12β p40 subunit.

Also disclosed herein are methods of treating cancer. The methods comprise administering to a subject a modified T cell comprising an IL12β p40 subunit. In some embodiments upon activation of the modified T cell, the modified T cell produces IL23.

In some embodiments the modified T cell exhibits increased anti-tumor activity. In some embodiments the modified T cell exhibits increased T cell proliferation. In some embodiments the modified T cell promotes tumor regression. In some embodiments the modified T cell protects from tumor re-challenge.

In some embodiments the cancer is a melanoma. In some embodiments the cancer is a pancreatic cancer. In some embodiments the cancer is a hematologic malignancy. In some embodiments the cancer is a multiple myeloma. In some embodiments the cancer is a carcinoma or a sarcoma. In some embodiments the tumor is a solid tumor.

In some embodiments the subject is a mammal (e.g., a human).

BRIEF DESCRIPTION OF THE DRAWINGS

FIGS. 1A-1B show IL23R expression at mRNA (FIG. 1A) and protein level (FIG. 1B) measured by qRT-PCR and western blot, respectively in human T cells activated and expanded ex vivo (ex-$T_M$) at time 0, 24, 48 hours after TCR activation. Data are represented as fold change in expression normalized to the housekeeping gene 18S and to the expression at time 0. Data shown are individual values and mean±SD (n=6 in (a) and n=5 in (b)). FIG. 1**N shows detection of IL23 by ELISA in the supernatant of single cell suspension of paired tumors and adjacent normal tissues. Data are shown as pg of IL23 per 100 μg supernatant protein input (n=6).

FIGS. 2A-2H demonstrate T cell receptor activation induces STAT3 and hypoxia gene signature in p40-Td cells. FIG. 2A provides a volcano plot of gene expression before (left) and 5 days after activation (right) with αCD3 and αCD28 Abs of Ctrl and p40-Td cells. Volcano plot was constructed using $\log_2$fold change and $-\log_{10}$(FDR) of all genes. Red dots represent genes with more than 2-fold change (up or down) and FDR<0.01. FIG. 2B shows number of differentially expressed genes before and after stimulation of Ctrl and p40-Td cells. FIG. 2C provides principal component analysis (PCA) of activated Ctrl and p40-Td cells. FIG. 2D shows GSEA for the expression profiles of the activated Ctrl cells as compared to activated p40-Td cells using "STAT3 upregulated" (up) and "STAT3 downregulated" (down) gene sets and the expression heatmap of genes in the gene sets. FIG. 2E provides representative western blot showing Ser727 and Tyr705 phosphorylation of STAT3 in Ctrl cells and p40-Td cells before and 5 days after stimulation with αCD3 and αCD28 Abs (upper panel). Densitometry of pSTAT3 (lower panel), mean±SD (n=5). *p=0.0001 determined by repeated measured 2-way ANOVA with Sidak post hoc test. FIG. 2F shows qRT-PCR quantification of upregulated (red) or downregulated (down) genes STAT3 pathway related. Data were first normalized to housekeeping gene 18S and the mean±SD $\log_2$fold change of gene expression of activated Ctrl vs. p40-Td cells (n=4) were shown. FIG. 2G shows GSEA for the expression profiles of activated Ctrl and p40-Td cells using "hallmark of hypoxia" gene set (left panel) and expression heatmap of genes in the gene sets (right panel). FIG. 2**H shows qRT-PCR quantification of hypoxia pathway related genes in activated Ctrl and p40-Td cells. Data were first normalized to housekeeping gene 18S and then to the expression level to Ctrl cells (n=4).

FIGS. 3A-3B provide counts of neuroblastoma tumor cells (LAN-1 and CHLA-255) after each round of repetitive coculture (R1, R2 and R3) with either control T cells (Ctrl.), GD2-specific CAR T cells (CAR-Ctrl) or GD2-specific CAR T cells coexpressing p40 (CAR.p40-Td). Data shown as individual values and mean±SD (n=8). **p<0.0001 determined by repeated measure 2-way ANOVA with Sidak post hoc test. FIG. 3O shows representative tumor BLI of 2 independent experiments (n=8 mice/group). FIG. 3P provides kinetics of tumor BLI of 2 independent experiments (n=8 mice/group). Solid lines delineate mean fold change over time, while dashed lines indicate data of each individual mouse.

FIG. 4A provides counts of pancreatic cancer cell (BXPC-3) after each round of repetitive coculture (R1, R2 and R3) with either control T cells (Ctrl.), B7-H3-specific CAR T cells (CAR-Ctrl) or B7-H3-specific CAR T cells coexpressing p40 (CAR.p40-Td) at T cell to tumor cell ratios 1:2 (left panel) or 1:5 (right panel). Data shown as individual values, mean±SD (n=6). *:p=0.0003, **:p<0.0001 determined by repeated measured 2-way ANOVA with Sidak post hoc test. FIG. 4B provides T cell counts after each round of repetitive coculture illustrated in FIG. 4A. Data shown as individual values and mean±SD (n=6). *:p=0.0195 for R2, p=0.021 for R3, :p=0.0024, :p<0.0001 determined by repeated measured 2-way ANOVA with Sidak post hoc test. FIG. 4C provides a schematic of the orthotopic pancreatic cancer model. FIG. 4D shows representative tumor BLI of 2 independent experiments (n=8 mice/group). FIG. 4E provides kinetics of tumor BLI of 2 independent experiments (n=8 mice/group). Solid lines delineate mean fold change over time, while dashed lines indicate data of each individual mouse. FIG. 4F provides Kaplan-Meier survival analysis of 2 independent experiments (n=8 mice/group. FIG. 4G shows frequency of human $CD3^+CD45^+$ cells in blood, spleen and pancreas collected from mice at day 60 post T cell infusion. Data shown as individual values, mean±SD (n=7 mice/group :p=0.0017 for blood, p=0.00065 for spleen and p=0.0014 for tumor) determined by unpaired Student t-test.

FIGS. 5A-5B shows expression of IL23A, IL12B (FIG. 5A) and IL23R (FIG. 5B) genes determined by qRT-PCR in ex vivo activated and expanded murine splenic T cells after re-stimulation with αCD3 and αCD28 Abs for 0, 24 and 48 hours. Data shown as fold change in gene expression normalized to the housekeeping gene CD3E and to the value at time 0. Data shown are individual values and mean±SD (n=4). FIG. 5C provides measurement of murine IL23 released by murine splenic T cells transduced either with the empty vector (EV) or the vector encoding murine IL12B gene (mp40-Td) and re-stimulated with αCD3 and αCD28 Abs for 0, 24 and 48 hours. Data shown are individual values and mean±SD (n=8). FIG. 5D provides cell counts of EV and mp40-Td murine T cells at day 1, 3 and 5 after re-stimulation with αCD3 and αCD28 Abs. Data shown are mean±SD (n=3). ****:p<0.0001 determined by repeated measured 2-way ANOVA with Sidak post hoc test. FIG. 5E provides a schematic of the syngeneic B16 melanoma model. FIG. 5F provides measurement of the tumor volume post T cell injection. Data shown as mean±SD of 2 independent experiments (n=7/8 mice/group) for $1\times10^6$ T cell group and of 1 experiment (n=3/4 mice/group) for $1\times10^6$ T cell group. *:p=0.0182; *:p=0.0007; :p<0.0001 determined by 2-way ANOVA with Sidak post hoc test. FIG. 5G shows detection of murine IL23 in the serum and tumor supernatant collected 14 days after T cell infusion. FIG. 5H shows frequency of OT1 $TCR^+$ ($Va2^+Vb5^+$) cells within the $CD8^+$ T cells in the tissues collected from treated mice. Data shown as mean±SD (n=5 mice/group). p<0.0001 determined by 2-way ANOVA with Sidak post hoc test. FIG. 5I shows immune composition of the peripheral blood, spleen, draining lymph nodes (dLN) and tumor at the time of euthanasia. Data shown as individual values and mean±SD of 2 independent experiments (n=9 mice/group). FIG. 5J provides a schematic of the syngeneic PDAC orthotopic model. Murine cell line KPC-4662 engineered to express murine B7-H3 (KPC-mB7-H3) was implanted ($0.1\times10^6$ cells/mouse) into the pancreas of 6 week old C57BL/6 mice. Eighteen days post tumor cell implantation, mice were irradiated with 400 cGy and 3 days later infused i.v. with syngeneic B7-H3.CAR.EV cells ($1\times10^7$ cells/mouse) or B7-H3.CAR.mp40-Td cells ($1\times10^7$ cells/mouse). Tumor growth was monitored by US. FIG. 5K provides a summary of the fold change (compared to day 0) in tumor volume (n=5 mice/group). p=0.0068 determined by 2-way ANOVA with Sidak post hoc test between B7-H3.CAR.EV vs B7.H3.CAR.mp40-Td at Day 42.

FIG. 6A provides schematics of the co-activation experiment with p40-Td cells and ΔCD19-Td cells. FIG. 6B provides a representative plot of $NGFR^+$ (p40-Td cells) and $CD19^+$ (bystander cells) at days 0 and 5 post-activation. FIG. 6C shows cell number and percentage of $NGFR^+$ and $CD19^+$ cells 5 days post-activation. Data shown as individual values and mean±SD (n=5). Dotted line indicates starting cell number and percentage, respectively. **p<0.0001 determined by paired Student t test. FIG. 6D provides representative western blot showing the expression of IL23R in ΔCD19-Td and p40-Td cells at days 1 or 3 after activation (n=5). FIG. 6E provides a schematic of the sequential coculture of GD2-specific CAR T cells coexpressing either ACD19 (CAR.ACD19-Td) or p40 (CAR.p40-Td) with the LAN-1 tumor cell line. FIG. 6F shows percentages of $NGFR^+$ and $CD19^+$ CAR T cells detected at the end of the first (R1) and second (R2) round of coculture. Data shown as individuals and mean±SD (n=6). :p<0.0001 determined by repeated measured 2-way ANOVA with Sidak post hoc test. FIG. 6G provides a flow plot illustrating the coexpression of NGFR and GFP (left panel) and detection of IL23 in the supernatant (right panel) of T cells transduced with a vector encoding the p40-GFP fusion protein. Data shown as mean±SD (n=4). FIG. 6H provides a schematic and staining procedure of the co-activation experiment with p40-GFP and ACD19-Td cells. FIG. 6I provides representative flow histograms showing the surface binding of the p40-GFP protein on $CD19^+$ or $NGFR^+$ T cells. Individual values and mean±SD (n=5). *p=0.0003 determined by paired Student t test. FIG. 6J provides representative confocal microscopy imaging (left panel) showing the surface binding of p40-GFP protein in $CD19^+$ or $NGFR^+$ cells and quantification of fluorescence intensity of the surface GFP signal for >50 $CD19^+$ or $NGFR^+$ cells (left panels) (n=5). FIGS. 6K-6L show surface binding of p40-GFP in p40-GFP-Td in the absence or presence of the soluble recombinant human IL23R (hIL23R) determined by flow cytometry (FIG. 6K) and confocal microscopy (FIG. 6L). Data are presented as individual values and mean±SD of >50 analyzed cell images (n=5). FIG. 6M shows T cell numbers of Ctrl cells or p40-Td cells at day 5 post-activation with αCD3/αCD28 Abs in the absence or in the presence of soluble rhIL23R. Data are presented as individual values and mean±SD (n=6). ***p=0.0006 determined by repeated measure 2-way ANOVA with Sidak post hoc test.

FIG. 7A provides a schematic representation of the retroviral vectors (upper panel) and representative flow cytometry plots illustrating the transduction efficiency on T cells measured by DNGFR expression and qRT-PCR. Data shown as representative data and mean±SD (n=4). FIG. 7B shows cell counts of Ctrl or p40-Td cells cultured with IL-7 and IL-15. $DNGFR^+$ cells were sorted on day 5 post-transduction. Data shown as mean±SD (n=4). FIG. 7C shows frequency of $CD4^+$ and $CD8^+$ T cells of Ctrl and p40-Td cells at day 12 post-transduction. Data shown as representative data and mean±SD (n=4). FIG. 7D provides representative flow cytometry plots illustrating the expression of memory markers in Ctrl and p40-Td cells at day 12 post-transduction (n=4). FIG. 7E shows mean fluorescence intensity (MFI) of exhaustion and inhibitory receptors in Ctrl and p40-Td cells at day 12 post-transduction. Data shown as mean±SD (n=4).

FIG. 8A shows expression of $Ki67^+$ cells in $CD4^+$ and $CD8^+$ T cells of Ctrl or p40-Td cells stimulated with αCD3 and αCD28 Abs for 3 days. Data shown as individual value, mean±SD (n=5). p value determined by repeated measure 2-way ANOVA with Sidak post hoc test. p=0.0051 for $CD4^+$ and p=0.0038 for $CD8^+$ T cells. FIG. 8B provides expansion index of CellTrace Violet labeled Ctrl or p40-Td cells stimulated with αCD3 and αCD28 Abs for 5 days. Data shown as individual value, mean±SD (n=3). p value determined by repeated measure 2-way ANOVA with Sidak post hoc test. p=0.0056 for $CD4^+$ and p=0.0014 for $CD8^+$ T cells. FIG. 8C provides representative flow plots (left panel) and summary (right panel) of Annexin V and 7AAD staining of Ctrl or p40-Td cells stimulated with αCD3 and αCD28 Abs for 5 days. Data shown as individual value, mean±SD (n=4). p value determined by repeated measure 2-way ANOVA with Sidak post hoc test. p<0.0001 for live, ns for early apoptotic and p<0.0001 for late apoptotic.

FIG. 9A provides representative flow plots (left panel) and summary (right panel) illustrating the co-expression of CAR and ΔNGFR in Ctrl and GD2-specific CAR-Ts expressing p40. Data shown individual values, mean±SD (n=4). FIG. 9B provides T cell counts of GD2-specific CAR.Ctrl cells or CAR.p40-Td cells activated by plate-bound anti-idiotype 1A7 Ab. Data shown as mean±SD (n=5). **p<0.0001 determined by repeated measure 2-way ANOVA with Sidak post hoc test. FIG. 9C shows frequency of apoptotic cells in CAR.Ctrl cells and CAR.p40-Td cells activated by the 1A7 Ab for 5 days using the Annexin V/7AAD staining. Data shown as individual values and mean±SD (n=4). *p=0.0006 for live cells; *p=0.0005 for late apoptotic cells. p values were determined by repeated measure 2-way ANOVA with Sidak post hoc test. FIG. 9D shows detection of IL23 and IL2 in the supernatant of CAR.Ctrl cells and CAR.p40-Td cells post-stimulation with the 1A7 Ab stimulation. Data shown as individual values and mean±SD (n=3). FIG. 9**E provides a schematic of the repetitive coculture experiment.

DETAILED DESCRIPTION OF THE INVENTION

Figure 1B:
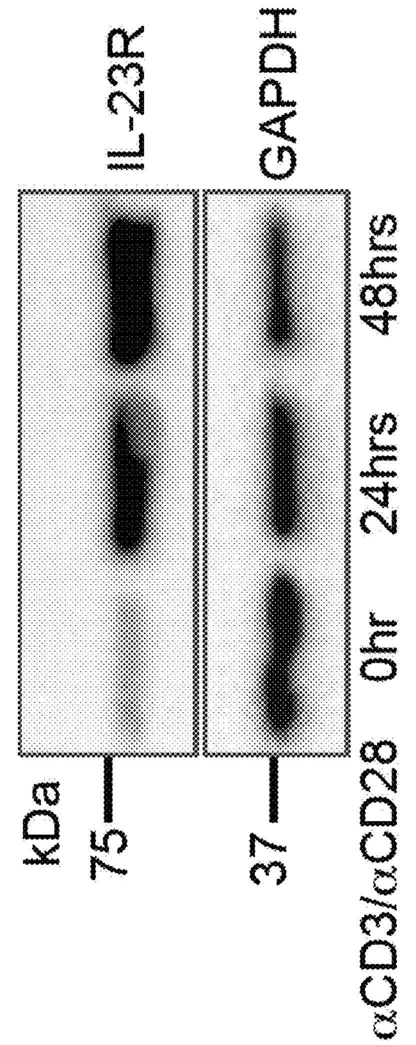

One of the benefits of adoptive T cell immunotherapies for cancer is the ability of the infused T cells to proliferate upon tumor engagement and establish immunological memory to prevent tumor relapse. However, both T cell proliferation and effector function are hampered by immunosuppressive factors within the tumor microenvironment (TME). Proliferative cytokines (e.g., IL2 and IL15) support T cell division and anti-tumor activity, but the incorporation of cytokines into tumor specific T cells comes with various risks due to the constitutive cytokine signaling in T cells and activation of bystander cells that may further increase toxicity or reduce efficacy. IL23 is described herein as having a selective proliferative activity in activated T cells when its p40 subunit is engineered in T cells. The proposed manipulated IL23/IL23R axis not only promotes T cell proliferation and anti-tumor activity upon T cell activation, but also limits the effects on bystander cells due to a specific autocrine mode of action.

Described herein are modified T cells, compositions comprising the modified T cells, and therapeutic methods using the modified T cells. The modified T cells described herein exhibit enhanced anti-tumor activity, including enhanced proliferation.

Modified T Cells

Aspects of the disclosure relate to modified T cells. In some embodiments, the modified T cells are tumor specific T cells that comprise an IL23α p19 subunit and an IL12β p40 subunit. In some embodiments, the modified T cell is a chimeric antigen receptor (CAR)-engineered T cell. In some embodiments, the modified T cell is a T-cell receptor (TCR)-engineered T cell. In some aspects, the modified T cells express p40. In some embodiments, a modified T cell produces IL23 upon activation (e.g., TCR or CAR activation). It is generally understood that both IL23α p19 subunit and IL12β p40 subunit must be present for the T cell to produce and release IL23. In some embodiments, the production of IL23 has been shown to drive T cell proliferation and survival.

In some embodiments, the T cell is a human T cell or a non-human T cell. In some embodiments mammalian cells are used. In some embodiments mammalian cells are primate cells (human cells or non-human primate cells), rodent (e.g., mouse, rat, rabbit, hamster) cells, canine, feline, bovine, or other mammalian cells. In some embodiments avian cells are used. In some embodiments, the T cells are tumor-specific T cells.

In some embodiments, the T cell is a αβT cell, a cytotoxic T lymphocyte (CTL), a regulatory T cell, a natural killer T (NKT) cell, a Th17 cell, a γδT cell, or any combination thereof. In some embodiments, the T cell is an autologous cell. In some embodiments, the T cell is not an autologous cell. In some embodiments, the T cell is of the same species of a subject. In some embodiments, the T cell is of a species that is different than the species of a subject.

In certain embodiments a modified T cell is engineered to comprise both an IL23α p19 subunit and an IL12β p40 subunit that, upon activation, produces IL23. In some aspects the modified T cell further includes part or all of a cytoplasmic signaling domain of CD3ζ chain, and/or part or all of one or more costimulatory molecules, such as CD28, 41BB, and OX40. In some aspects the modified T cell further includes a cytoplasmic signaling domain of CD3ζ chain. In some aspects the modified T cell further includes a portion of a cytoplasmic signaling domain of CD3ζ chain. In some aspects the modified T cell further includes a costimulatory molecule selected from the group consisting of CD28, 41BB, OX40, and combinations thereof. In some aspects the modified T cell further includes a portion of a costimulatory molecule selected from the group consisting of CD28, 41BB, OX40, and combinations thereof.

The modified T cells described herein exhibit one or more features. Nonlimiting examples of the features of the modified T cells include increased cell division, reduced apoptosis, increased T cell proliferation, increased STAT3 phosphorylation (upon activation), exhibits differentiation expression of one or more STAT3 regulated genes (e.g., SOX2, SOCS3, CEBPD, ABCA1, IFIT1, IFIT3, USP18, CDKN2B, and combinations thereof), activates the STAT3 pathway (upon activation), expresses high levels of lytic enzyme granzyme B (as compared to a control cell), expresses reduced levels of exhaustion markers PD1 and/or CD101 (as compared to a control cell), maintains production of IFNγ and TNFα (as compared to a control cell), promotes enhanced tumor control and improved survival (as compared to a control cell), exhibits increased anti-tumor activity, and combinations thereof. In some embodiments, the modified T cell exhibits increased cell division. In some embodiments, the modified T cell exhibits reduced apoptosis. In some embodiments, the modified T cell exhibits increased T cell proliferation. In some embodiments, the modified T cell, upon activation, exhibits increased STAT3 phosphorylation. In some embodiments, the modified T cell exhibits differentiation expression of one or more STAT3 regulated genes selected from the group consisting of: SOX2, SOCS3, CEBPD, ABCA1, IFIT1, IFIT3, USP18, CDKN2B, and combinations thereof. In some embodiments, the modified T cell, upon activation, activates the STAT3 pathway. In some embodiments, the modified T cell expresses high levels of lytic enzyme granzyme B, as compared to a control cell. In some embodiments, the modified T cell expresses reduced levels of exhaustion markers PD1 and/or CD101, as compared to a control cell. In some embodiments, the modified T cell maintains production of IFNγ and TNFα, as compared to a control cell. In some embodiments, the modified T cell promotes enhanced tumor control and improved survival, as compared to a control cell. In some embodiments, the modified T cell exhibits increased anti-tumor activity.

In some embodiments T cells are isolated from a mammal and genetically modified (i.e., transduced or transfected in vitro) with the IL12β p40 subunit. In some embodiments, a T cell can be transduced with a viral vector or transfected with a plasmid or nucleic acid construct. In some embodiments, the modified T cell is a tumor specific T cell that is transduced with a retroviral supernatant comprising an IL12β p40 subunit. In some embodiments, an IL12β p40 subunit is supplemented to a T cell using gamma retroviral transduction. In some aspects, the modified T cells are activated in response to TCR or CAR stimulation.

For administration to a subject, modified T cells produced by the methods as disclosed herein can be administered to a subject, for example in pharmaceutically acceptable compositions. These pharmaceutically acceptable compositions comprise a therapeutically-effective amount of modified T cells as described above, formulated together with one or more pharmaceutically acceptable carriers (additives) and/or diluents. In some embodiments the pharmaceutical compositions comprising the modified T cells further include diluents and/or other components, such as IL2, and/or other cytokines and/or cell populations.

As described herein, the pharmaceutical compositions of the present invention can be specially formulated for administration in solid or liquid form, including those adapted for the following: (1) oral administration, for example, drenches (aqueous or non-aqueous solutions or suspensions), lozenges, dragees, capsules, pills, tablets (e.g., those targeted for buccal, sublingual, and systemic absorption), boluses, powders, granules, pastes for application to the tongue; (2) parenteral administration, for example, by subcutaneous, intramuscular, intravenous or epidural injection as, for example, a sterile solution or suspension, or sustained-release formulation; (3) topical application, for example, as a cream, ointment, or a controlled-release patch or spray applied to the skin; (4) intravaginally or intrarectally, for example, as a pessary, cream or foam; (5) sublingually; (6) ocularly; (7) transdermally; (8) transmucosally; or (9) nasally. Additionally, compounds can be implanted into a patient or injected using a drug delivery system. See, for example, Urquhart, et al., Ann. Rev. Pharmacol. Toxicol. 24: 199-236 (1984); Lewis, ed. "Controlled Release of Pesticides and Pharmaceuticals" (Plenum Press, New York, 1981); U.S. Pat. No. 3,773,919; and U.S. Pat. No. 35 3,270,960. In some embodiments direct administration to a tumor and/or a body cavity, orifice, and/or tissue containing a tumor may be desired.

As used here, the term "pharmaceutically acceptable" refers to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

As used here, the term "pharmaceutically-acceptable carrier" means a pharmaceutically-acceptable material, composition or vehicle, such as a liquid or solid filler, diluent, excipient, manufacturing aid (e.g., lubricant, talc magnesium, calcium or zinc stearate, or steric acid), or solvent encapsulating material, involved in carrying or transporting the subject compound from one organ, or portion of the body, to another organ, or portion of the body. Each carrier must be "acceptable" in the sense of being compatible with the other ingredients of the formulation and not injurious to the patient. Some examples of materials which can serve as pharmaceutically-acceptable carriers include: (1) sugars, such as lactose, glucose and sucrose; (2) starches, such as corn starch and potato starch; (3) cellulose, and its derivatives, such as sodium carboxymethyl cellulose, methylcellulose, ethyl cellulose, microcrystalline cellulose and cellulose acetate; (4) powdered tragacanth; (5) malt; (6) gelatin; (7) lubricating agents, such as magnesium stearate, sodium lauryl sulfate and talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol (PEG); (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) pH buffered solutions; (21) polyesters, polycarbonates and/or polyanhydrides; (22) bulking agents, such as polypeptides and amino acids (23) serum component, such as serum albumin, HDL and LDL; (22) $C_2$-$C_{12}$ alcohols, such as ethanol; and (23) other non-toxic compatible substances employed in pharmaceutical formulations. Wetting agents, coloring agents, release agents, coating agents, sweetening agents, flavoring agents, perfuming agents, preservative and antioxidants can also be present in the formulation. The terms such as "excipient", "carrier", "pharmaceutically acceptable carrier" or the like are used interchangeably herein.

Methods of Treatment

Disclosed herein are methods of increasing T cell proliferation. In some embodiments, the method includes modifying a T cell to comprise an IL12β p40 subunit.

Also disclosed herein are methods of treating or preventing a cancer in a subject in need thereof. In some embodiments the method includes administering a modified T cell comprising an IL12β p40 subunit, as described herein. In some embodiments the method including administering a therapeutically effective amount of modified T cells comprising an IL12β p40 subunit.

Also disclosed herein are methods of generating a population of modified T cells in a subject (e.g., a subject diagnosed with cancer and/or otherwise in need thereof). In some embodiments, the method includes administering to a subject a T cell modified to comprise an IL12β p40 subunit. In some aspects, the population of modified T cells persists in the subject for a period of time following administration to the subject (e.g., at least one week, one month, two months, three months, four months, five months, six months, nine months, one year, two years, five years, etc.).

Further disclosed herein are methods of expanding a population of modified T cells in a subject (e.g., a subject diagnosed with cancer and/or a subject in need thereof). In some embodiments, the method includes administering to the subject a T cell modified to comprise an IL12β p40 subunit, where the administered modified T cell produces a population of progeny cells in the subject.

In some embodiment, the cells described herein, e.g. modified T cells are transplantable, e.g., modified T cells can be administered to a subject. In some embodiments, the subject who is administered modified T cells is the same subject from whom the pre-modified T cells was obtained (e.g. for autologous cell therapy). In some embodiments, the subject is a different subject. In some embodiments, a subject is suffering from cancer, or is a normal subject. For example, the modified T cells for transplantation can be a form suitable for transplantation.

The method can further include administering the modified T cells to a subject in need thereof, e.g., a mammalian subject, e.g., a human subject. The source of the cells can be a mammal, preferably a human. The source or recipient of the cells can also be a non-human subject, e.g., an animal model. The term "mammal" includes organisms, which include mice, rats, cows, sheep, pigs, rabbits, goats, horses, monkeys, dogs, cats, and preferably humans. Likewise, transplantable cells can be obtained from any of these organisms, including a non-human transgenic organism.

A composition comprising modified T cells can be administered to a subject using an implantable device. Implantable devices and related technology are known in the art and are useful as delivery systems where a continuous, or timed-release delivery of compounds or compositions delineated herein is desired. Additionally, the implantable device delivery system is useful for targeting specific points of compound or composition delivery (e.g., localized sites, organs). Negrin et al., Biomaterials, 22(6):563 (2001). Timed-release technology involving alternate delivery methods can also be used in this invention. For example, timed-release formulations based on polymer technologies, sustained-release techniques and encapsulation techniques (e.g., polymeric, liposomal) can also be used for delivery of the compounds and compositions delineated herein.

As used herein, the term "administer" refers to the placement of a composition into a subject by a method or route which results in at least partial localization of the composition at a desired site such that desired effect is produced. Routes of administration suitable for the methods of the invention include both local and systemic administration. Generally, local administration results in more of the administered modified T cells being delivered to a specific location as compared to the entire body of the subject, whereas, systemic administration results in delivery of the modified T cells to essentially the entire body of the subject.

In the context of administering modified T cells, the term "administering" also include transplantation of such cells in a subject. As used herein, the term "transplantation" refers to the process of implanting or transferring at least one cell to a subject. The term "transplantation" includes, e.g., autotransplantation (removal and transfer of cell(s) from one location on a patient to the same or another location on the same patient), allotransplantation (transplantation between members of the same species), and xenotransplantation (transplantations between members of different species). A skilled artisan is well aware of methods for implanting or transplantation of cells for treating cancer, which are amenable to the present invention.

Modified T cells or compositions comprising the same can be administered by any appropriate route known in the art including, but not limited to, oral or parenteral routes, including intravenous, intramuscular, subcutaneous, transdermal, airway (aerosol), pulmonary, nasal, rectal, and topical (including buccal and sublingual) administration.

Exemplary modes of administration include, but are not limited to, injection, infusion, instillation, inhalation, or ingestion. "Injection" includes, without limitation, intravenous, intramuscular, intraarterial, intrathecal, intraventricular, intracapsular, intraorbital, intracardiac, intradermal, intraperitoneal, transtracheal, subcutaneous, subcuticular, intraarticular, sub capsular, subarachnoid, intraspinal, intracerebro spinal, and intrasternal injection and infusion. In preferred embodiments, the compositions are administered by intravenous infusion or injection.

As used herein, a "subject" means a human or animal. Usually the animal is a vertebrate such as a primate, rodent, domestic animal or game animal. Primates include chimpanzees, cynomologous monkeys, spider monkeys, and macaques, e.g., Rhesus. Rodents include mice, rats, woodchucks, ferrets, rabbits and hamsters. Domestic and game animals include cows, horses, pigs, deer, bison, buffalo, feline species, e.g., domestic cat, canine species, e.g., dog, fox, wolf, avian species, e.g., chicken, emu, ostrich, and fish, e.g., trout, catfish and salmon. Patient or subject includes any subset of the foregoing, e.g., all of the above, but excluding one or more groups or species such as humans, primates or rodents. In certain embodiments of the aspects described herein, the subject is a mammal, e.g., a primate, e.g., a human. The terms, "patient" and "subject" are used interchangeably herein. The terms, "patient" and "subject" are used interchangeably herein. A subject can be male or female.

Preferably, the subject is a mammal. The mammal can be a human, non-human primate, mouse, rat, dog, cat, horse, or cow, but are not limited to these examples. In addition, the methods and compositions described herein can be used to treat domesticated animals and/or pets.

In some embodiments a subject is deemed "at risk" of having or developing cancer or recurrence of cancer. Whether a subject is at risk of having or developing cancer or having a recurrence of cancer is a determination that may be within the discretion of the skilled practitioner caring for the subject. Any suitable diagnostic test and/or criteria can be used. For example, a subject may be considered "at risk" of having or developing cancer if (i) the subject has a mutation, genetic polymorphism, gene or protein expression profile, and/or presence of particular substances in the blood, associated with increased risk of developing or having cancer relative to other members of the general population not having mutation or genetic polymorphism; (ii) the subject has one or more risk factors such as having a family history of cancer, having been exposed to a carcinogen or tumor-promoting agent or condition, e.g., asbestos, tobacco smoke, aflatoxin, radiation, chronic infection/inflammation, etc., advanced age; (iii) the subject has one or more symptoms of cancer, (iv) the subject has a medical condition that is known to increase the likelihood of cancer, etc.

As used herein, the type of cancer is not limited. The term "cancer" as used herein is defined as a hyperproliferation of cells whose unique trait—loss of normal controls—results in unregulated growth, lack of differentiation, local tissue invasion, and metastasis. With respect to the inventive methods, the cancer can be any cancer, including any of acute lymphocytic cancer, acute myeloid leukemia, adenocarcinoma, alveolar rhabdomyosarcoma, anal cancer, angiosarcoma, B cell lymphoma, basal cell carcinoma, bladder cancer, bone cancer, brain cancer, breast cancer, cancer of the anus, anal canal, or anorectum, cancer of the eye, cancer of the intrahepatic bile duct, cancer of the joints, cancer of the neck, gallbladder, or pleura, cancer of the nose, nasal cavity, or middle ear, cancer of the oral cavity, cancer of the vulva, chronic lymphocytic leukemia, chronic myeloid cancer, colon cancer, colorectal cancer, esophageal cancer, cervical cancer, endometrial cancer, fibrosarcoma, gastrointestinal carcinoid tumor, hematopoietic neoplasias, Hodgkin lymphoma, hypopharynx cancer, kidney cancer, larynx cancer, leukemia, liquid tumors, liver cancer, lung cancer, lymphoma, malignant mesothelioma, mastocytoma, melanoma, multiple myeloma, myeloma, nasopharynx cancer, non-Hodgkin lymphoma, ovarian cancer, pancreatic cancer, peritoneum, omentum, and mesentery cancer, pharynx cancer, prostate cancer, rectal cancer, renal cancer, sarcoma, skin cancer, small intestine cancer, soft tissue cancer, solid tumors, squamous cell carcinoma, stomach cancer, T cell lymphoma, testicular cancer, thymoma, thyroid cancer, ureter cancer, urinary bladder cancer, and uterine cancer. As used herein, the term "tumor" refers to an abnormal growth of cells or tissues of the malignant type, unless otherwise specifically indicated and does not include a benign type tissue.

As used herein, the term "treating" and "treatment" refers to administering to a subject an effective amount of modified T cells altered ex vivo according to the methods described herein so that the subject has a reduction in at least one symptom of the disease or an improvement in the disease, for example, beneficial or desired clinical results. For purposes of this invention, beneficial or desired clinical results include, but are not limited to, alleviation of one or more symptoms, diminishment of extent of disease, stabilized (i.e., not worsening) state of disease, delay or slowing of disease progression, amelioration or palliation of the disease state, and remission (whether partial or total), whether detectable or undetectable. Treating can refer to prolonging survival as compared to expected survival if not receiving treatment. Thus, one of skill in the art realizes that a treatment may improve the disease condition, but may not be a complete cure for the disease. As used herein, the term "treatment" includes prophylaxis. Alternatively, treatment is "effective" if the progression of a disease is reduced or halted. "Treatment" can also mean prolonging survival as compared to expected survival if not receiving treatment. Those in need of treatment include those already diagnosed with a disorder associated with expression of a polynucleotide sequence, as well as those likely to develop such a disorder due to genetic susceptibility or other factors.

By "treatment," "prevention" or "amelioration" of a disease or disorder is meant delaying or preventing the onset of such a disease or disorder, reversing, alleviating, ameliorating, inhibiting, slowing down or stopping the progression, aggravation or deterioration the progression or severity of a condition associated with such a disease or disorder. In one embodiment, the symptoms of a disease or disorder are alleviated by at least 5%, at least 10%, at least 20%, at least 30%, at least 40%, or at least 50%.

The dosage, administration schedule and method of administering the modified T cells are not limited. The dosage will depend upon a variety of factors including other treatment, the number of doses and the individual patient parameters including age, physical condition, size and weight. These are factors well known to those of ordinary skill in the art and can be addressed with no more than routine experimentation. In some embodiments, a maximum tolerated dose may be used, that is, the highest safe and tolerable dose according to sound medical judgment. In some embodiments, a pharmaceutical composition comprising the modified T cells can be administered at a dosage of about $10^3$ to about $10^{10}$ cells/kg body weight, and in some embodiments, the dosage can be from about $10^5$ to about $10^6$ cells/kg body weight, including all integer values (e.g., $10^4$, $10^5$, $10^6$, $10^7$, $10^8$, $10^9$) within those ranges.

The dose used may be the maximal tolerated dose or a sub-therapeutic dose or any dose therebetween. In some embodiments modified T cells are administered in combination with one or more agents. In some embodiments, the modified T cells and/or the one or more agents are administered according to a defined administration schedule. Multiple doses are contemplated. In some embodiments, when the modified T cells and one or more agents are administered in combination, a sub-therapeutic dosage of one or more of the agents may be used. A "sub-therapeutic dose" as used herein refers to a dosage which is less than that dosage which would produce a therapeutic result in the subject if administered in the absence of the other agent. In some aspects, a sub-therapeutic dose of an anticancer agent is one which would not produce a useful therapeutic result in the subject in the absence of the administration of the modified T cells described herein. Therapeutic doses of anticancer agents are well known in the field of medicine for the treatment of cancer.

As used herein, pharmaceutical compositions comprise one or more agents or compositions that have therapeutic utility, and a pharmaceutically acceptable carrier, e.g., a carrier that facilitates delivery of agents or compositions. Agents and pharmaceutical compositions disclosed herein may be administered by any suitable means such as orally, intranasally, subcutaneously, intramuscularly, intravenously, intra-arterially, parenterally, intraperitoneally, intrathecally, intratracheally, ocularly, sublingually, vaginally, rectally, dermally, or as an aerosol. Depending upon the type of condition (e.g., cancer) to be treated, compounds of the invention may, for example, be inhaled, ingested or administered by systemic routes. Thus, a variety of administration modes, or routes, are available. The particular mode selected will typically depend on factors such as the particular compound selected, the particular condition being treated and the dosage required for therapeutic efficacy. The methods described herein, generally speaking, may be practiced using any mode of administration that is medically acceptable, meaning any mode that produces acceptable levels of efficacy without causing clinically unacceptable adverse effects. Preferred modes of administration are parenteral and oral routes. The term "parenteral" includes subcutaneous, intravenous, intramuscular, intraperitoneal, and intrasternal injection, or infusion techniques. In some embodiments, inhaled medications are of particular use because of the direct delivery to the lung, for example in lung cancer patients. Several types of metered dose inhalers are regularly used for administration by inhalation. These types of devices include metered dose inhalers (MDI), breath-actuated MDI, dry powder inhaler (DPI), spacer/holding chambers in combination with MDI, and nebulizers. In some embodiments agents are delivered by pulmonary aerosol. Other appropriate routes will be apparent to one of ordinary skill in the art.

Toxicity and therapeutic efficacy of administration of compositions comprising modified T cells can be determined by standard pharmaceutical procedures in cell cultures or experimental animals, e.g., for determining the LD50 (the dose lethal to 50% of the population) and the ED50 (the dose therapeutically effective in 50% of the population). Compositions comprising modified T cells that exhibit large therapeutic indices are preferred.

The amount of a composition comprising modified T cells can be tested using several well-established animal models.

In some embodiments, data obtained from the cell culture assays and in animal studies can be used in formulating a range of dosage for use in humans. The dosage of such compounds lies preferably within a range of circulating concentrations that include the ED50 with little or no toxicity. The dosage may vary within this range depending upon the dosage form employed and the route of administration utilized.

The therapeutically effective dose of a composition comprising modified T cells can also be estimated initially from cell culture assays. Alternatively, the effects of any particular dosage can be monitored by a suitable bioassay.

With respect to duration and frequency of treatment, it is typical for skilled clinicians to monitor subjects in order to determine when the treatment is providing therapeutic benefit, and to determine whether to increase or decrease dosage, increase or decrease administration frequency, discontinue treatment, resume treatment or make other alteration to treatment regimen. The dosing schedule can vary from once a week to daily depending on a number of clinical factors. The desired dose can be administered at one time or divided into subdoses, e.g., 2-4 subdoses and administered over a period of time, e.g., at appropriate intervals through the day or other appropriate schedule. Such sub-doses can be administered as unit dosage forms. In some embodiments, administration is chronic, e.g., one or more doses daily over a period of weeks or months. Examples of dosing schedules are administration daily, twice daily, three times daily or four or more times daily over a period of 1 week, 2 weeks, 3 weeks, 4 weeks, 1 month, 2 months, 3 months, 4 months, 5 months, or 6 months or more.

In another aspect of the invention, the methods provide use of an isolated population of modified T cells. In one embodiment of the invention, an isolated population of modified T cells as disclosed herein may be used for the production of a pharmaceutical composition, for the use in transplantation into subjects in need of treatment, e.g. a subject that has, or is at risk of developing cancer. Examples include subjects with melanoma or pancreatic cancer. In some embodiments, an isolated population of modified T cells as disclosed herein may be autologous and/or allogeneic. In some embodiments, the subject is a mammal, and in other embodiments the mammal is a human.

One embodiment of the invention relates to a method of treating cancer in a subject comprising administering an effective amount of a composition comprising modified T cells as disclosed herein to a subject with cancer. Other embodiments relate to a method of treating a tumor in a subject comprising administering an effective amount of a composition comprising modified T cells as disclosed herein to a subject with a tumor.

In some embodiments, the modified T cells as disclosed herein are administered to a subject having cancer in combination with a second therapeutic treatment (e.g., chemotherapy, radiation, immunosuppressive agents, such as cyclosporin, azathioprine, methotrexate, mycophenolate, and FK506, antibodies, or other immunoablative agents such as CAM PATH, anti-CD3 antibodies or other antibody therapies, cytotoxin, fludaribine, cyclosporin, FK506, rapamycin, mycophenolic acid, steroids, FR901228, cytokines, and/or irradiation).

In some embodiments, the modified T cells are administered to a patient in conjunction with (e.g., before, concurrently and/or following) bone marrow transplantation, T cell ablative therapy using either chemotherapy agents such as fludarabine, external-beam radiation therapy (XRT), cyclophosphamide, or antibodies such as OKT3 or CAMPATH. In another embodiment, the modified T cells are administered following B-cell ablative therapy such as agents that react with CD20, e.g., Rituxan. For example, in one embodiment, subjects may undergo standard treatment with high dose chemotherapy followed by peripheral blood stem cell transplantation. In certain embodiments, following the transplant, subjects can receive an infusion of the expanded modified T cells. In an additional embodiment, expanded cells can be administered before and/or following surgery.

In the treatment of cancers or tumors the modified T cells may optionally be administered in conjunction with other, different, cytotoxic agents such as chemotherapeutic or antineoplastic compounds or radiation therapy useful in the treatment of the disorders or conditions described herein (e.g., chemotherapeutics or antineoplastic compounds). The other compounds may be administered prior to, concurrently and/or after administration of the modified T cells. As used herein, the word "concurrently" means sufficiently close in time to produce a combined effect (that is, concurrently may be simultaneously, or it may be two or more administrations occurring before or after each other)

As used herein, the phrase "radiation therapy" includes, but is not limited to, x-rays or gamma rays which are delivered from either an externally applied source such as a beam or by implantation of small radioactive sources.

Nonlimiting examples of suitable chemotherapeutic agents which may be administered with the modified T cells as described herein include daunomycin, cisplatin, verapamil, cytosine arabinoside, aminopterin, democolcine, tamoxifen, Actinomycin D, Alkylating agents (including, without limitation, nitrogen mustards, ethylenimine derivatives, alkyl sulfonates, nitrosoureas and triazenes): Uracil mustard, Chlormethine, Cyclophosphamide (Cytoxan®), Ifosfamide, Melphalan, Chlorambucil, Pipobroman, Triethylene-melamine, Triethylenethiophosphoramine, Busulfan, Carmustine, Lomustine, Streptozocin, Dacarbazine, and Temozolomide; Antimetabolites (including, without limitation, folic acid antagonists, pyrimidine analogs, purine analogs and adenosine deaminase inhibitors): Methotrexate, 5-Fluorouracil, Floxuridine, Cytarabine, 6-Mercaptopurine, 6-Thioguanine, Fludarabine phosphate, Pentostatine, and Gemcitabine, Natural products and their derivatives (for example, vinca alkaloids, antitumor antibiotics, enzymes, lymphokines and epipodophyllotoxins): Vinblastine, Vincristine, Vindesine, Bleomycin, Dactinomycin, Daunorubicin, Doxorubicin, Epirubicin, Idarubicin, Ara-C, paclitaxel (paclitaxel is commercially available as Taxol®), Mithramycin, Deoxyco-formycin, Mitomycin-C, L-Asparaginase, Interferons (especially IFN-α), Etoposide, and Teniposide; Other anti-proliferative cytotoxic agents are navelbene, CPT-11, anastrazole, letrazole, capecitabine, reloxafine, cyclophosphamide, ifosamide, and droloxafine. Additional anti-proliferative cytotoxic agents include, but are not limited to, melphalan, hexamethyl melamine, thiotepa, cytarabin, idatrexate, trimetrexate, dacarbazine, L-asparaginase, camptothecin, topotecan, bicalutamide, flutamide, leuprolide, pyridobenzoindole derivatives, interferons, and interleukins. Preferred classes of antiproliferative cytotoxic agents are the EGFR inhibitors, Her-2 inhibitors, CDK inhibitors, and Herceptin® (trastuzumab). (see, e.g., U.S. Pat. Nos. 6,537,988; 6,420,377). Such compounds may be given in accordance with techniques currently known for the administration thereof.

In some embodiments, the modified T cells as disclosed herein may be administered in any physiologically acceptable excipient, where the modified T cells may find an appropriate site for replication, proliferation, and/or engraftment. In some embodiments, the modified T cells as disclosed herein can be introduced by injection, catheter, or the like. In some embodiments, the modified T cells as disclosed herein can be frozen at liquid nitrogen temperatures and stored for long periods of time, being capable of use on thawing. If frozen, the modified T cells will usually be stored in a 10% DMSO, 50% FCS, 40% RPMI 1640 medium. Once thawed, the cells may be expanded by use of growth factors and/or feeder cells associated with culturing T cells.

In some embodiments, the modified T cells as disclosed herein can be supplied in the form of a pharmaceutical composition, comprising an isotonic excipient prepared under sufficiently sterile conditions for human administration. For general principles in medicinal formulation, the reader is referred to Cell Therapy: Stem Cell Transplantation, Gene Therapy, and Cellular Immunotherapy, by G. Morstyn & W. Sheridan eds, Cambridge University Press, 1996; and Hematopoietic Stem Cell Therapy, E. D. Ball, J. Lister & P. Law, Churchill Livingstone, 2000. Choice of the cellular excipient and any accompanying elements of the composition comprising the modified T cells as disclosed herein will be adapted in accordance with the route and device used for administration. In some embodiments, a composition comprising the modified T cells can also comprise or be accompanied with one or more other ingredients that facilitate the engraftment or functional mobilization of the modified T cells. Suitable ingredients include matrix proteins that support or promote adhesion of the modified T cells, or complementary cell types. In another embodiment, the composition may comprise resorbable or biodegradable matrix scaffolds.

In some embodiments, the modified T cells can be administered and dosed in accordance with good medical practice, taking into account the clinical condition of the individual patient, the site and method of administration, scheduling of administration, patient age, sex, body weight and other factors known to medical practitioners. The pharmaceutically "effective amount" for purposes herein is thus determined by such considerations as are known in the art. The amount must be effective to achieve improvement, including but not limited to improved survival rate or more rapid recovery, or improvement or elimination of symptoms and other indicators as are selected as appropriate measures by those skilled in the art. Modified T cells can be administered to a subject at the following locations: clinic, clinical office, emergency department, hospital ward, intensive care unit, operating room, catheterization suites, and radiologic suites.

In other embodiments, the modified T cells are stored for later implantation/infusion. The modified T cells may be divided into more than one aliquot or unit such that a portion of the modified T cells are retained for later application while part is applied immediately to the subject. Moderate to long-term storage of all or part of the cells in a cell bank is also within the scope of this invention, as disclosed in U.S. Patent Publication No. 2003/0054331 and Patent Publication No. WO 03/024215, and is incorporated by reference in their entireties. At the end of processing, the concentrated cells may be loaded into a delivery device, such as a syringe, for placement into the recipient by any means known to one of ordinary skill in the art.

Pharmaceutical compositions comprising effective amounts of modified T cells are also contemplated by the present invention. These compositions comprise an effective number of modified T cells, optionally, in combination with a pharmaceutically acceptable carrier, additive or excipient. Systemic administration of modified T cells to the subject may be preferred in certain indications, whereas direct administration at the site of or in proximity a tumor may be preferred in other indications.

In some embodiments, modified T cells can optionally be packaged in a suitable container with written instructions for a desired purpose, such as the reconstitution or thawing (if frozen) of the modified T cells prior to administration to a subject.

One skilled in the art readily appreciates that the present invention is well adapted to carry out the objects and obtain the ends and advantages mentioned, as well as those inherent therein. The details of the description and the examples herein are representative of certain embodiments, are exemplary, and are not intended as limitations on the scope of the invention. Modifications therein and other uses will occur to those skilled in the art. These modifications are encompassed within the spirit of the invention. It will be readily apparent to a person skilled in the art that varying substitutions and modifications may be made to the invention disclosed herein without departing from the scope and spirit of the invention.

The articles "a" and "an" as used herein in the specification and in the claims, unless clearly indicated to the contrary, should be understood to include the plural referents. Claims or descriptions that include "or" between one or more members of a group are considered satisfied if one, more than one, or all of the group members are present in, employed in, or otherwise relevant to a given product or process unless indicated to the contrary or otherwise evident from the context. The invention includes embodiments in which exactly one member of the group is present in, employed in, or otherwise relevant to a given product or process. The invention also includes embodiments in which more than one, or all of the group members are present in, employed in, or otherwise relevant to a given product or process. Furthermore, it is to be understood that the invention provides all variations, combinations, and permutations in which one or more limitations, elements, clauses, descriptive terms, etc., from one or more of the listed claims is introduced into another claim dependent on the same base claim (or, as relevant, any other claim) unless otherwise indicated or unless it would be evident to one of ordinary skill in the art that a contradiction or inconsistency would arise. It is contemplated that all embodiments described herein are applicable to all different aspects of the invention where appropriate. It is also contemplated that any of the embodiments or aspects can be freely combined with one or more other such embodiments or aspects whenever appropriate. Where elements are presented as lists, e.g., in Markush group or similar format, it is to be understood that each subgroup of the elements is also disclosed, and any element(s) can be removed from the group. It should be understood that, in general, where the invention, or aspects of the invention, is/are referred to as comprising particular elements, features, etc., certain embodiments of the invention or aspects of the invention consist, or consist essentially of, such elements, features, etc. For purposes of simplicity those embodiments have not in every case been specifically set forth in so many words herein. It should also be understood that any embodiment or aspect of the invention can be explicitly excluded from the claims, regardless of whether the specific exclusion is recited in the specification. For example, any one or more active agents, additives, ingredients, optional agents, types of organism, disorders, subjects, or combinations thereof, can be excluded.

Where the claims or description relate to a composition of matter, it is to be understood that methods of making or using the composition of matter according to any of the methods disclosed herein, and methods of using the composition of matter for any of the purposes disclosed herein are aspects of the invention, unless otherwise indicated or unless it would be evident to one of ordinary skill in the art that a contradiction or inconsistency would arise. Where the claims or description relate to a method, e.g., it is to be understood that methods of making compositions useful for performing the method, and products produced according to the method, are aspects of the invention, unless otherwise indicated or unless it would be evident to one of ordinary skill in the art that a contradiction or inconsistency would arise.

Where ranges are given herein, the invention includes embodiments in which the endpoints are included, embodiments in which both endpoints are excluded, and embodiments in which one endpoint is included and the other is excluded. It should be assumed that both endpoints are included unless indicated otherwise. Furthermore, it is to be understood that unless otherwise indicated or otherwise evident from the context and understanding of one of ordinary skill in the art, values that are expressed as ranges can assume any specific value or subrange within the stated ranges in different embodiments of the invention, to the tenth of the unit of the lower limit of the range, unless the context clearly dictates otherwise. It is also understood that where a series of numerical values is stated herein, the invention includes embodiments that relate analogously to any intervening value or range defined by any two values in the series, and that the lowest value may be taken as a minimum and the greatest value may be taken as a maximum. Numerical values, as used herein, include values expressed as percentages. For any embodiment of the invention in which a numerical value is prefaced by "about" or "approximately", the invention includes an embodiment in which the exact value is recited. For any embodiment of the invention in which a numerical value is not prefaced by "about" or "approximately", the invention includes an embodiment in which the value is prefaced by "about" or "approximately".

As used herein "A and/or B", where A and B are different claim terms, generally means at least one of A, B, or both A and B. For example, one sequence which is complementary to and/or hybridizes to another sequence includes (i) one sequence which is complementary to the other sequence even though the one sequence may not necessarily hybridize to the other sequence under all conditions, (ii) one sequence which hybridizes to the other sequence even if the one sequence is not perfectly complementary to the other sequence, and (iii) sequences which are both complementary to and hybridize to the other sequence.

"Approximately" or "about" generally includes numbers that fall within a range of 1% or in some embodiments within a range of 5% of a number or in some embodiments within a range of 10% of a number in either direction (greater than or less than the number) unless otherwise stated or otherwise evident from the context (except where such number would impermissibly exceed 100% of a possible value). It should be understood that, unless clearly indicated to the contrary, in any methods claimed herein that include more than one act, the order of the acts of the method is not necessarily limited to the order in which the acts of the method are recited, but the invention includes embodiments in which the order is so limited. It should also be understood that unless otherwise indicated or evident from the context, any product or composition described herein may be considered "isolated".

As used herein the term "comprising" or "comprises" is used in reference to compositions, methods, and respective component(s) thereof, that are essential to the invention, yet open to the inclusion of unspecified elements, whether essential or not. As used herein the term "consisting essentially of" refers to those elements required for a given embodiment. The term permits the presence of additional elements that do not materially affect the basic and novel or functional characteristic(s) of that embodiment of the invention.

The term "consisting of" refers to compositions, methods, and respective components thereof as described herein, which are exclusive of any element not recited in that description of the embodiment.

EXEMPLIFICATION

Introduction

T cells are a main focus for cancer immunotherapies due to their potent anti-tumor activity. While most endogenous T cells in cancer patients are either non-responsive or dysfunctional [1], they can be armed via genetic engineering with a tumor-targeting T cell receptor (TCR) or a chimeric antigen receptor (CAR) [2]. Both TCR and CAR-engineered T cells promote substantial objective clinical responses in synovial carcinoma [3] and B cell lymphoid malignancies [4], respectively. In particular, CAR-expressing T cells expand in vivo in patients with B cell leukemia and can persist up to 24 months post infusion [5]. In contrast, T cell expansion and persistence within the TME is usually hindered in solid tumors by multiple factors such as checkpoint inhibition [6] and metabolic starvation [1].

T cell proliferation requires optimal T cell activation, which integrates signals downstream of the T cell receptor (TCR)/CD3 complex, engagement of costimulatory molecules and cytokines [7]. CAR-based engineering provides the first two factors, while TCR-based engineering remains challenging in providing adequate costimulation [7]. However, for both TCR and CAR engineering strategies, the cytokine component remains a significant limiting factor as the only secreted cytokine by engineered T cells is IL2, which may support the activation and expansion of regulatory T cells (Tregs) [8]. Additional engineering of CAR T cells with common γ chain cytokines such as IL15 is effective in supporting their proliferation and effector function, while the effects on Tregs are limited [9, 10]. However, cytokine engineering can lead to side effects as they are constitutively produced and their receptor being expressed by most T cells and natural killer (NK) cells, requiring the inclusion of safety switches to contain potential toxic effects [11-13]. Thus, the development of inducible and selective engineering processes supporting T cell expansion and survival within the TME remain critical in adoptive T cell therapies in solid tumors.

While most of the studies on cytokines supporting T cell immunotherapies focus on STATS inducing cytokines, recent studies showed that STAT3 signaling enhances CAR T cell effector function in pre-clinical models [14] and it is associated with better clinical outcome in patients with chronic lymphocytic leukemia [15]. IL23 is one of the STAT3 activating cytokines that consists of IL23α p19 and IL12β p40 subunits [16], both expressed by activated macrophages and dendritic cells [17-18]. The IL23 receptor (IL23R) is commonly expressed in Th17 cells [19] and IL23 promotes Th17 cell differentiation and proliferation [17, 91, 20]. Activation-induced expression of the IL23R and IL23α p19 subunit was found in T cells, which allowed for the coupling of the release and activity of IL23 with T cell activation by supplementing the IL12β p40 subunit to T cells. p40-expressing T (p40-Td) cells produce IL23 upon T cell activation, which drives T cell proliferation and survival. Incorporating p40 in CAR- or TCR-engineered T cells enhanced their antitumor activity in xenograft and syngeneic mouse models. Furthermore, IL23 produced by p40-Td cells functions predominantly through an autocrine mechanism with limited effects on bystander cells. Taken together, this approach provides robust and selective proliferative signaling to adoptively transfer tumor-specific T cells within the TME.

Results

TCR Stimulation Upregulates the Expression of IL23R in T Cells.

Figure 1A:
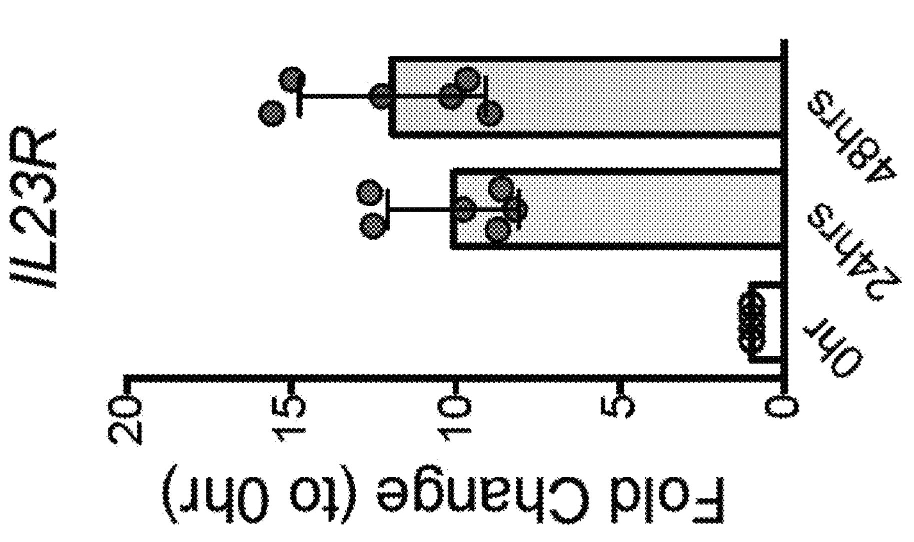
FIGS. 1A-1N demonstrate IL23 supports the expansion of T cells in an activation-inducible dependent manner.
Figure 1C:
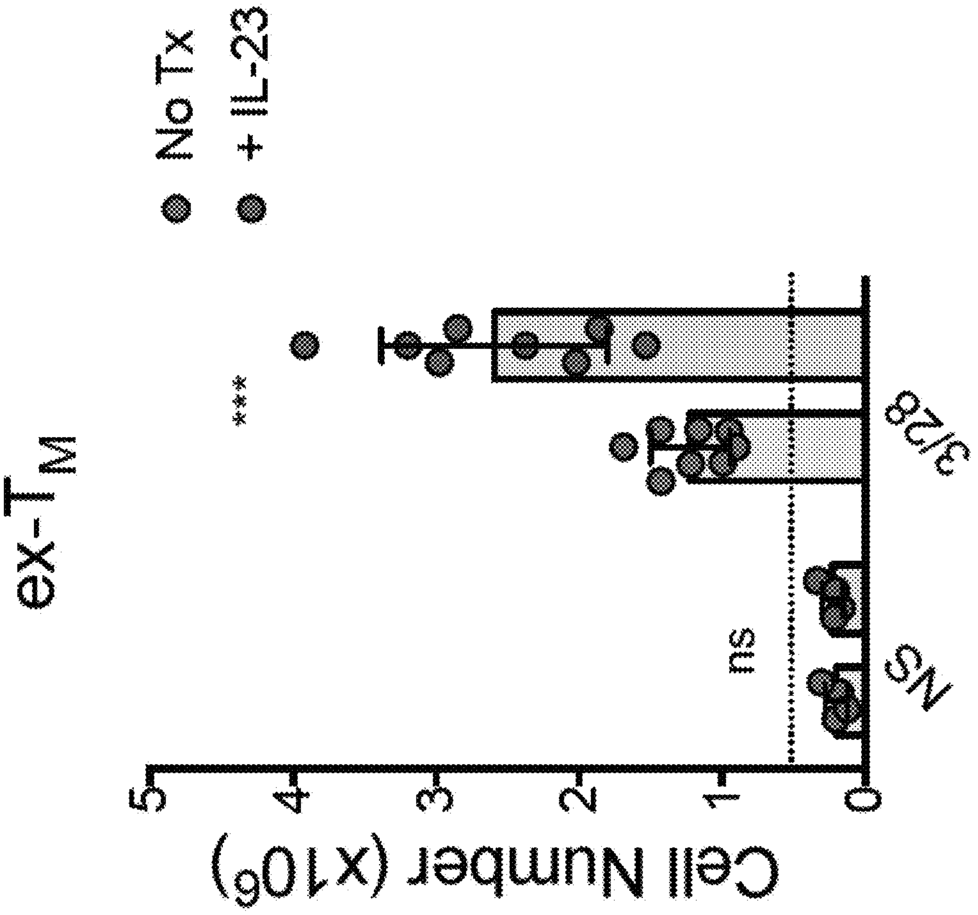
FIG. 1C shows expansion of ex-$T_M$ with or without activation with αCD3 and αCD28 Abs and with or without rIL23 (50 ng/mL). Cell numbers were numerated by flow cytometry at day 7. Data shown are individual values and mean±SD (n=4), *p=0.0002 determined by repeated measured 2-way ANOVA with Sidak post hoc test.
Figure 1D:
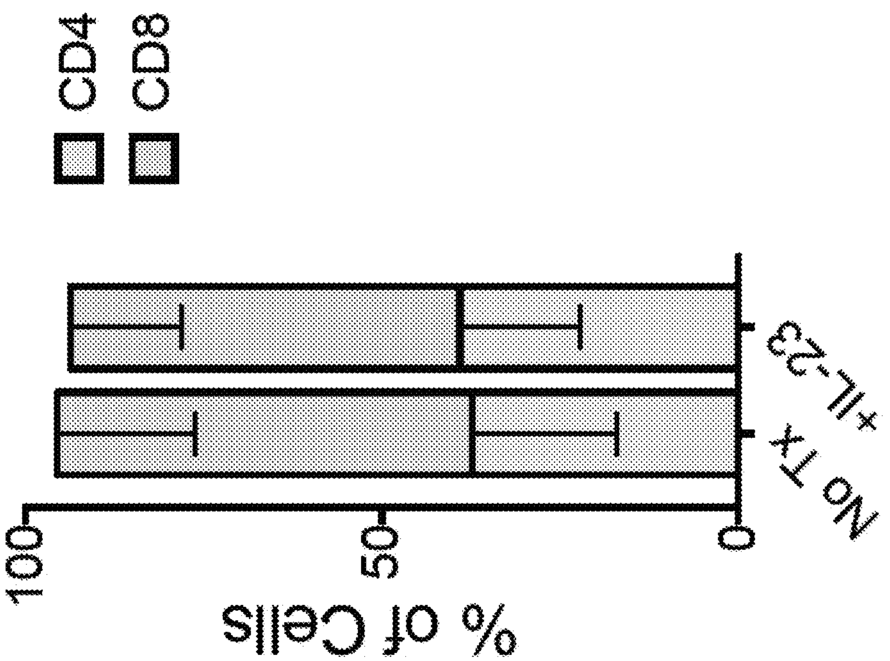
FIG. 1D shows distribution of $CD4^+$ and $CD8^+$ T cells in ex-$T_M$ activated with αCD3 and αCD28 Abs in the presence or absence of 50 ng/mL rIL23 at day 7. Data shown as mean±SD (n=4).
Figure 1E:
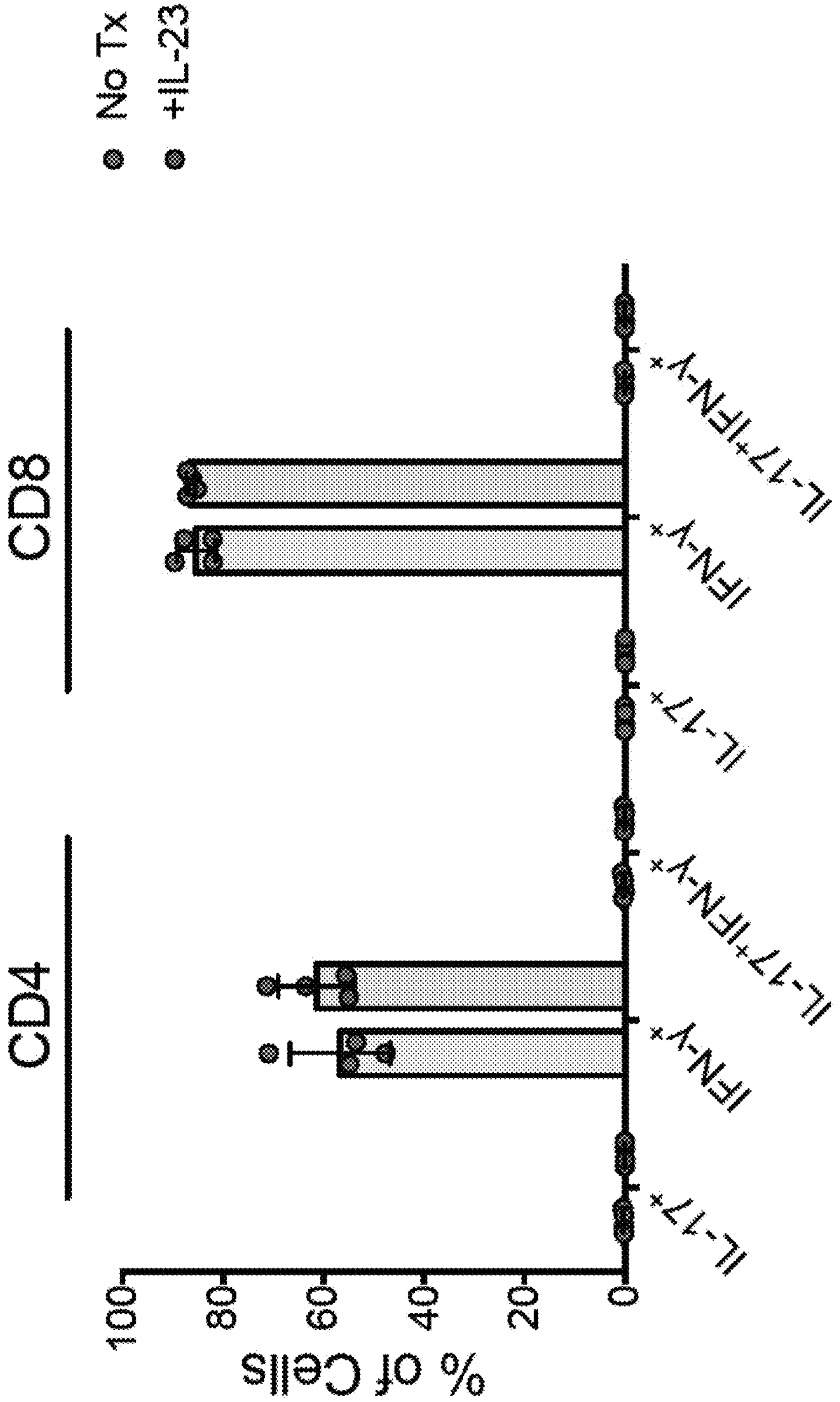
FIG. 1E shows intracellular detection of IFN-γ and IL-17 in $CD4^+$ and $CD8^+$ T cells in ex-$T_M$ activated with αCD3 and αCD28 Abs in the presence or absence of 50 ng/mL rIL23 for 7 days. Data shown as or individual values, mean±SD (n=4).

First evaluated was whether the IL23R is expressed in T cells expanded ex vivo following procedures used to generate CAR T cells for clinical use and that expand T cells phenotypically resembling memory T cells [21] (here collectively called ex-$T_M$). While ex-$T_M$ expanding ex vivo at day 10-12 express low levels of IL23R, TCR stimulation upregulates IL23R expression at both mRNA and protein levels (FIGS. 1A-1B). IL23R expression in ex-$T_M$ is functional because recombinant IL23 supports the expansion of activated ex-$T_M$, as previously observed in $IL23R^+$ Th17 cells [22], while ex-$T_M$ are irresponsive to IL23 in the absence of TCR stimulation (FIG. 1C). Furthermore, ex-$T_M$ responding to IL23 was not polarized to Th17 cells as they show similar CD4 and CD8 ratio as untreated T cells (FIG. 1D), retain a type I cytokine production profile (FIG. 1E), and show similar T-bet/RORγT expression [23] (FIG. 1F). This selective activity of IL23 without skewing towards a pathogenic Th17 subset prompted us to explore whether the IL23/IL23R axis can be exploited to support the expansion of activated T cells within the TME.

Functional Engineering of the IL23/IL23R Axis in T Cells.

Figure 1G:
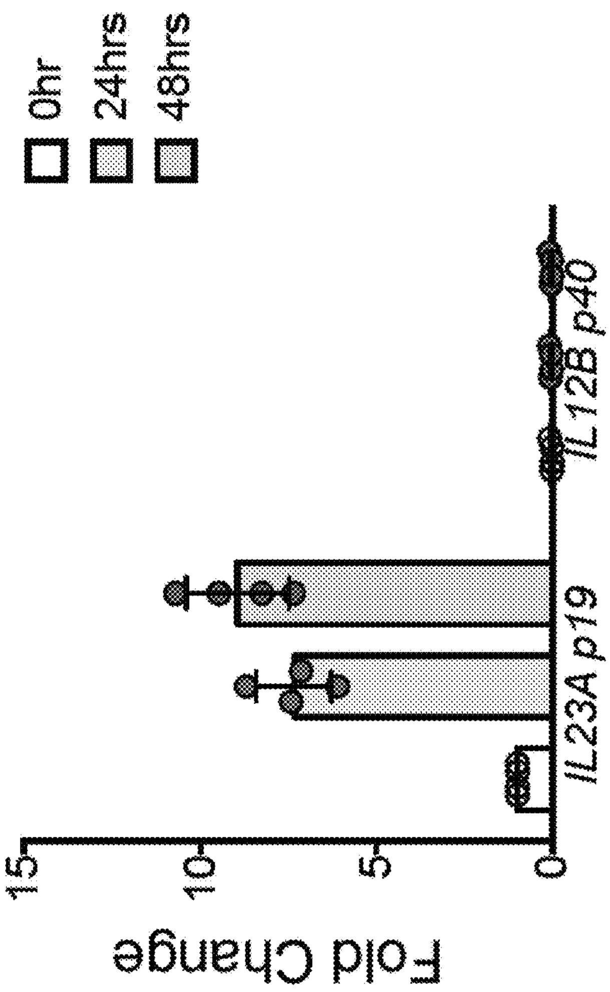
FIG. 1G shows mRNA expression of the IL23 subunits p19 (IL23A) and p40 (IL12B) in ex-$T_M$ activated with αCD3 and αCD28 Abs at time 0, 24, 48 hours as determined by qRT-PCR. Data are expressed as fold change in expression normalized to the housekeeping gene 18S and to the expression at time 0. Error bars denote SD (n=4).
Figure 1F:
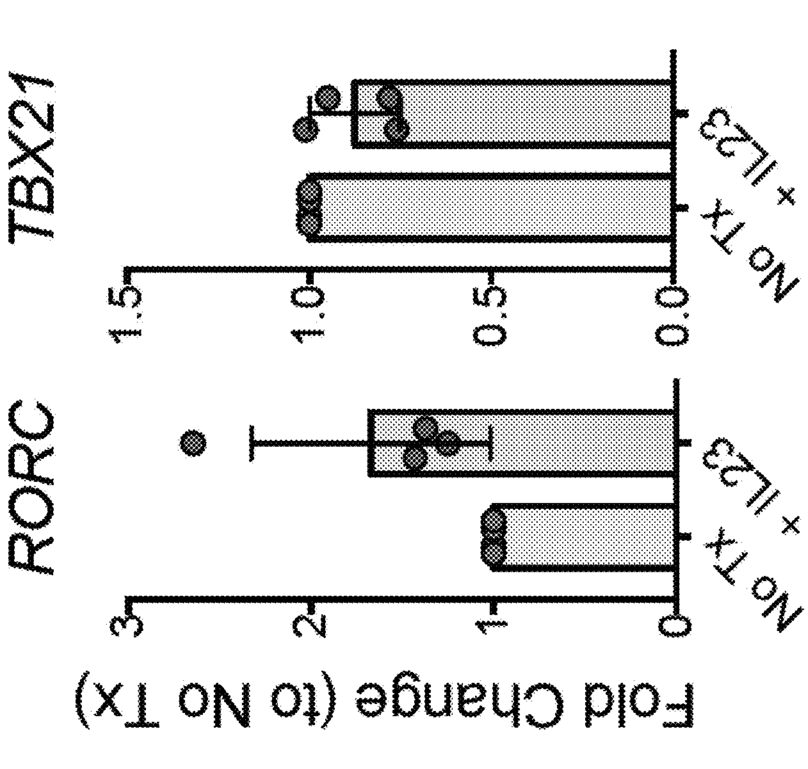
FIG. 1F shows relative expression of the Th17 and Th1 transcription factor RORγT and Tbet, respectively assessed by qRT-PCR in ex-$T_M$ activated with αCD3 and αCD28 Abs in the presence or absence of 50 ng/mL rIL23 for 7 days. Data shown as individual values, mean±SD (n=4).
Figure 1H:
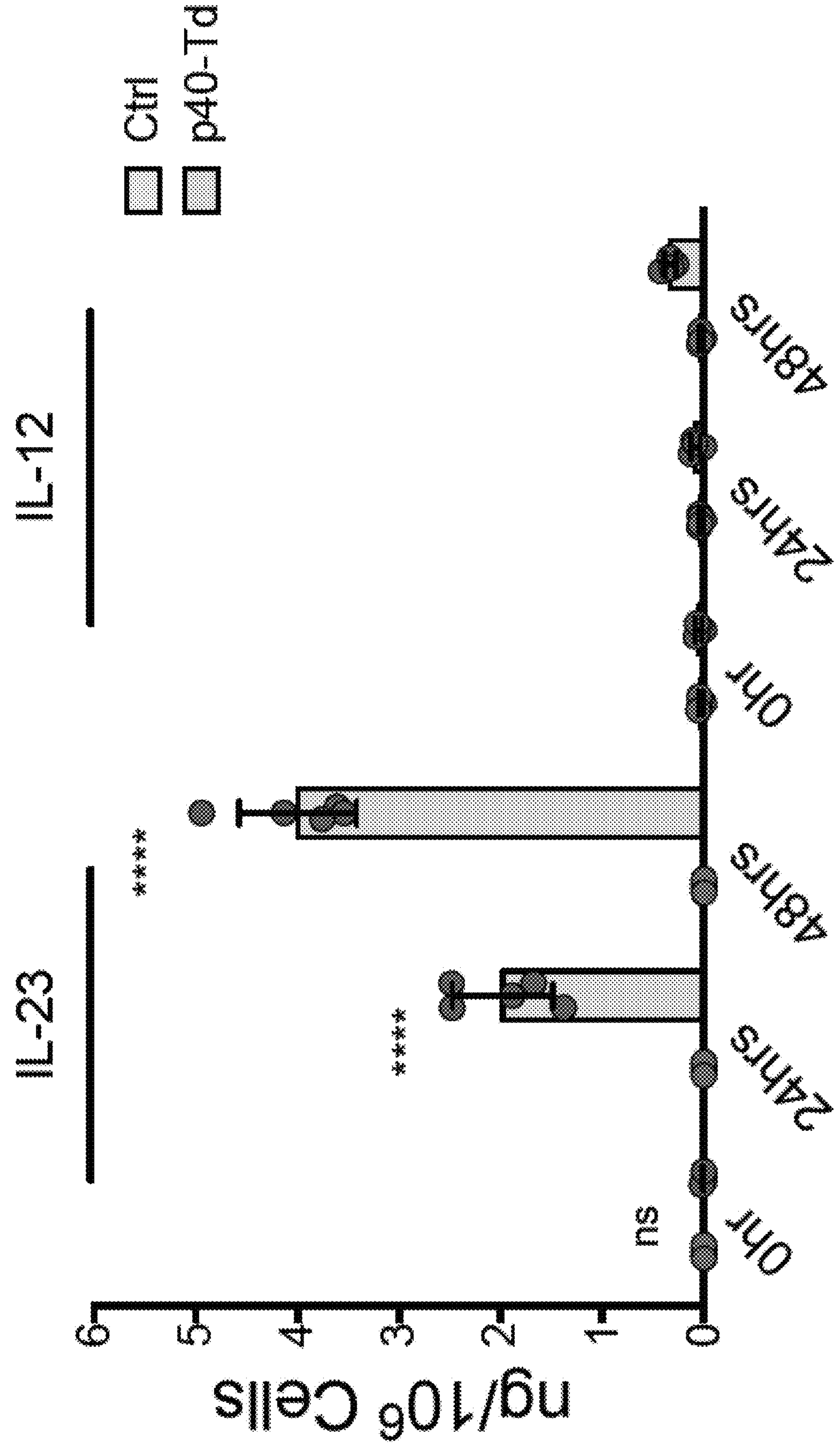
FIG. 1H shows detection of IL23 secreted by Ctrl cells or p40-Td cells activated with αCD3 and αCD28 Abs for 0, 24 and 48 hours as measured by ELISA. Data shown as individuals and mean±SD (n=5). p<0.0001 determined by repeated measured 2-way ANOVA with Sidak post hoc test.
Figure 1I:
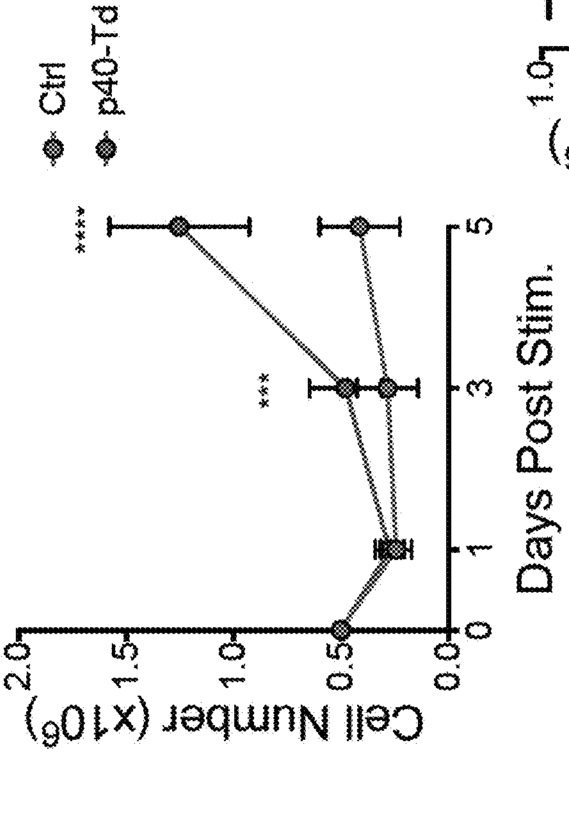
FIG. 1I shows numeric expansion of Ctrl cells and p40-Td cells activated with αCD3 and αCD28 Abs. Data shown as mean±SD (n=13). *p=0.0006, **p<0.0001 determined by repeated measured 2-way ANOVA with Sidak post hoc test.
Figure 1J:
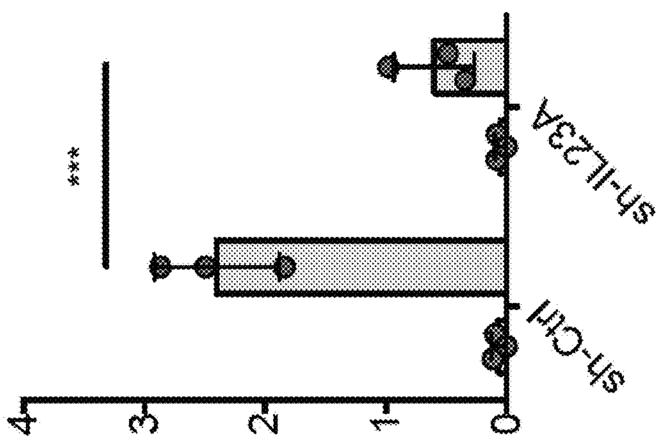
FIG. 1J shows detection of IL23 secreted by activated Ctrl cells and p40-Td cells co-transduced with either the vector encoding control shRNA (sh-Ctrl cells) or IL23A-shRNA (sh-IL23A). Data shown as individual values and mean±SD (n=3). *p=0.0002 determined by repeated measured 2-way ANOVA with Sidak post hoc test.
Figure 1K:
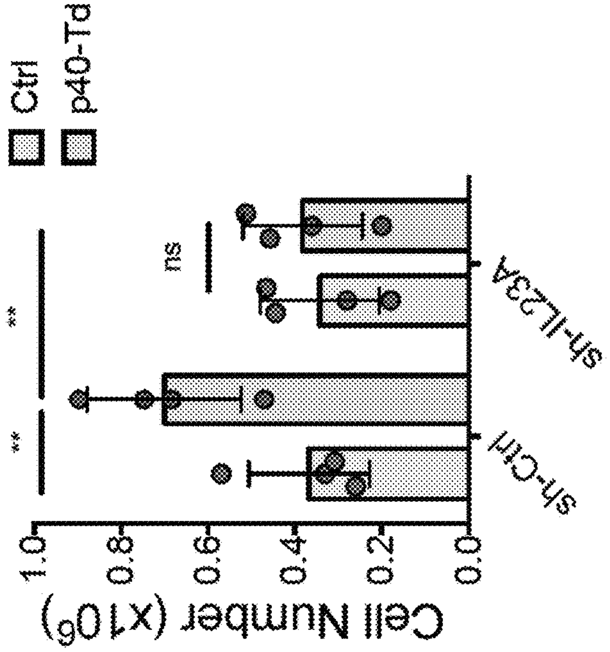
FIG. 1K shows cell counts at day 5 of sh-Ctrl cells or sh-IL23A cells activated with αCD3 and αCD28 Abs. Data shown as individual values and mean±SD (n=4). p=0.0069 for Ctrl cells:sh-Ctrl cells vs. p40-Td cells:sh-Ctrl cells and p=0.0056 for p40:sh-Ctrl cells vs. p40-Td cells:sh-IL23A, determined by repeated measured 2-way ANOVA with Sidak post hoc test.
Figure 7A:
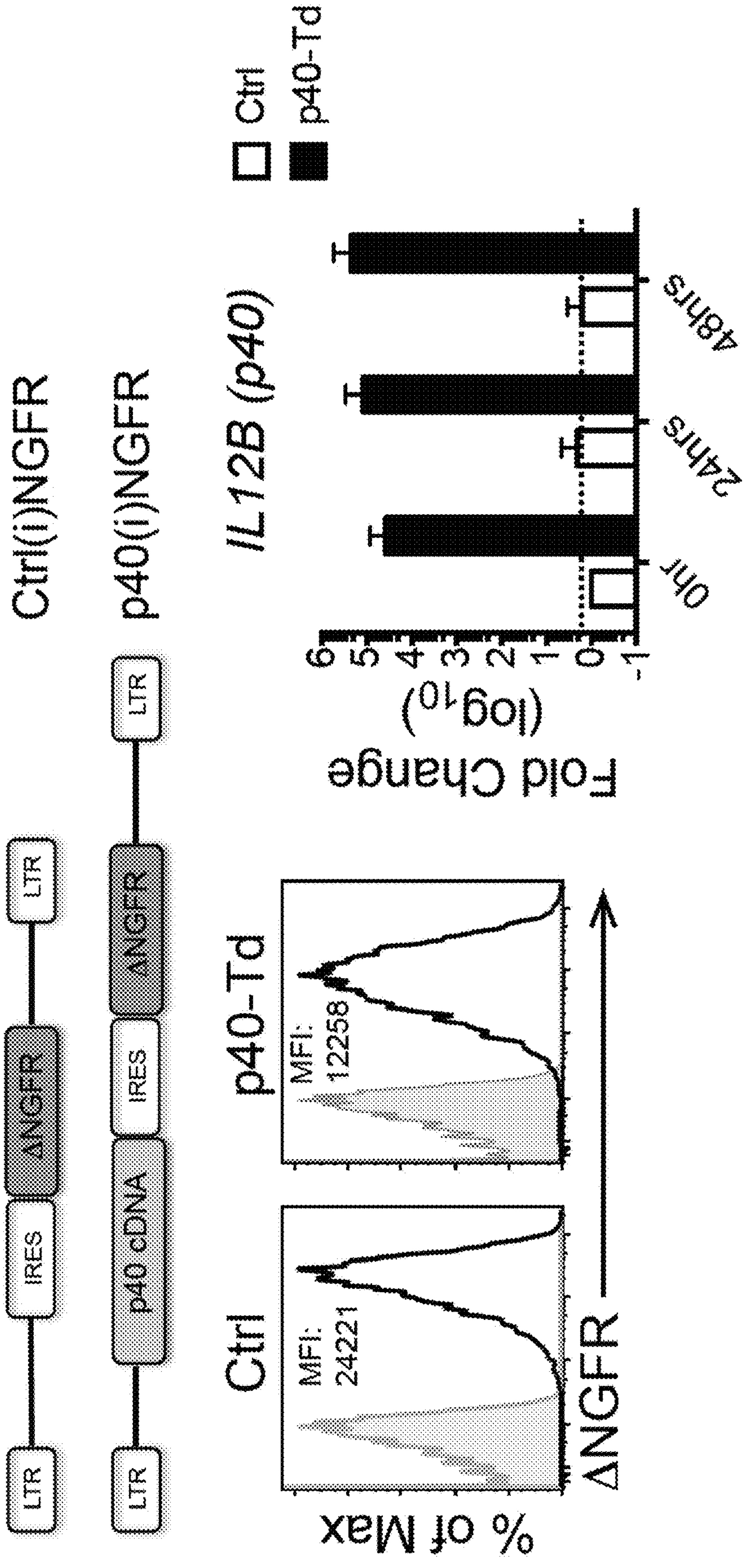
FIGS. 7A-7E provide a phenotypic analysis of p40-Td cells.
Figure 7C:
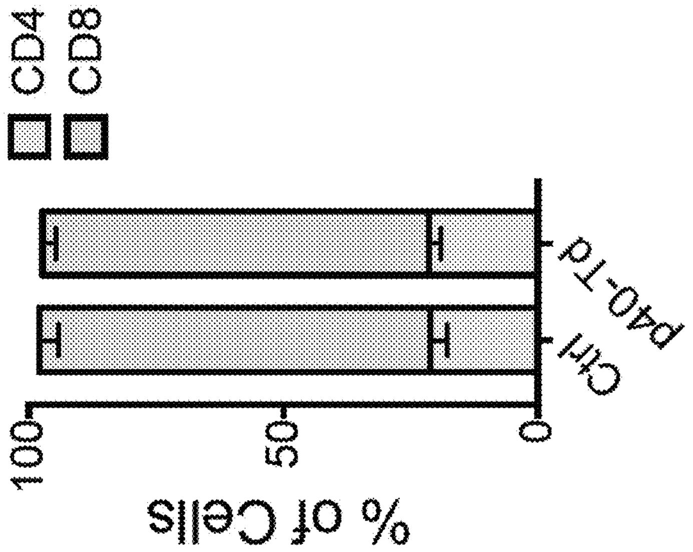
Figure 7B:
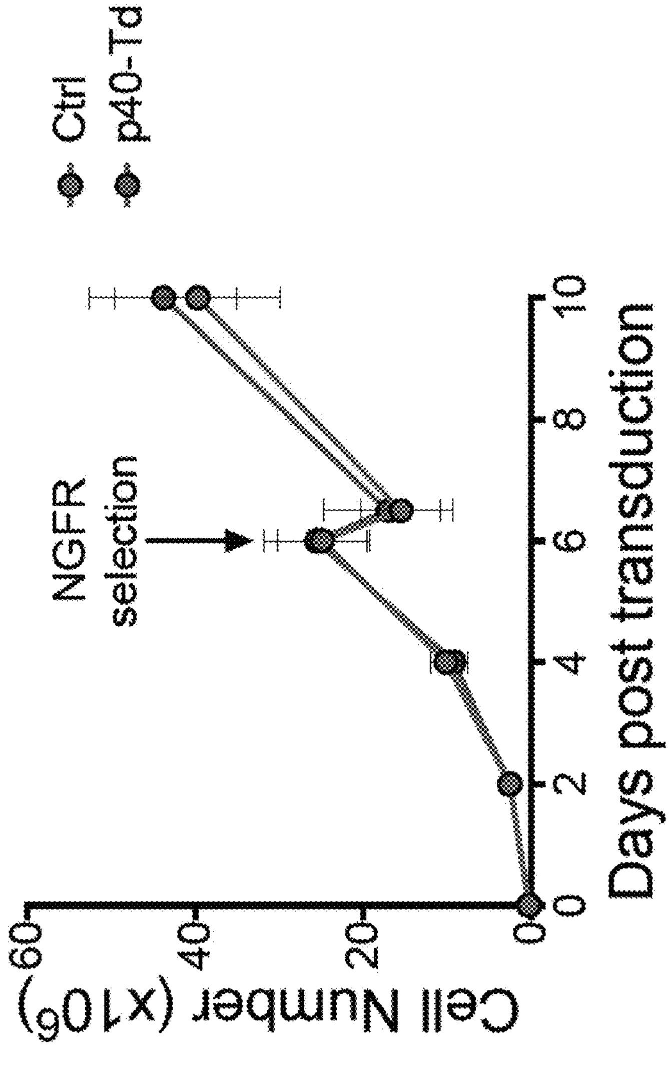
Figure 7D:
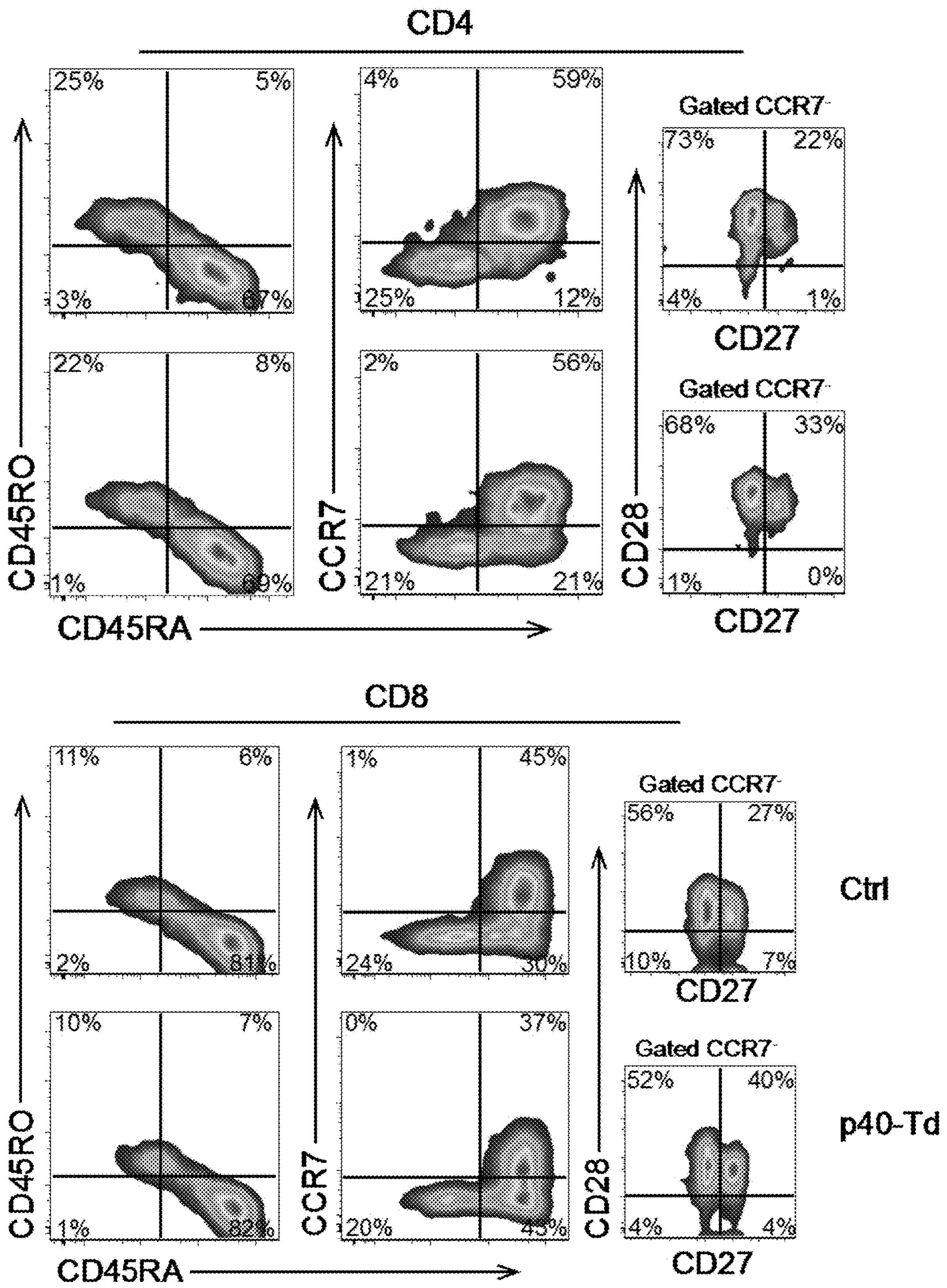
Figure 7E:
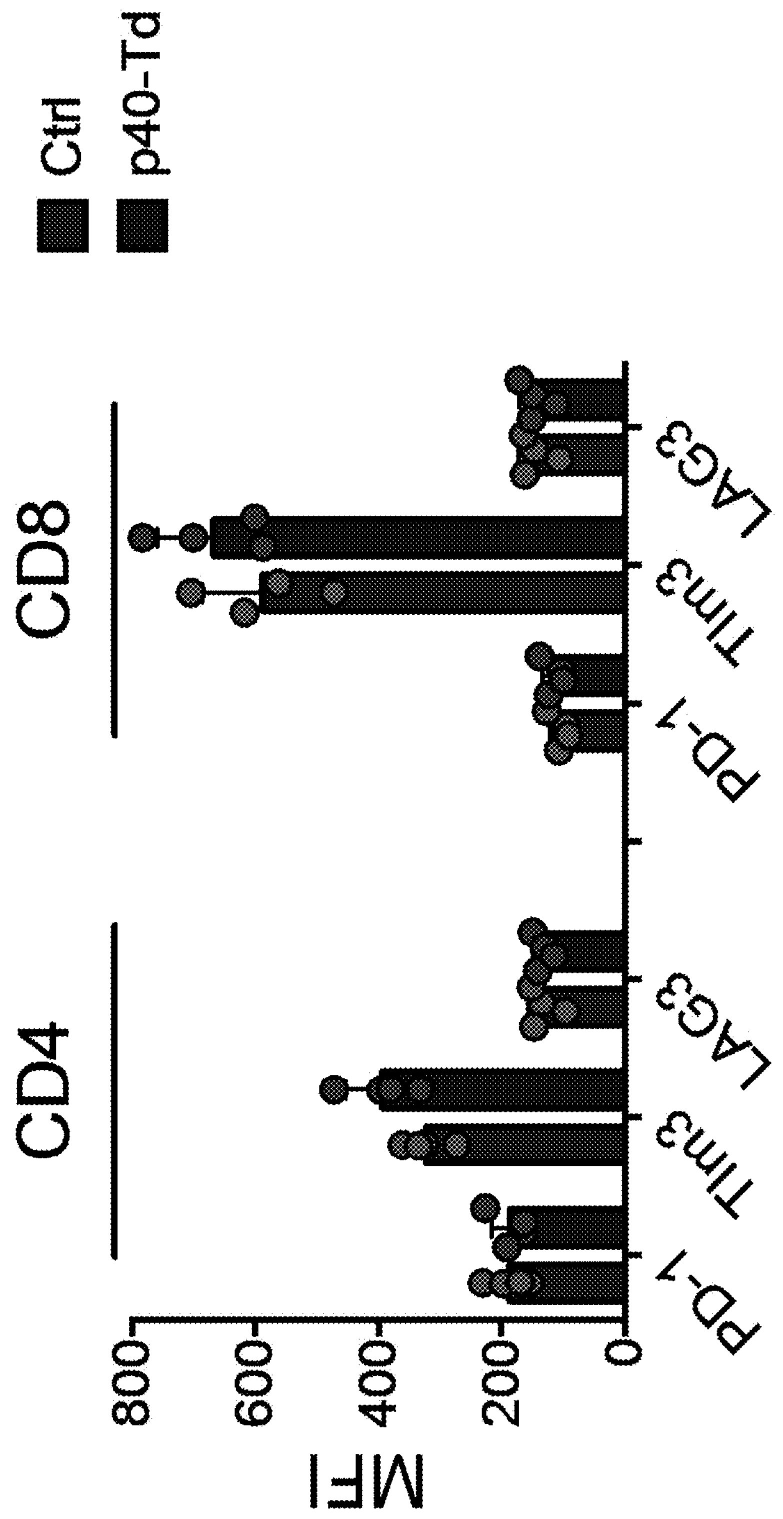
Figure 8A:
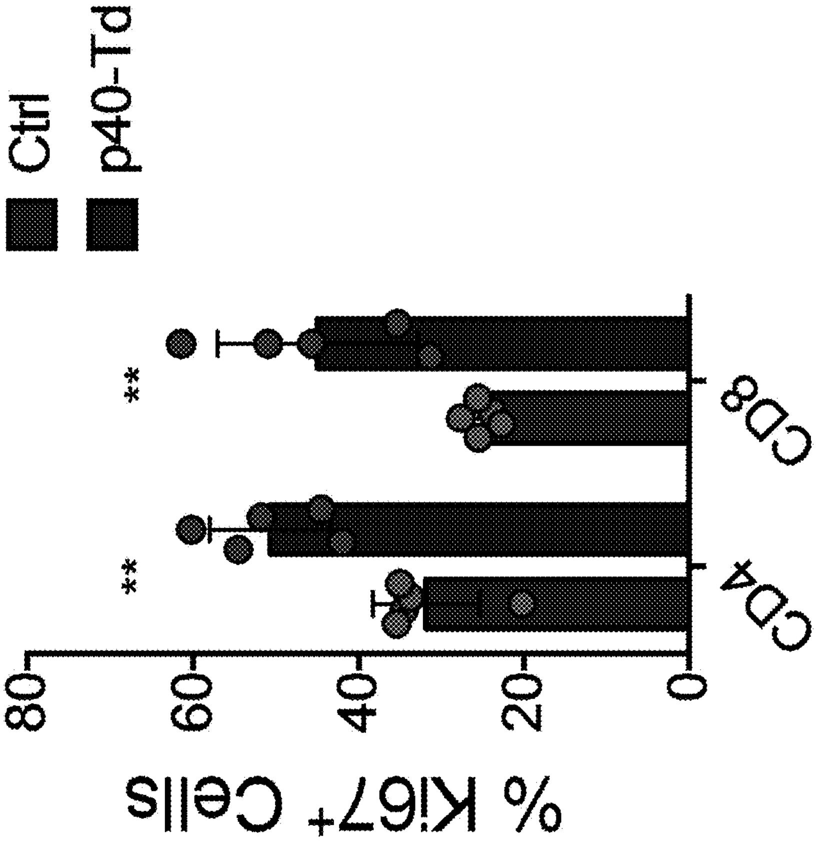
FIGS. 8A-8D demonstrate p40-Td cells show superior proliferation and survival upon activation.
Figure 8B:
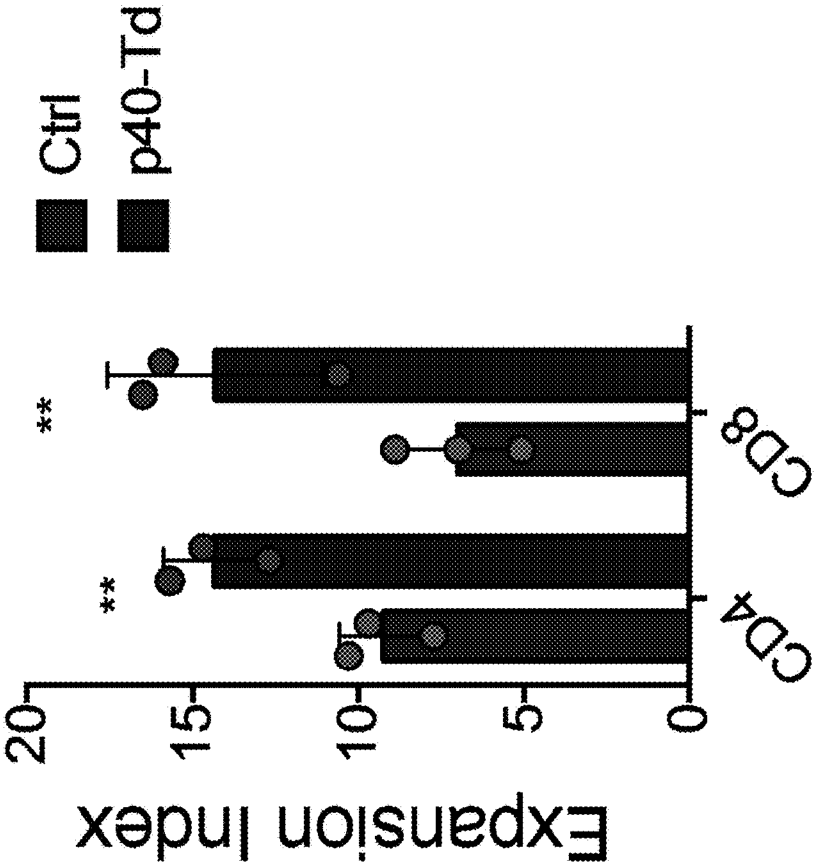
Figure 8D:
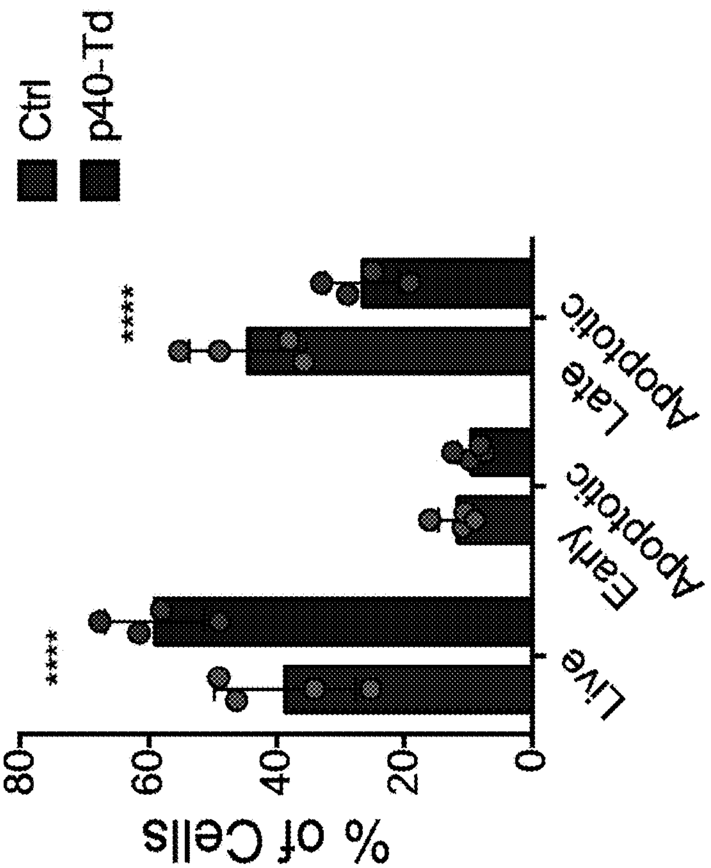
Figure 8C:
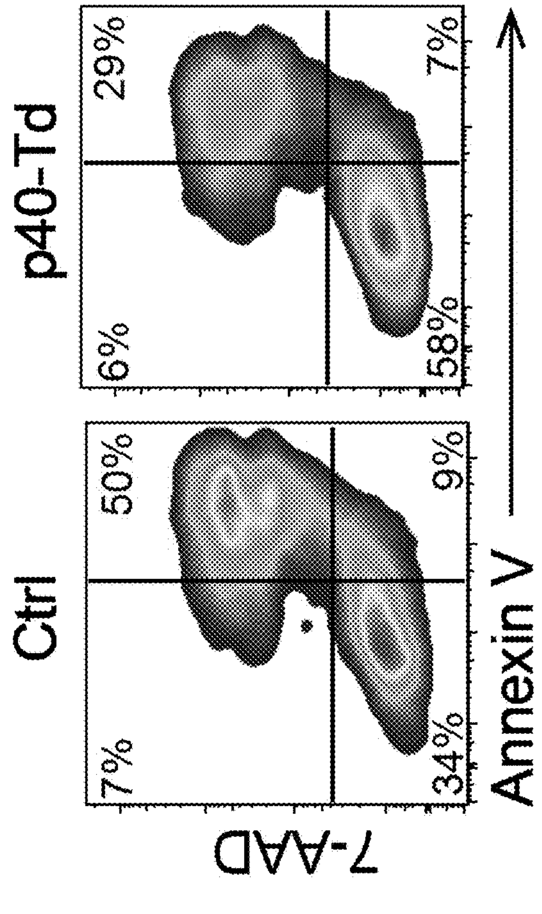

Unexpectedly, it was observed that ex-$T_M$ upregulates the IL23α p19 subunit upon TCR stimulation, but not the IL12β p40 subunit (FIG. 1G). The observed inducible expression of both IL23R and IL23α p19 subunit in ex-$T_M$ in response to TCR stimulation offers the unique opportunity to genetically engineer these cells with the IL12β p40 subunit to produce and utilize IL23 upon TCR stimulation. The p40 subunit has been supplemented to ex-$T_M$ via gamma retroviral transduction to generate p40-expressing T (p40-Td) cells (FIG. 7A). p40-Td cells, but not empty vector-transduced T (Ctrl) cells, secrete IL23 upon TCR stimulation (FIG. 1H). Of note, p40-Td cells released limited amount of IL12 (<50 pg/mL), a cytokine that shares the p40 subunit with IL23 [20] (FIG. 1H). In the absence of TCR stimulation, p40-Td and Ctrl cells showed comparable phenotypic characteristics and expansion in culture (FIGS. 7B-7E). In contrast, p40-Td cells showed superior expansion upon TCR activation as compared to Ctrl cells (FIG. 1E). This effect can be attributed to both increased cell division (FIGS. 8A-8B) and reduced apoptosis (FIG. 8C). IL23-mediated responses of p40-Td cells requires the endogenous IL23α subunit because knockdown of the IL23A gene abolishes both IL23 production (FIG. 1J) and IL23-mediated T cell expansion (FIG. 1K) of p40-Td cells.

Figure 1L:
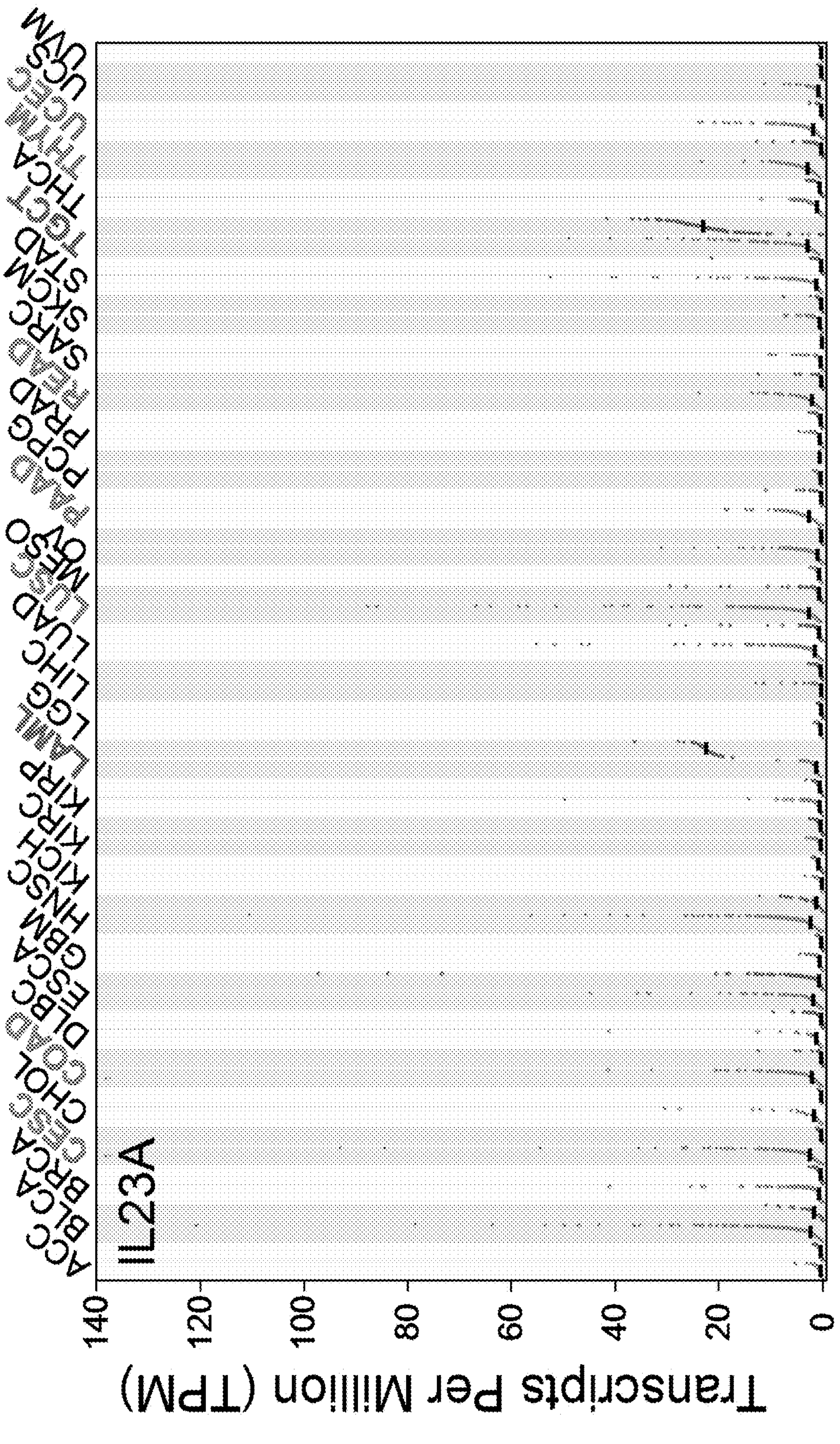
FIG. 1L shows expression (transcript per million) of IL23A (left) and IL12B (right) mRNA in tumor (red dots) and adjacent normal tissues (green dots) from different cancer patients plotted using TCGA data. Tumor types highlighted in red indicate higher expression in tumor tissues vs. normal tissues, while those highlighted green indicate lower expression.
Figure 1L:
Figure 1M:
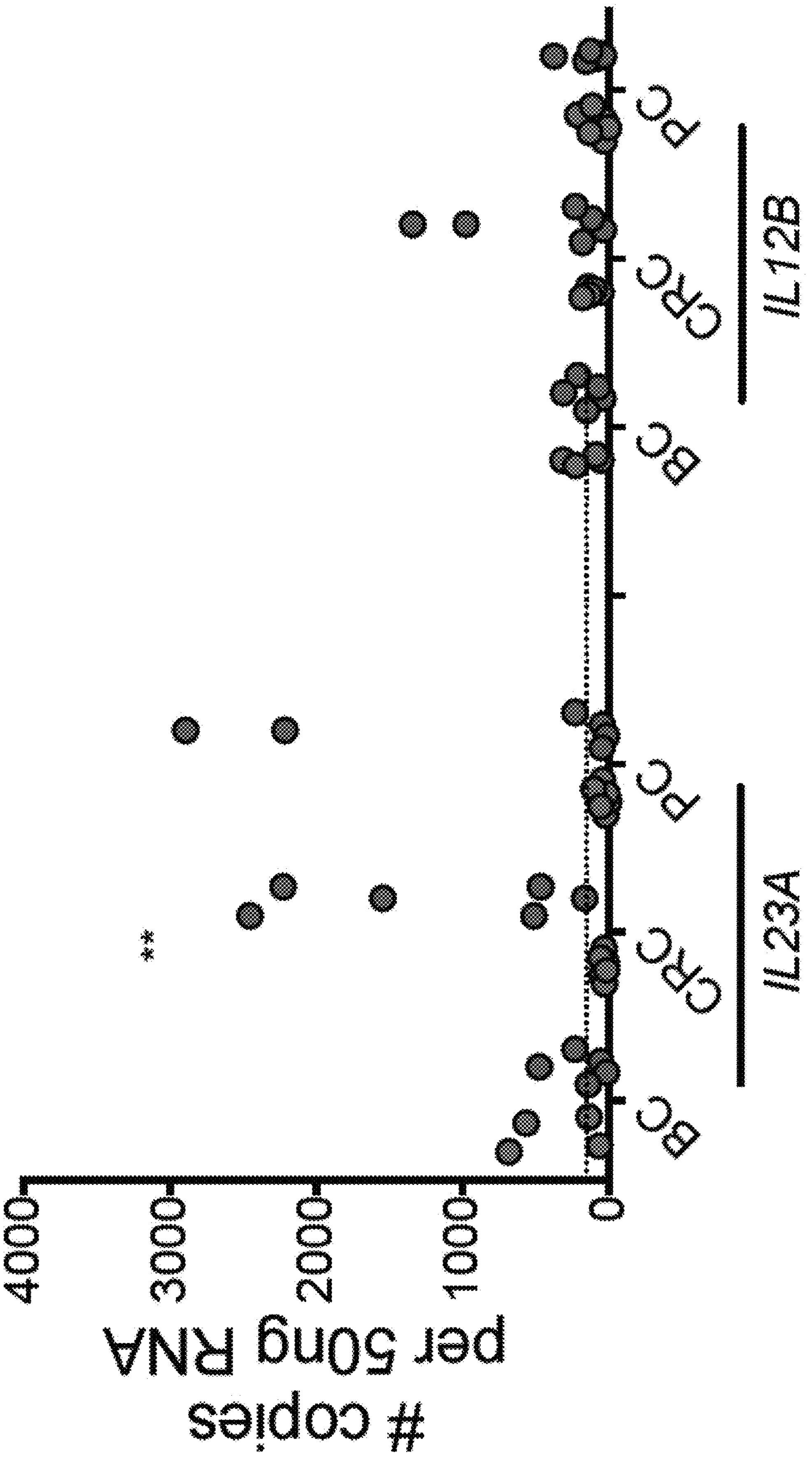
FIG. 1M shows expression of IL23A and IL12B genes determined by qRT-PCR in breast cancer (BC), colon rectal cancer (CRC) and pancreatic cancer (PC) and paired adjacent normal tissues. Data are shown as copies of RNA per 50 ng RNA (n=6). Dotted line indicates the detection limit of the qRT-PCR assay used ($C_T$>35). p=0.0019 was determined by 1-way ANOVA with Sidak post hoc test.
Figure 1N:
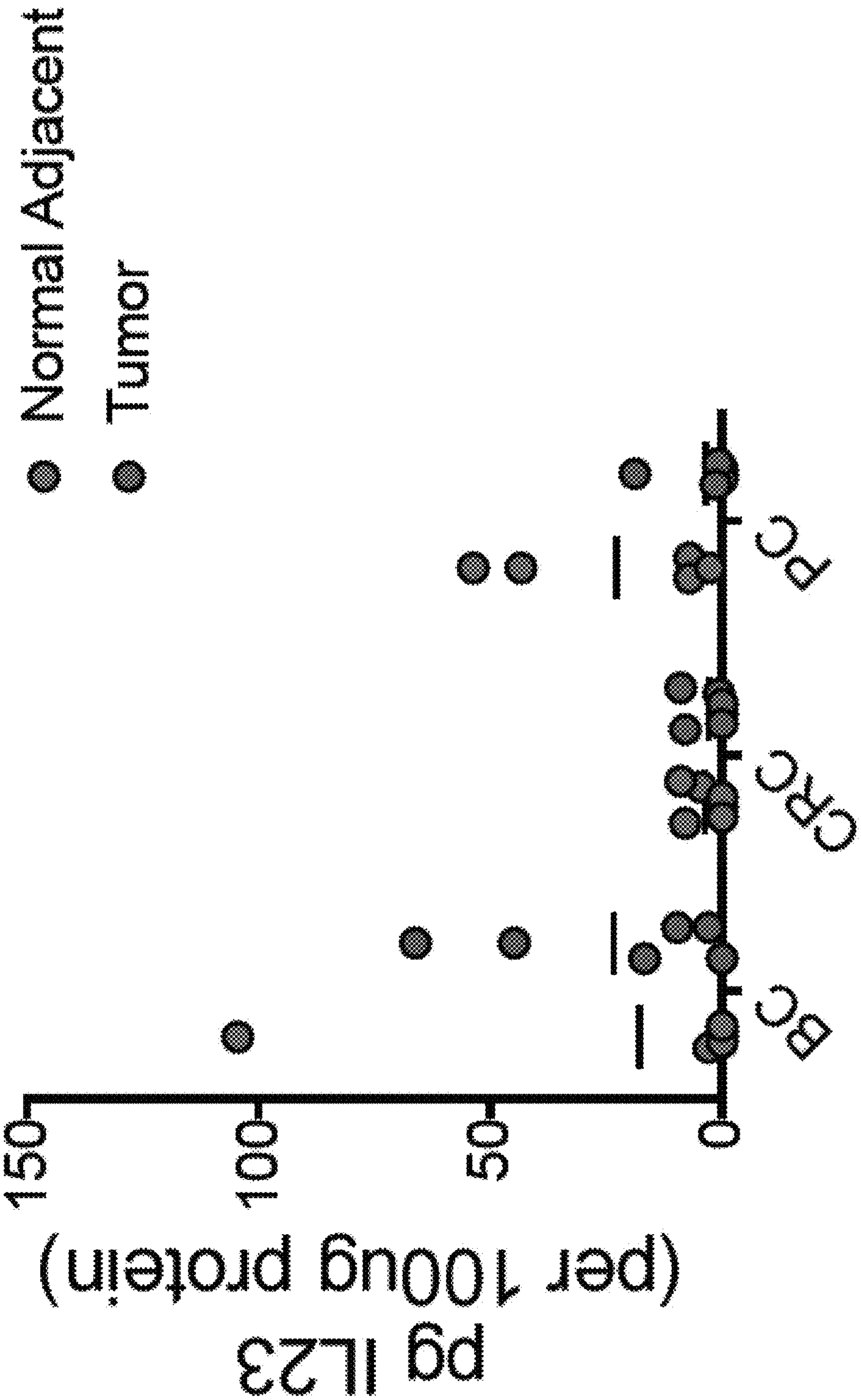

Previous studies showed elevated IL23A mRNA levels in tumor biopsies, suggesting the potential role of IL23 in tumor progression, especially in colorectal carcinoma (CRC) [24, 25]. However, as a heterodimeric protein, both IL23α and IL12β subunits must be present in the same cell to produce and release IL23. Analysis of RNA-sequencing data from The Cancer Genome Atlas (TCGA) showed that while the IL23A transcript is upregulated in many tumor specimens, the IL12B transcript is barely detectable in both tumor and normal tissue specimens (FIG. 1L), predicting the absence of IL23 within the TME. The expression of the IL23 subunits was also measured at both mRNA and protein levels with qPCR and ELISA, respectively in 18 tumor specimens (CRC, pancreatic ductal adenocarcinoma (PDAC) and breast cancer (BC)). While IL23A gene is upregulated in CRC tumor specimens, IL12B was not expressed (FIG. 1M) and IL23 protein was absent in most of the supernatants obtained from CRC specimens (FIG. 1N). Therefore, IL23 p40 engineering of T cells may support T cell expansion in a TCR activation dependent manner within the TME that is deprived of IL23.

Transcriptome Analysis of Activated p40-Td Cells Reveals Enriched STAT3 and Hypoxia Gene Signature.

Figure 2A:
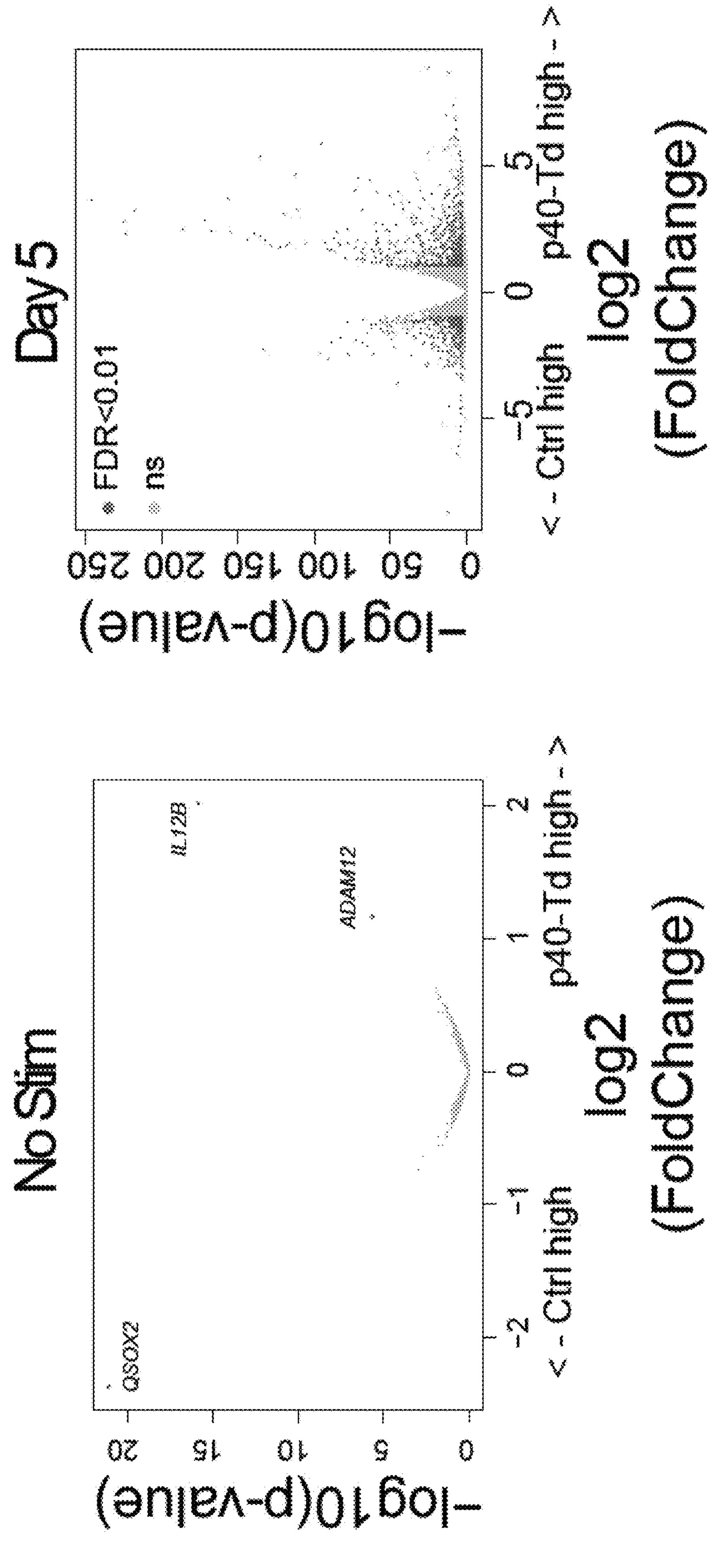
Figure 2B:
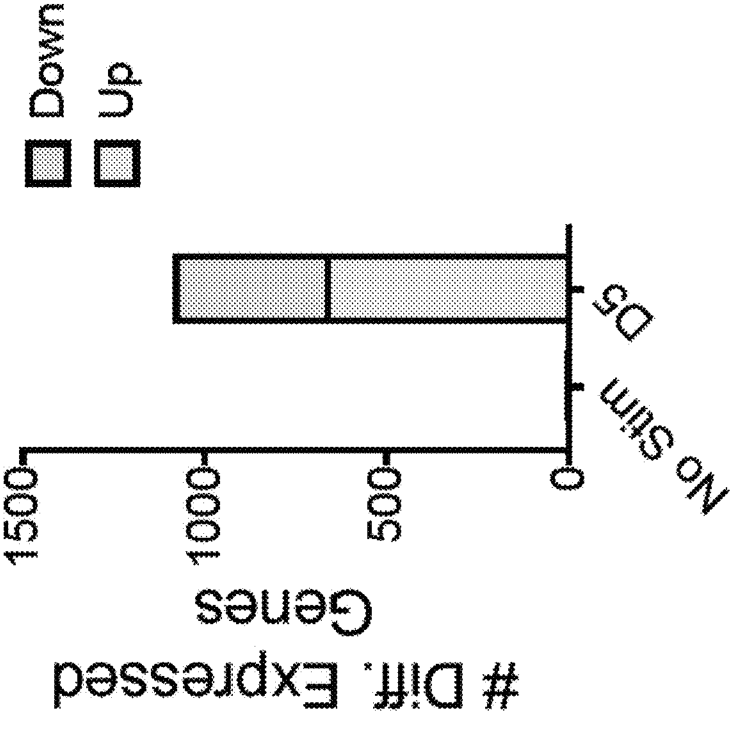
Figure 2C:
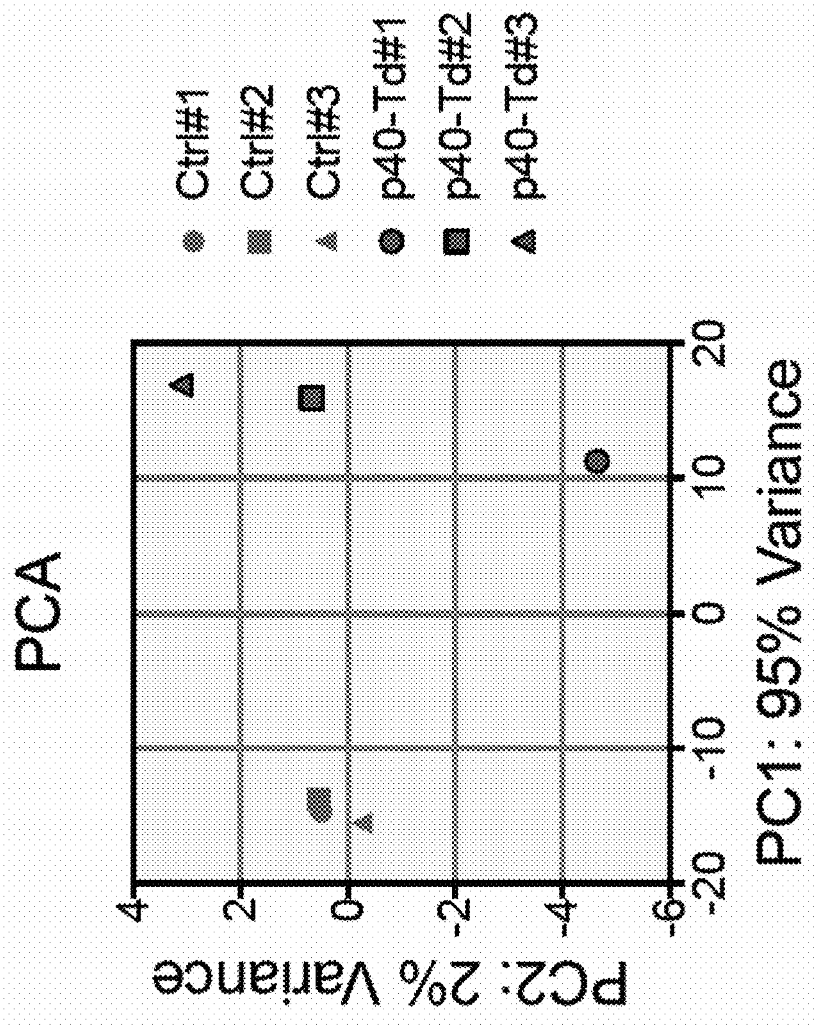
Figure 2D:
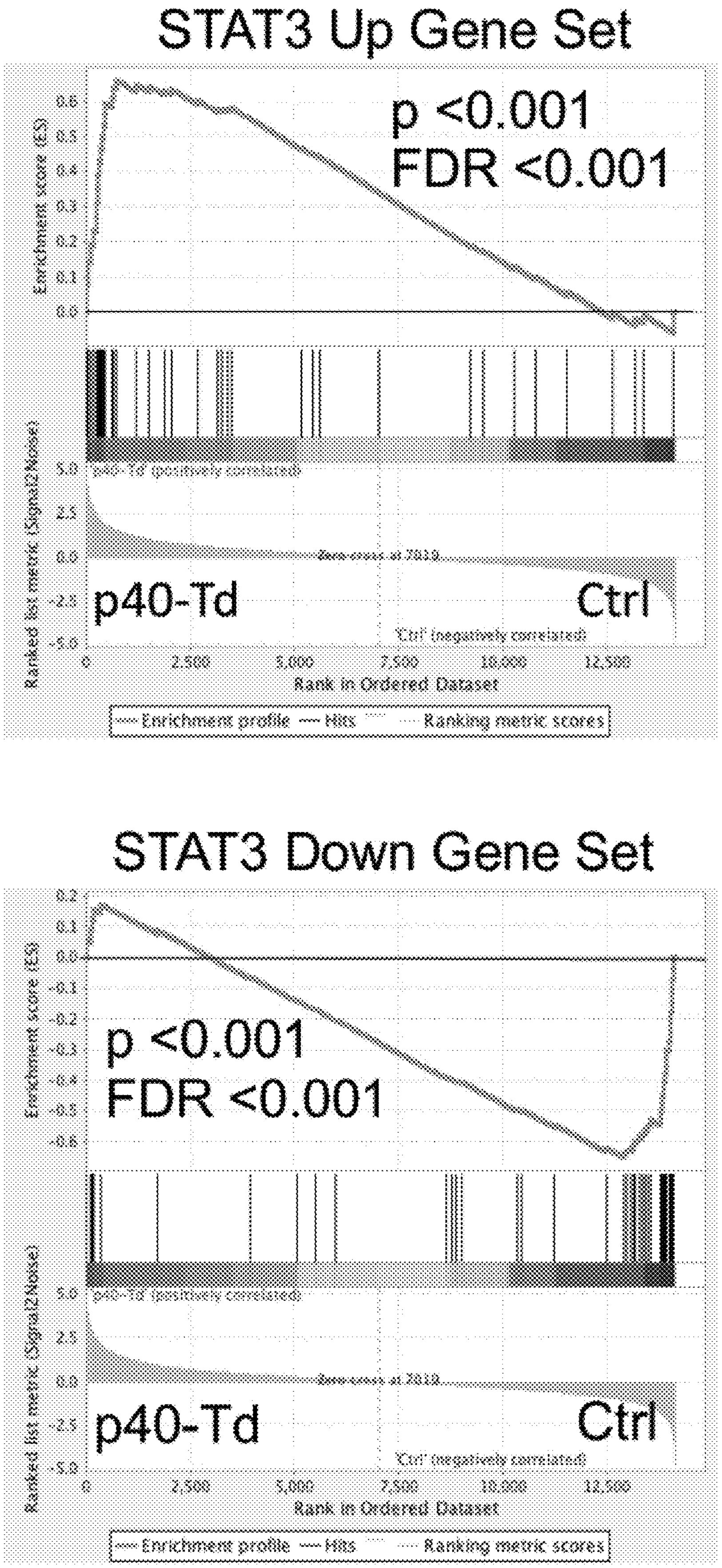
Figure 2D:
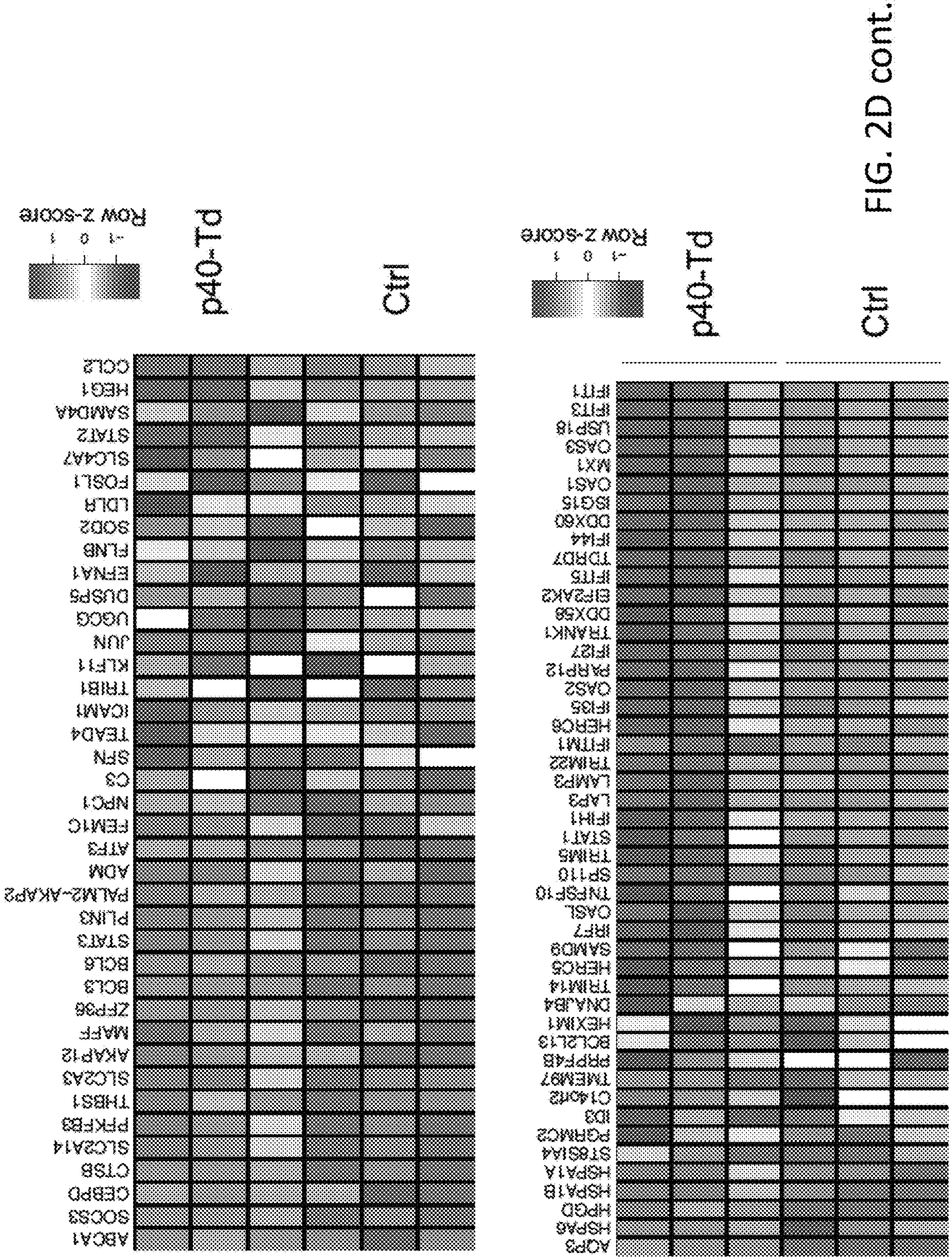
Figure 2E:
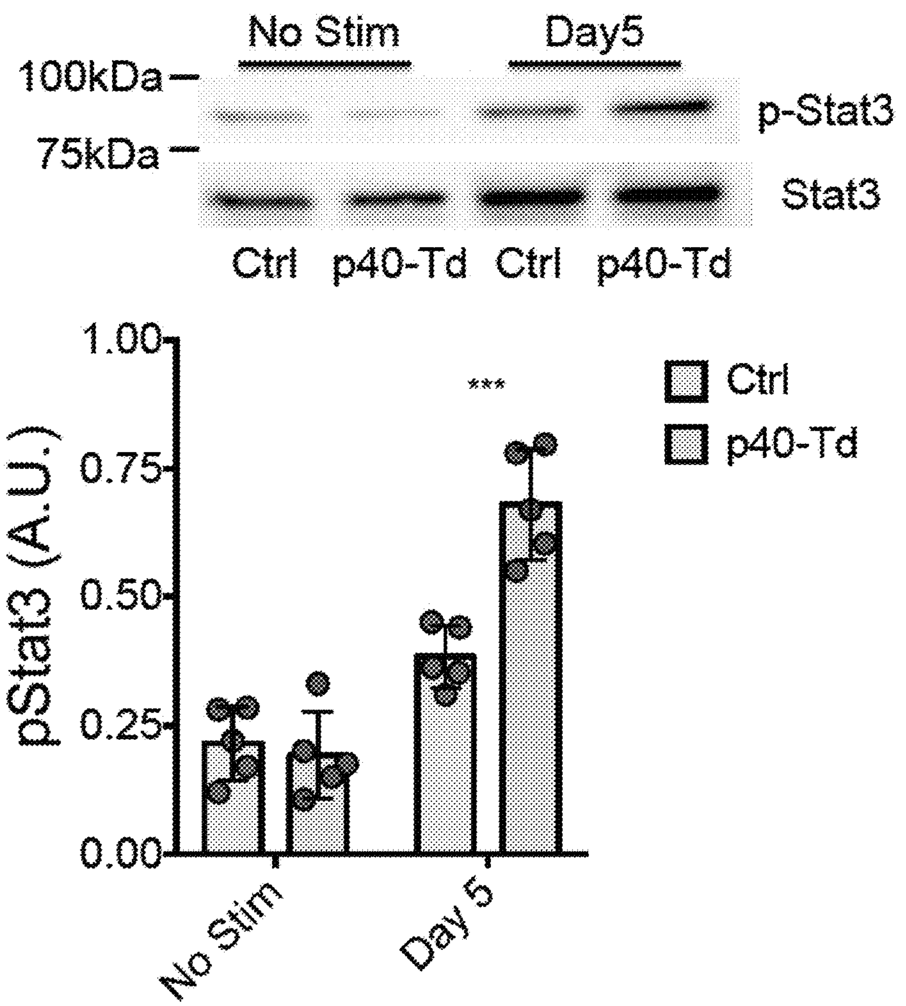
Figure 2F:
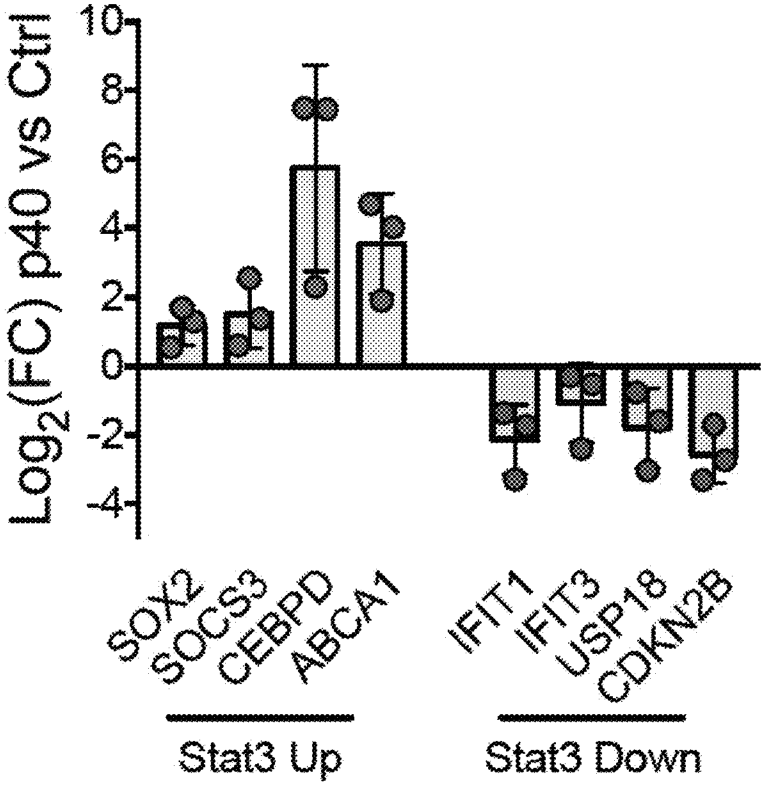
Figure 2H:
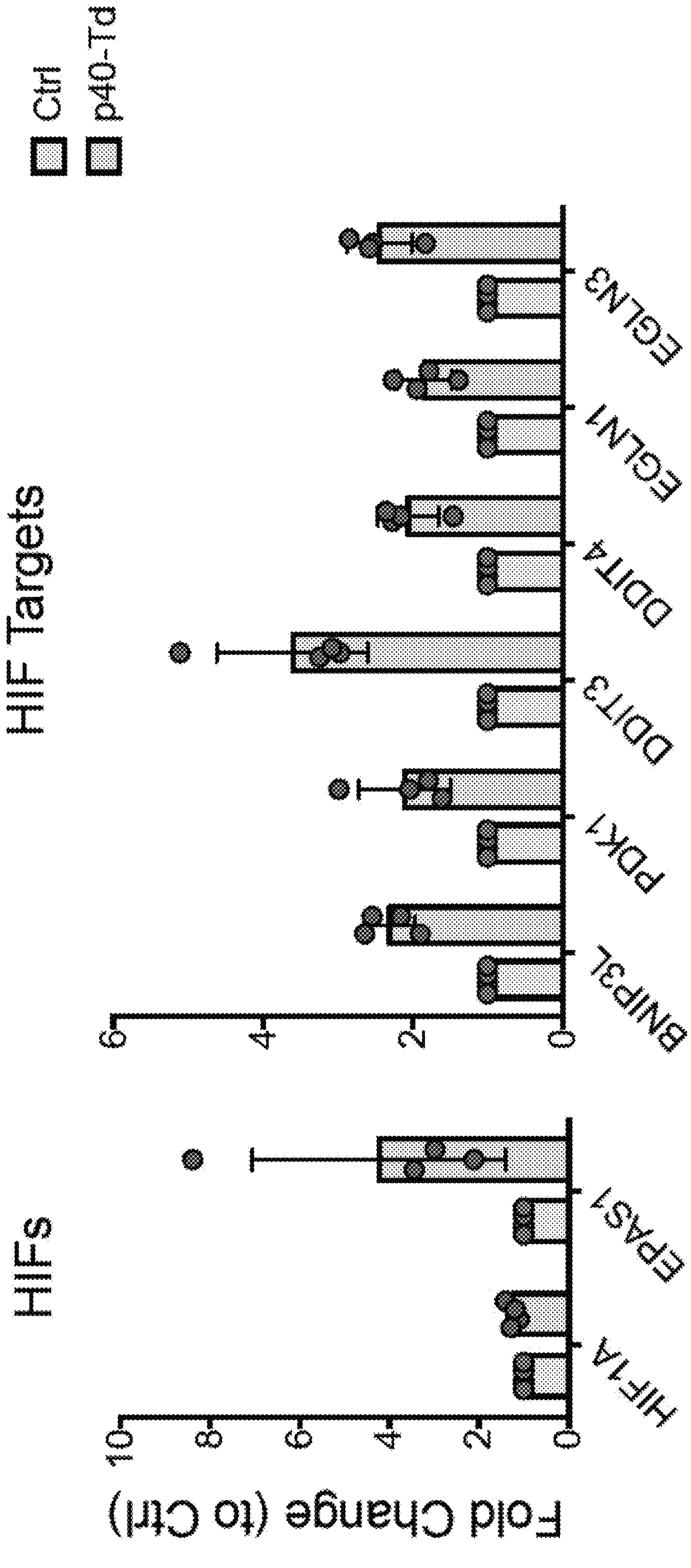

RNA-Seq analysis was performed to define the molecular pathways involved in p40-Td cells. Ctrl cells and p40-Td cells shared similar gene expression profile in the absence of TCR stimulation (FIG. 2A). In contrast, after TCR activation, p40-Td cells showed a different molecular signature as compared to Ctrl cells (FIGS. 2A-2C), indicating the requirement of TCR stimulation to fully exploit the effects of the engineered IL23/IL23R axis in ex-$T_M$. Specifically, gene set enrichment analysis (GSEA) showed a significant enrichment of STAT3 upregulated genes in activated p40-Td cells and STAT3 downregulated genes in Ctrl cells (FIG. 2D), suggesting an elevated STAT3 activity in p40-Td cells. The molecular signature was validated by detecting increased STAT3 phosphorylation in activated p40-Td cells (FIG. 2E), and differential expression of STAT3 regulated genes (50×2, SOCS3, CEBPD, ABCA1, IFIT1, IFIT3, USP18 and CDKN2B) (FIG. 2F). Furthermore, an enrichment of genes within the hypoxia hallmark gene set was observed in TCR stimulated p40-Td cells as compared to Ctrl cells (FIG. 2G) and mRNA upregulation of hypoxia-inducible factors (HIFs) and other HIF target genes was also observed (FIG. 2H). Overall, these data highlight the activation of the STAT3 pathway upon TCR activation in p40-Td cells, indicating a dominant role of IL23 signaling in these cells.

p40 Expression Enhances the Anti-Tumor Activity of CAR T Cells in Xenograft Models of Solid Tumors.

Figure 3B:
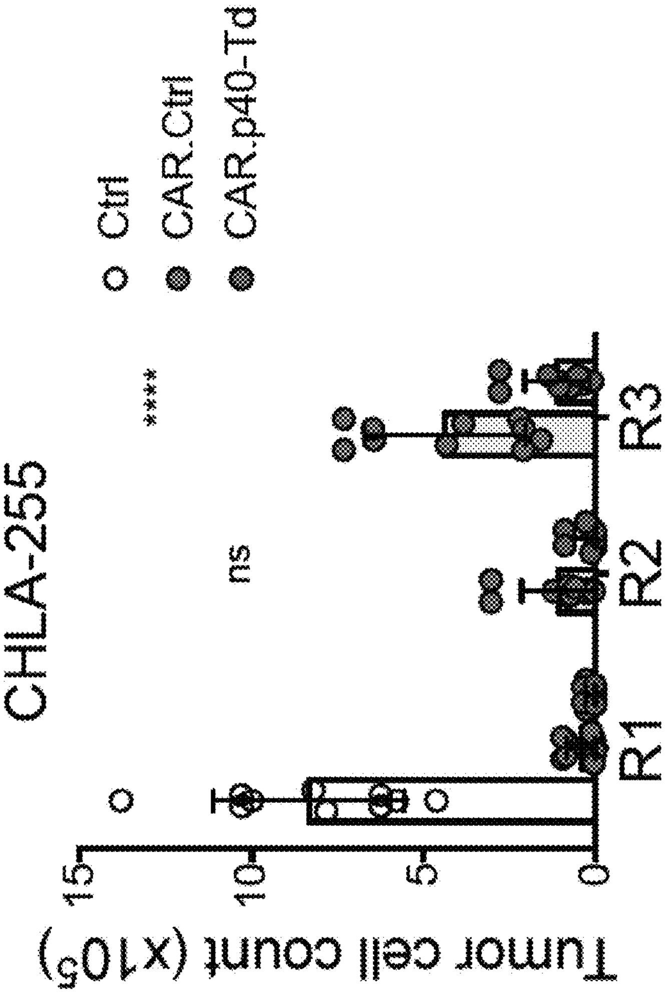
Figure 3A:
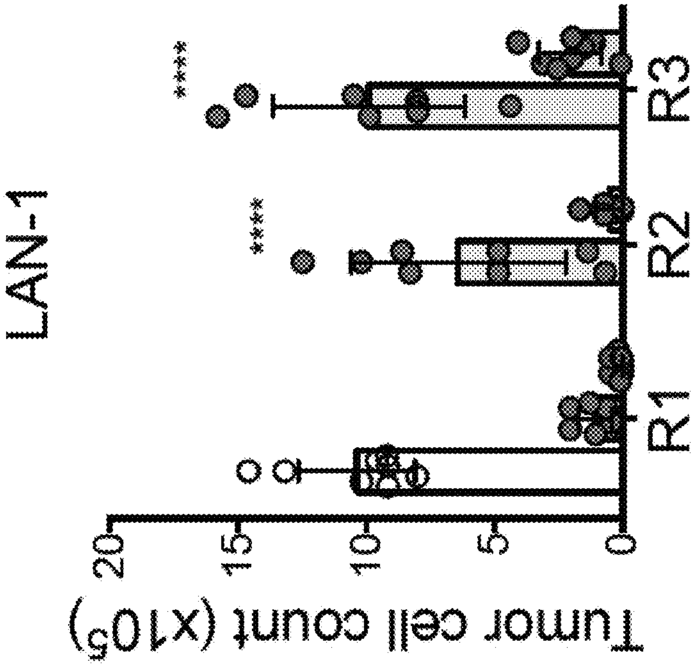
FIGS. 3A-3P demonstrate that p40 expression enhances the anti-tumor activity of CAR T cells in a neuroblastoma model.
Figure 3C:
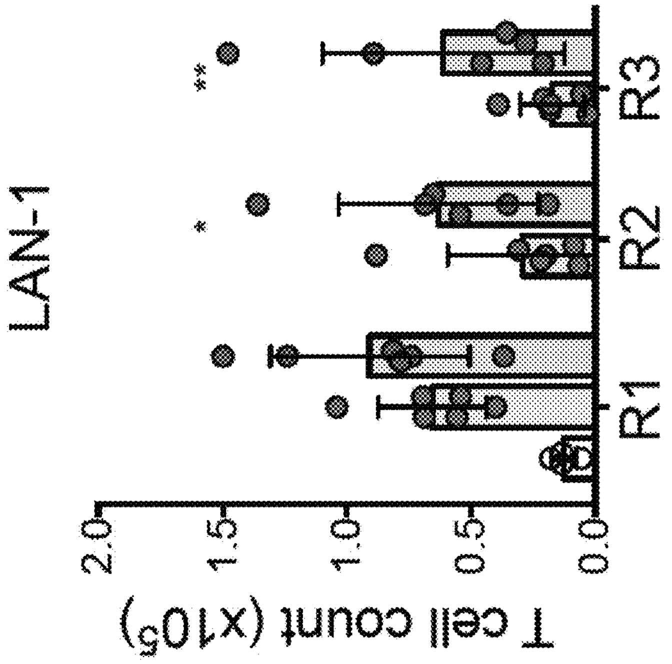
FIGS. 3C-3D provide T cell counts after each round of repetitive coculture illustrated in FIGS. 3A-3**B. Data shown as individual values and mean±SD (n=8). *p=0.03 for LAN1 R2; p=0.0049 for LAN1 R3; *p=0.0003 for CHLA-255 R2; p=0.0091 for CHLA-255 R3 determined by repeated measure 2-way ANOVA with Sidak post hoc test.
Figure 3D:
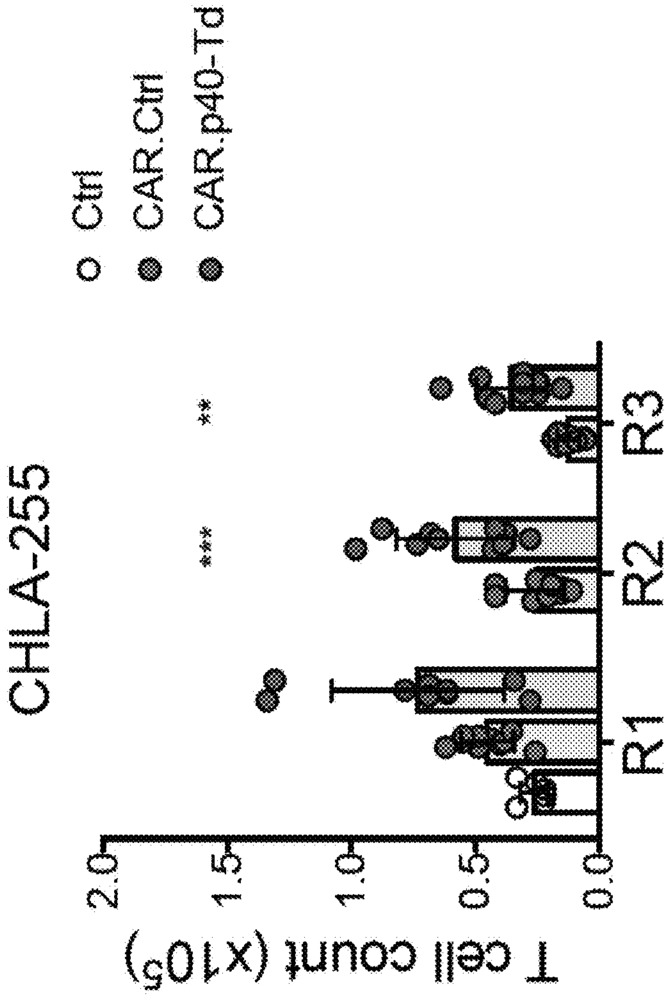
Figure 3E:
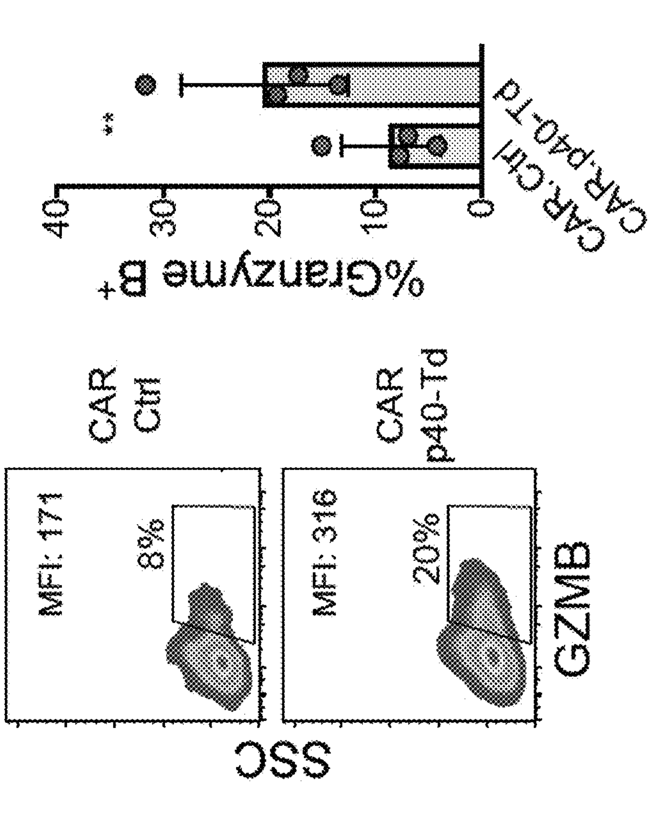
FIG. 3E shows intracellular staining of granzyme B of CAR.Ctrl cells and CAR.p40-Td cells at the end of R1. Data shown as individual values and mean±SD (n=3). p=0.0052 determined by paired t test.
Figure 3F:
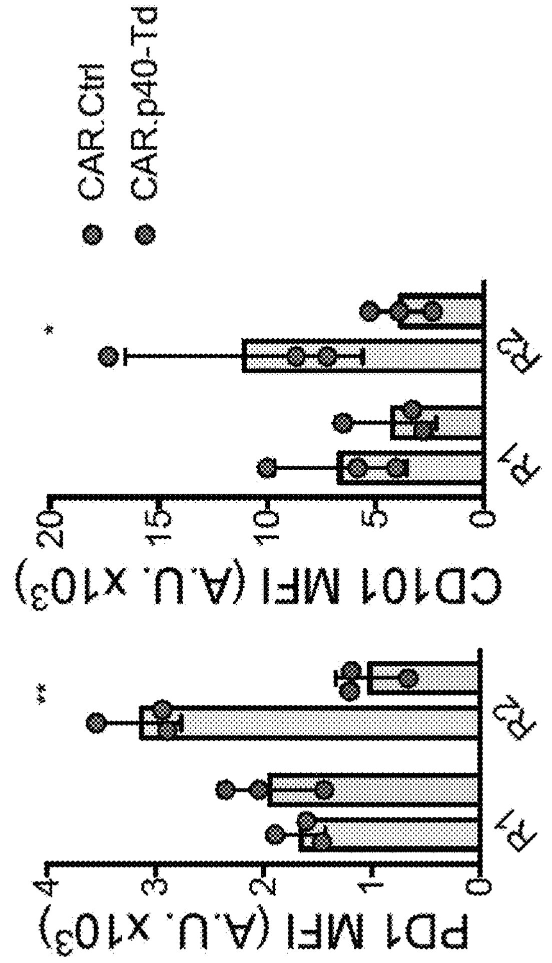
FIG. 3F shows expression of PD1 and CD101 in CAR.Ctrl cells and CAR.p40-Td cells after R1 and R2 of repetitive coculture with LAN-1 tumor cells. Data shown as individual values and mean±SD (n=3). **p=0.0014 for PD1 R2; *p=0.0365 for CD101 R2.
Figure 3G:
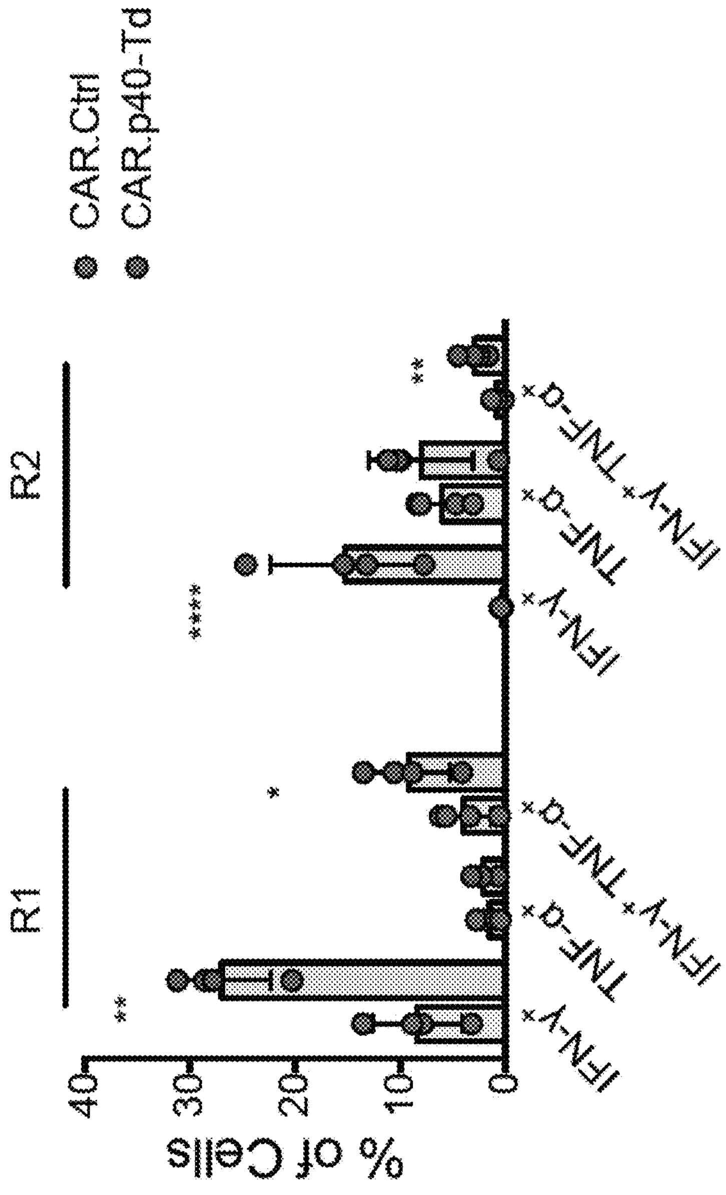
FIG. 3G shows intracellular staining of IFN-γ and TNF-α of CAR.C-trl cells and CAR.p40-Td cells at the end of R1 and R2 of coculture with LAN1 tumor cells. Data shown as individual values and mean±SD (n=3). **p=0.002 for IFN-$\gamma^+$ cells at R1; *p=0.0409 for IFN-$\gamma^+$ TNF-$\alpha^+$ cells at R1; **p<0.0001 for IFN-$\gamma^+$ cells at R2; p=0.009 for IFN-$\gamma^+$ TNF-$\alpha^+$ cells at R2 determined by repeated measure 2-way ANOVA with Sidak post hoc test.
Figure 3H:
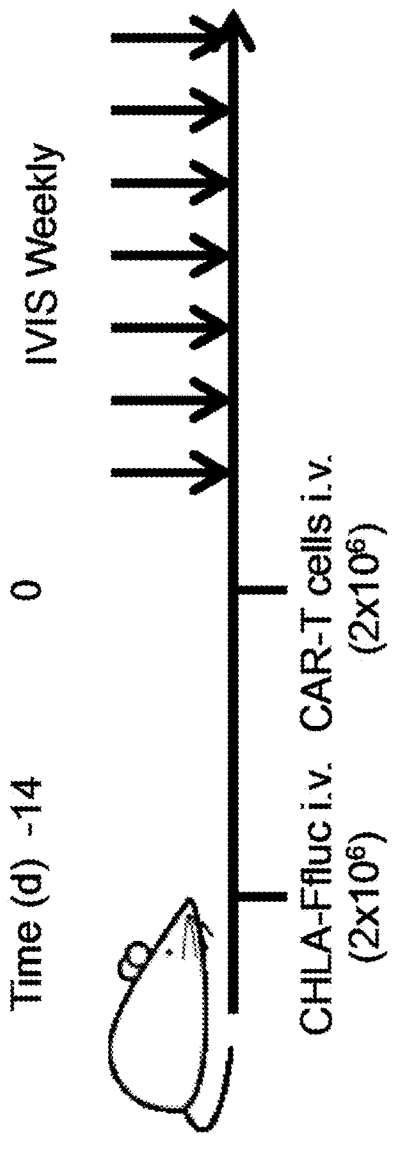
FIG. 3H provides a schematic representation of the metastatic neuroblastoma xenograft model.
Figure 3I:
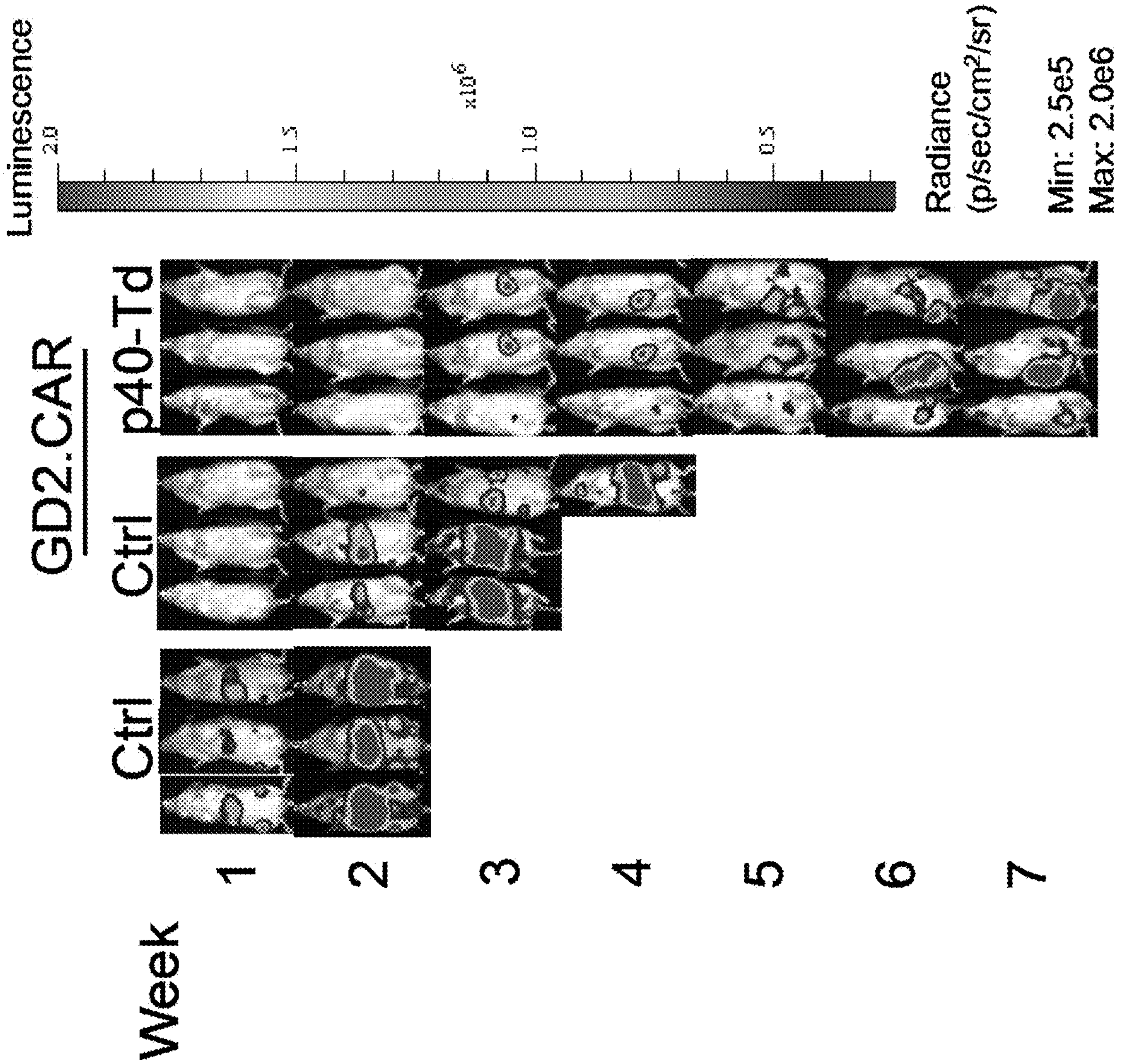
FIG. 3I shows representative tumor bioluminescence (BLI) of 2 independent experiments (n=8 mice/group).
Figure 3J:
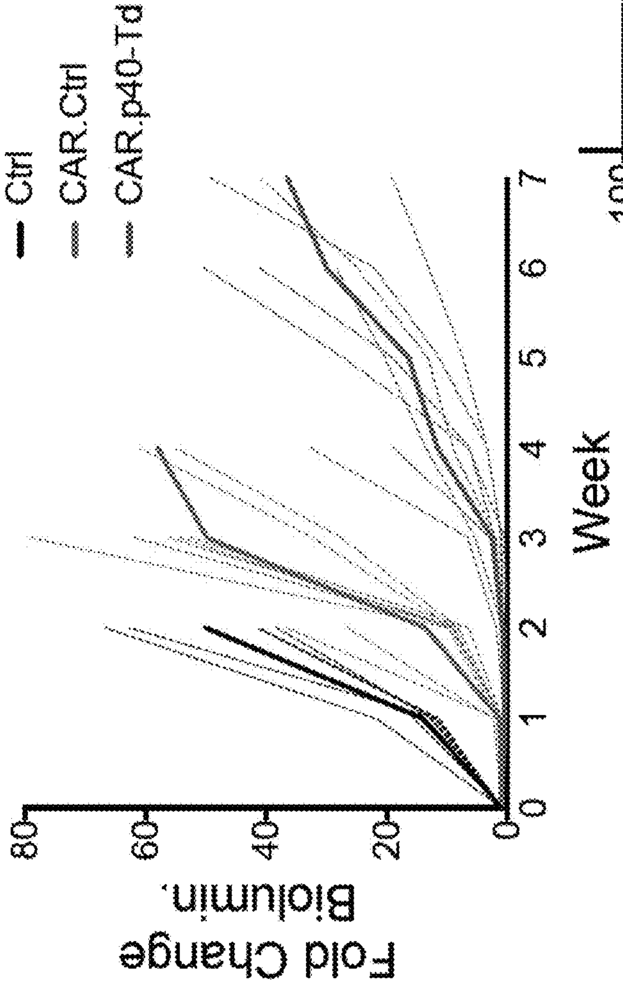
FIG. 3J shows kinetics of tumor BLI of 2 independent experiments (n=8 mice/group). Solid lines delineate mean fold change over time, while dashed lines indicate data of each individual mouse.
Figure 3K:
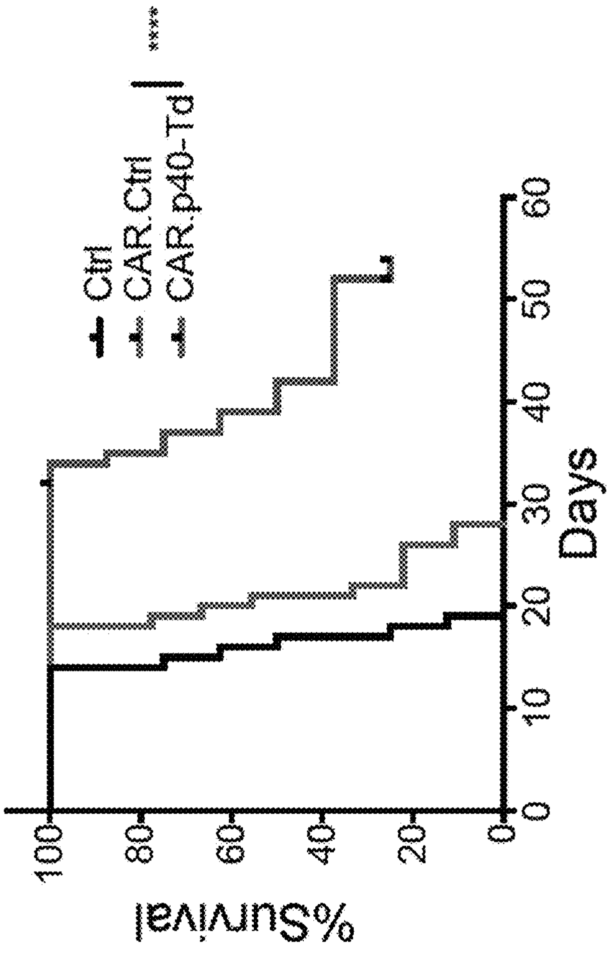
FIG. 3K shows Kaplan-Meier survival curve summarizing 2 independent experiments (n=8 mice/group).
Figure 3L:
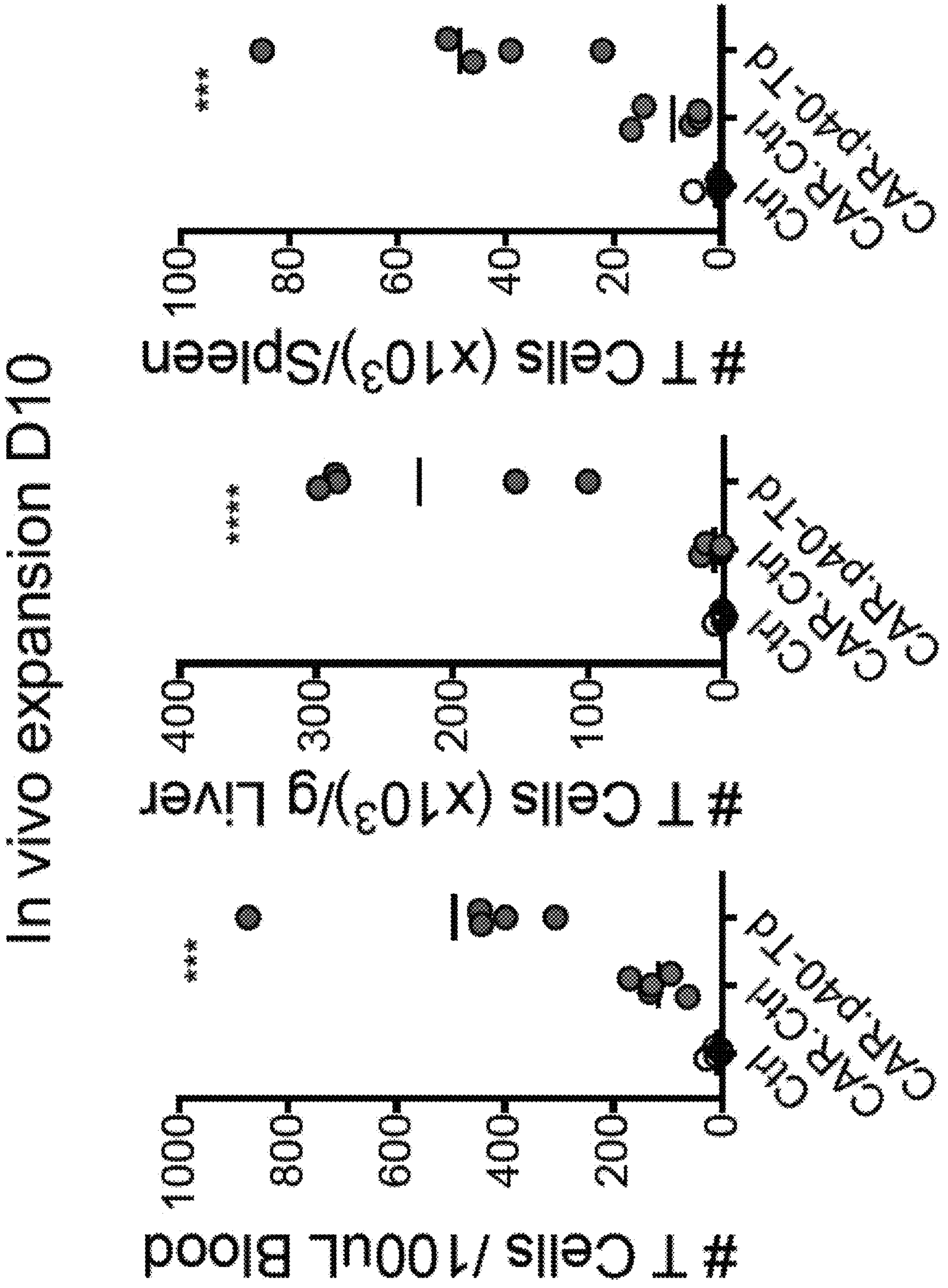
FIG. 3L shows frequency of human $CD3^+CD45^+$ cells in blood, spleen and liver collected 10 days post T cell infusion. Data shown as individual values, mean±SD (n=5 mice/group) and are representative of 2 experiments. *p=0.0006 for blood; **p<0.0001 for liver and p=0.0007 for spleen determined by 1-way ANOVA with Sidak post hoc test.
Figure 3M:
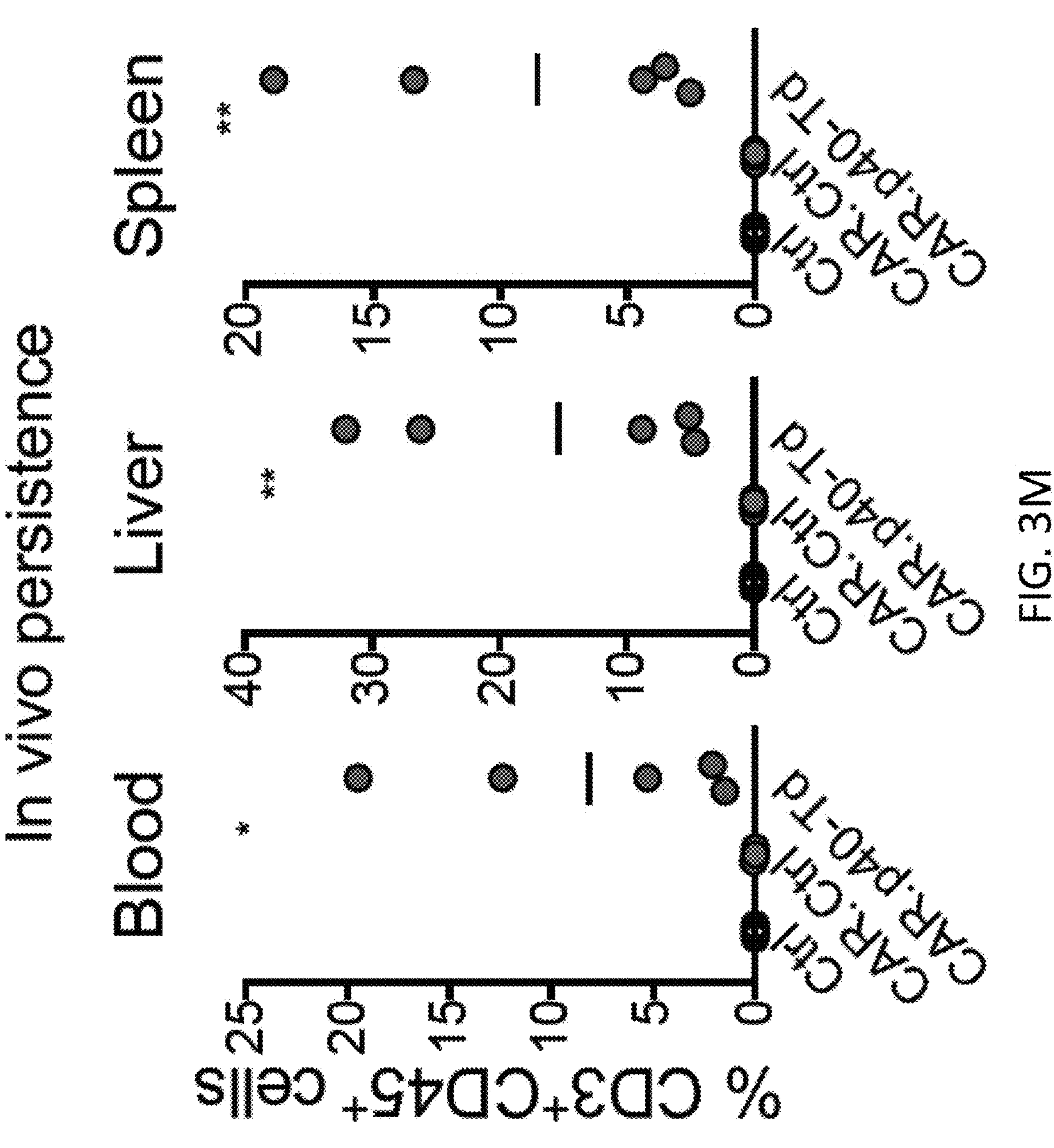
FIG. 3M shows frequency of human $CD3^+CD45^+$ cells in blood, spleen and liver collected at the time of mouse euthanasia. Data shown as individual values, mean±SD (n=5 mice/group) and are representative of 2 experiments. *p=0.0132 for blood; **p<0.0067 for liver and p=0.0071 for spleen determined by 1-way ANOVA with Sidak post hoc test.
Figure 3N:
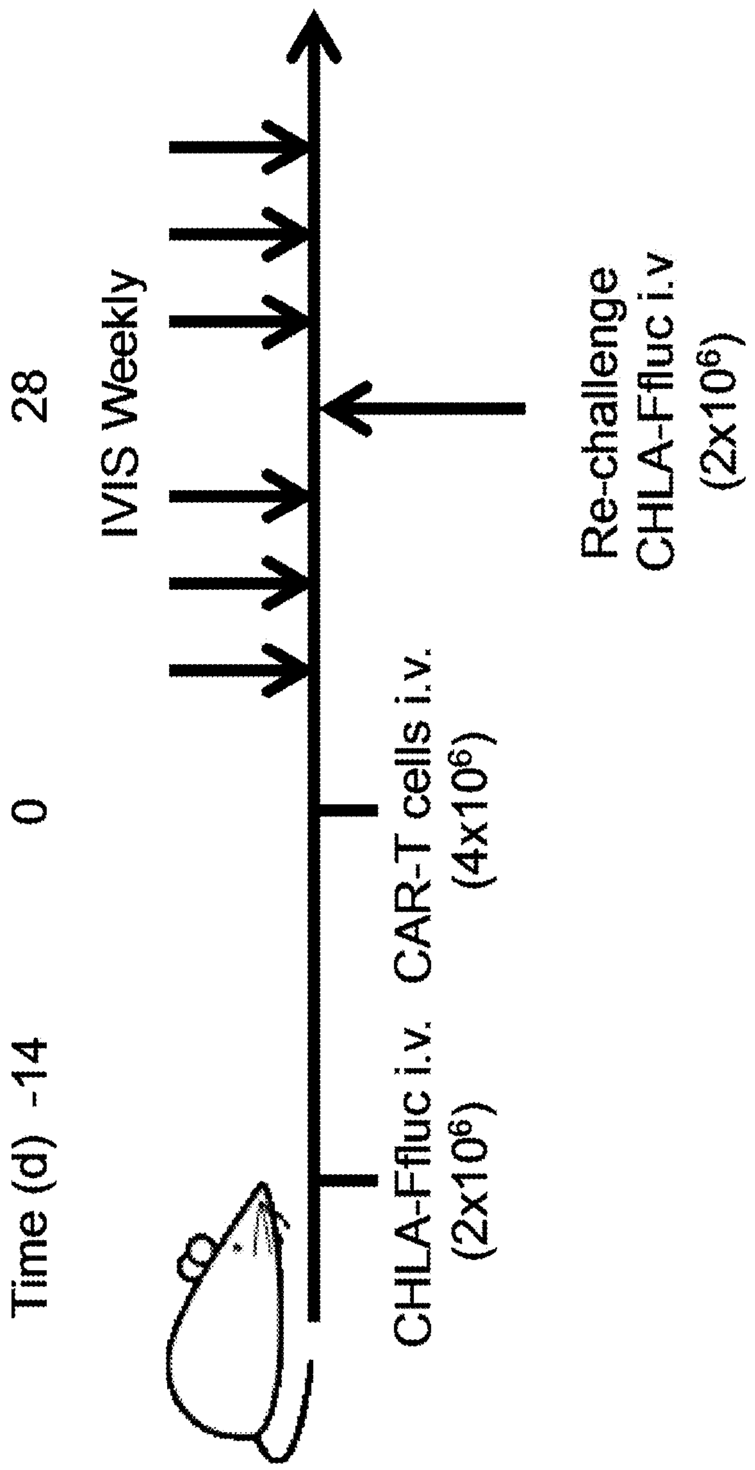
FIG. 3N provides a schematic representation of the metastatic neuroblastoma xenograft model and tumor rechallenge.
Figure 30:
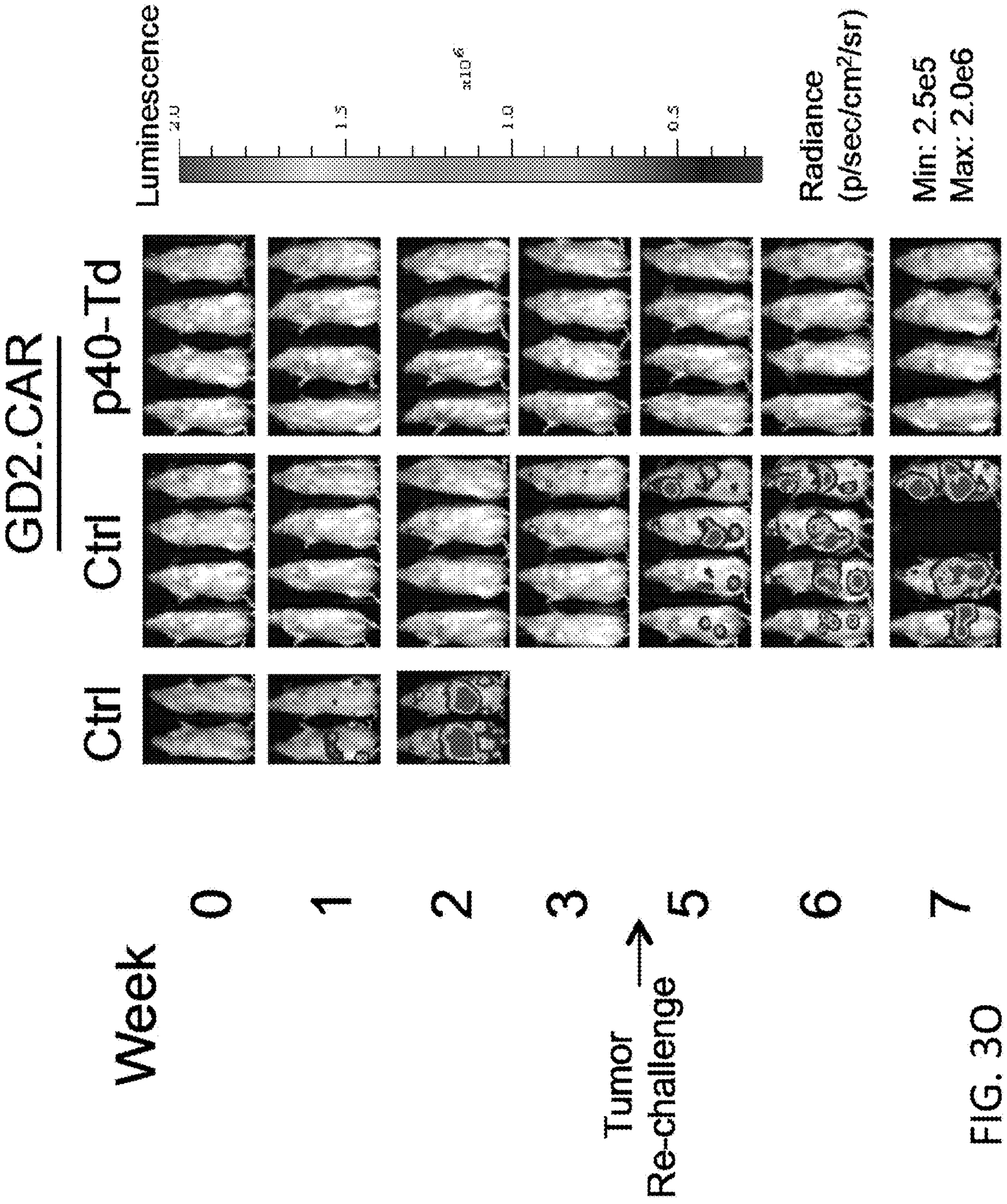
Figure 3P:
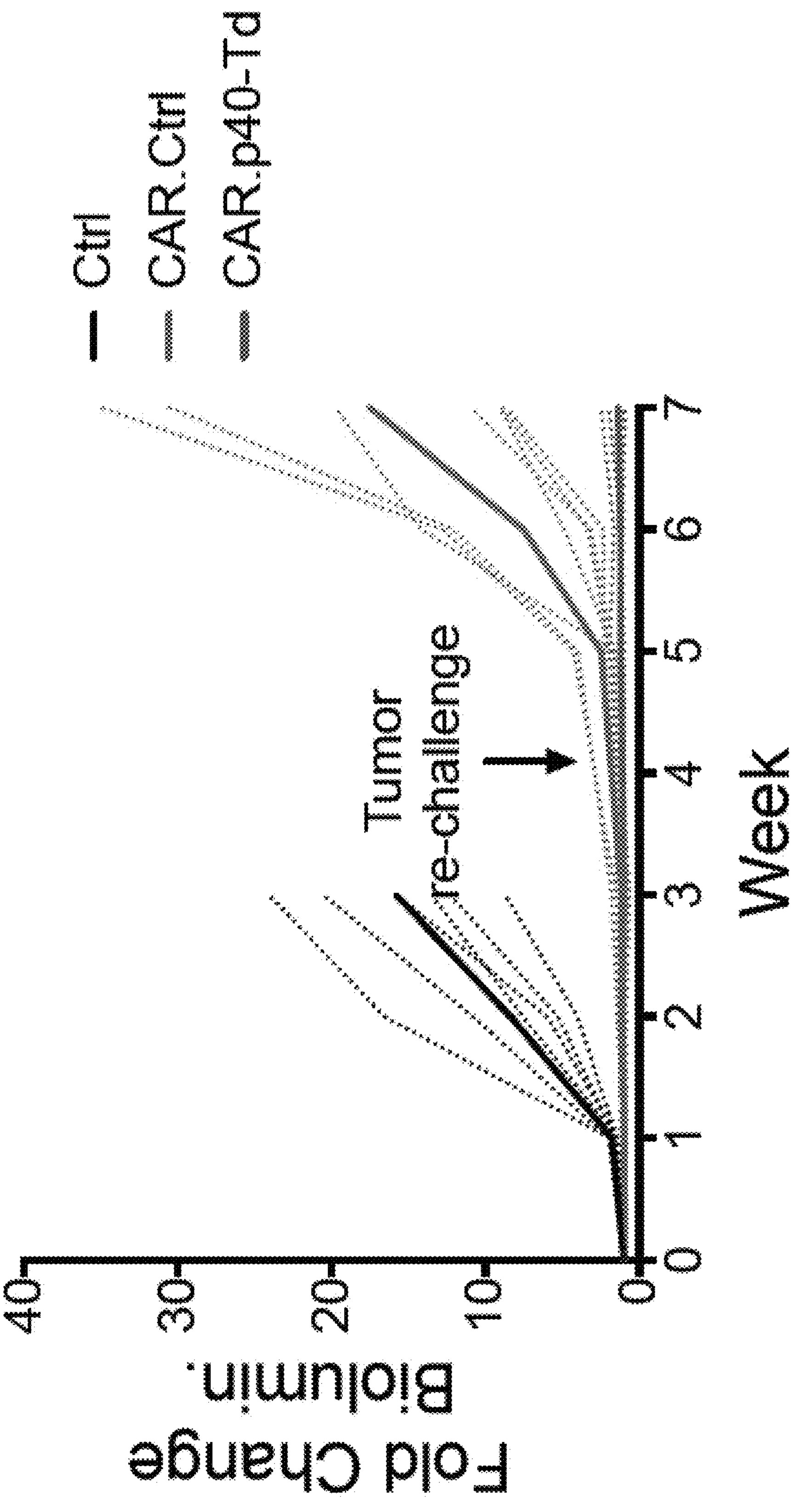
Figure 4A:
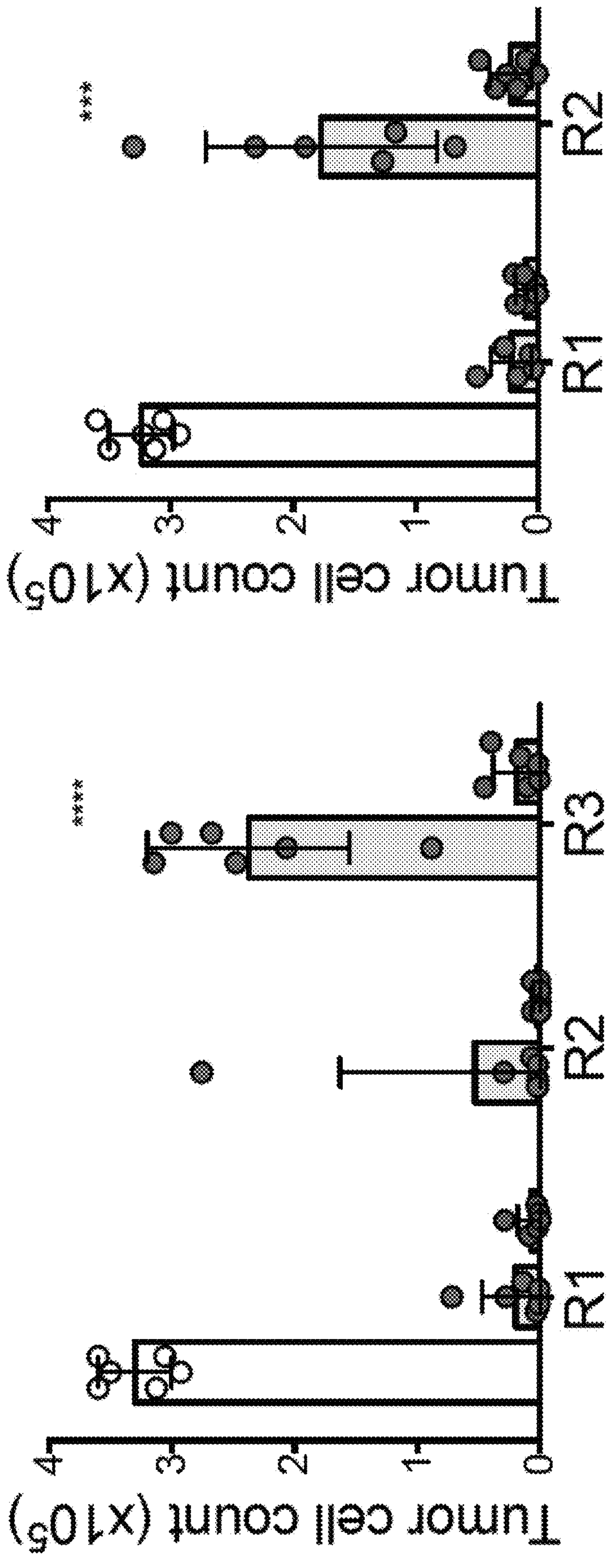
FIGS. 4A-4G demonstrate that p40 expression enhances the anti-tumor activity of CAR T cells in a pancreatic cancer model.
Figure 4B:
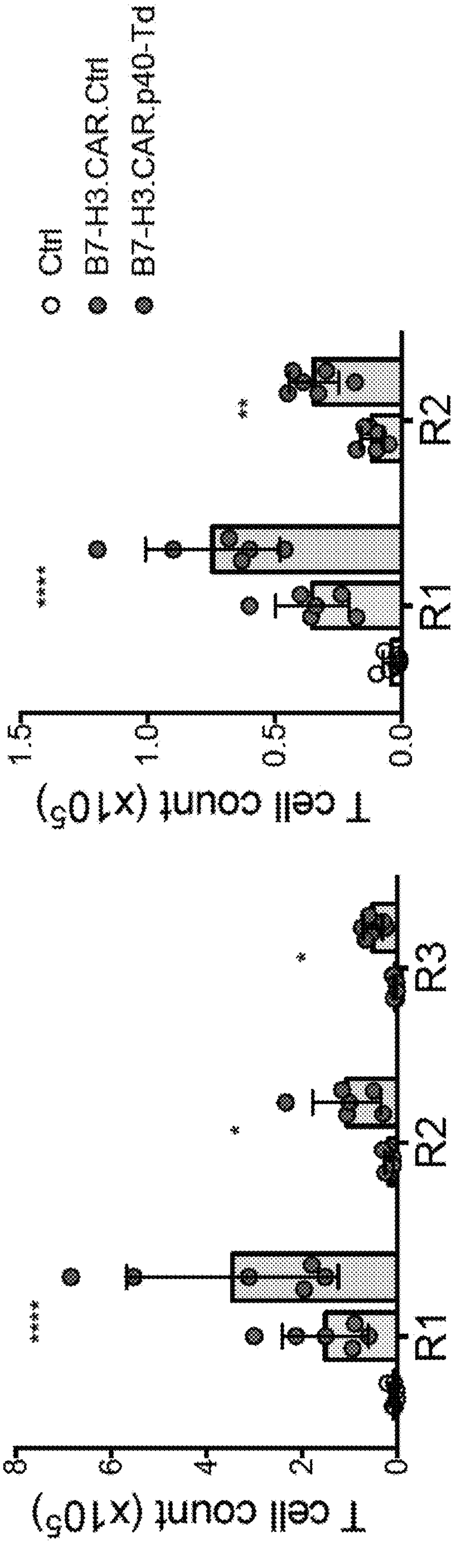
Figure 4C:
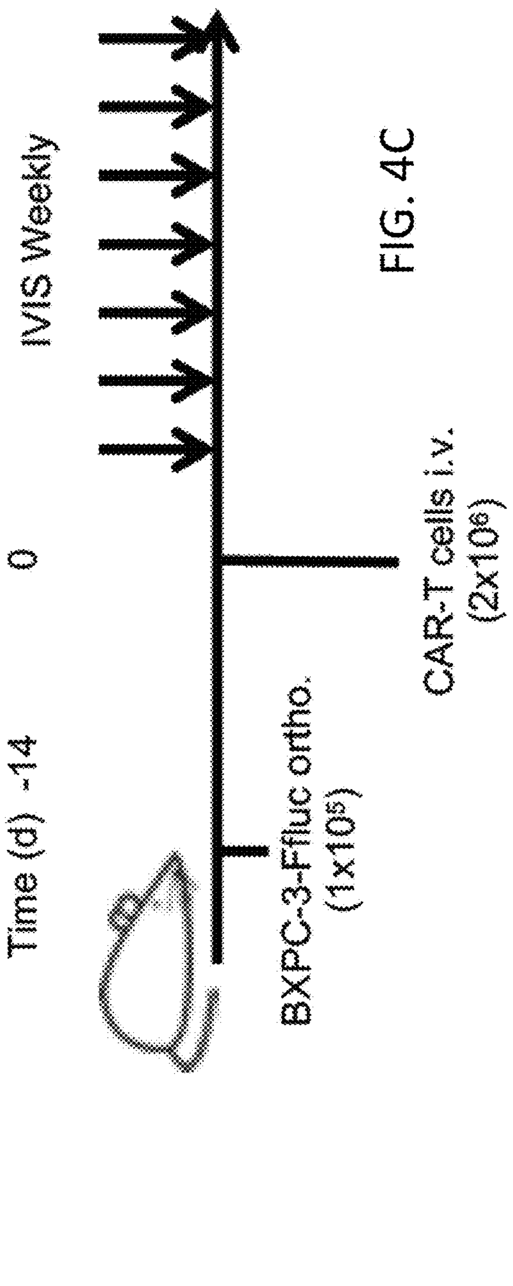
Figure 4D:
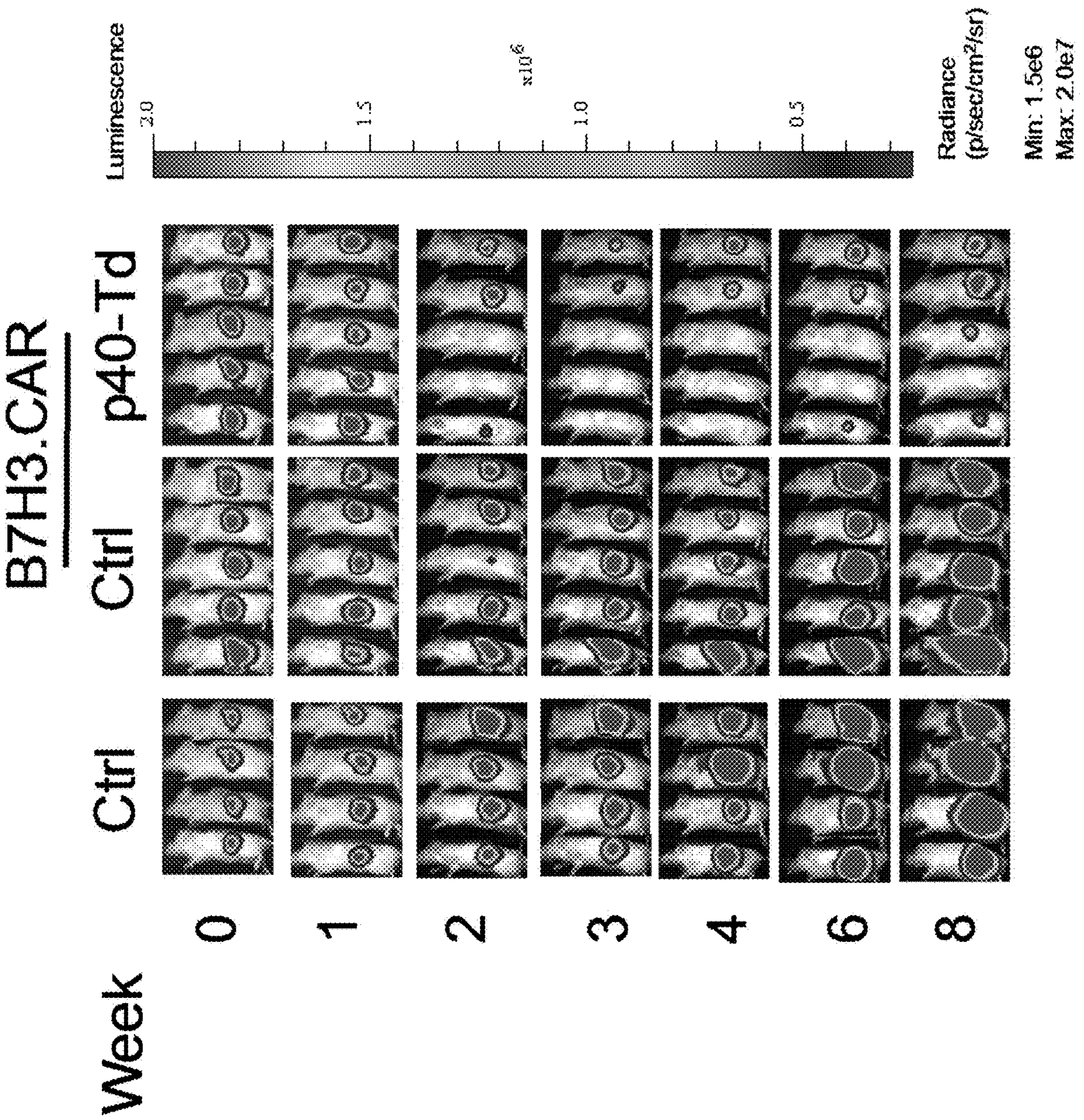
Figure 4E:
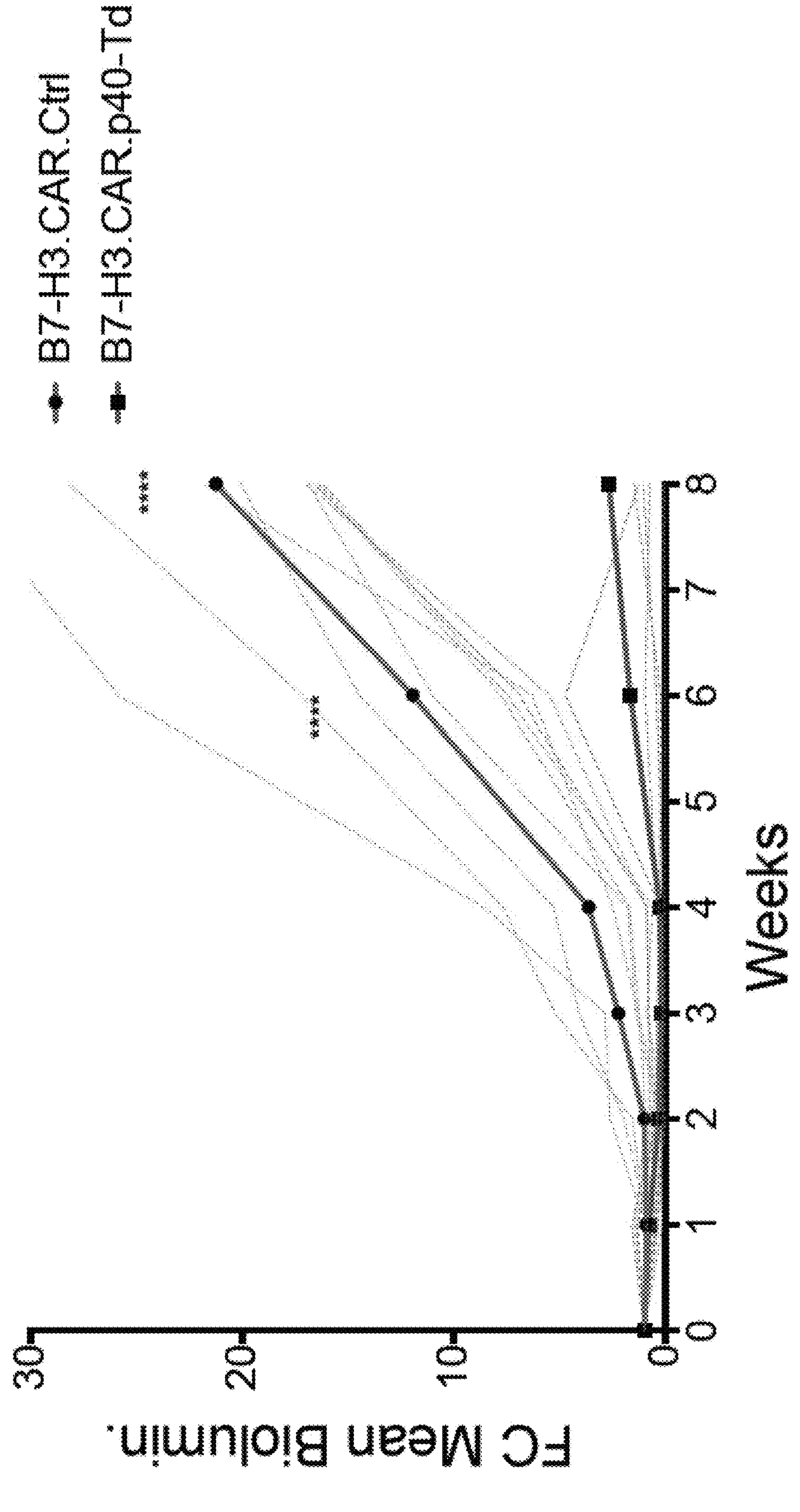
Figure 4F:
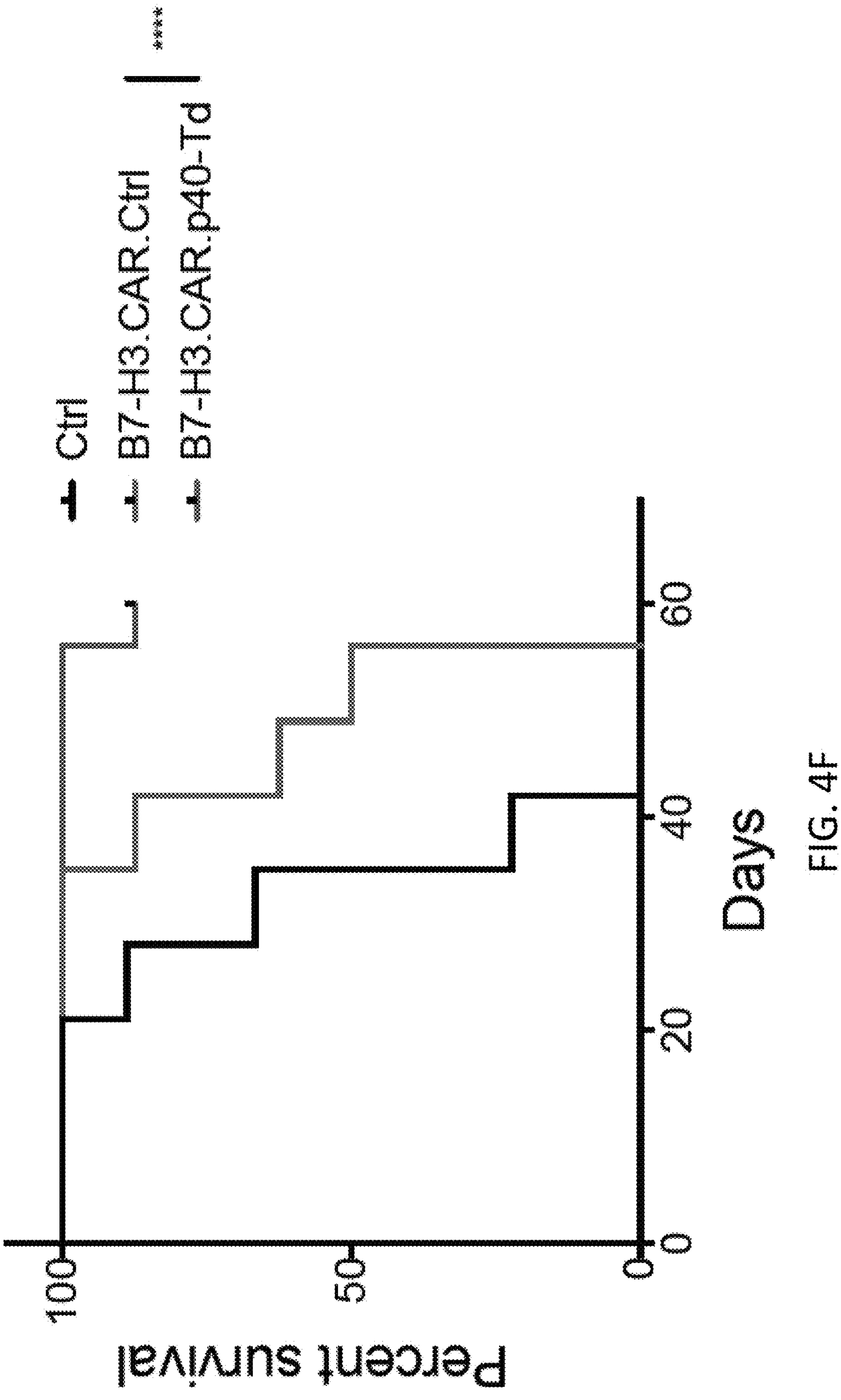
Figure 4G:
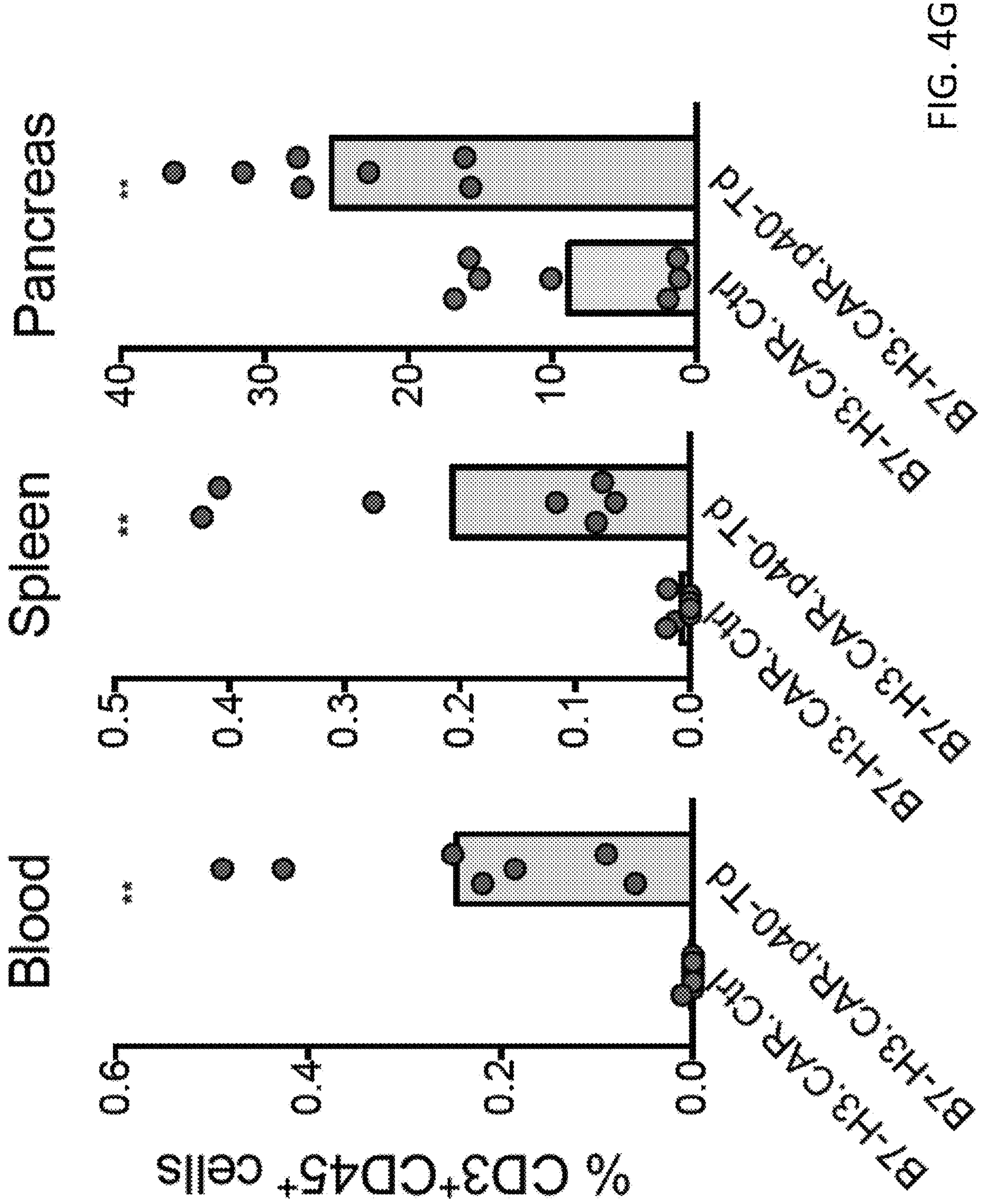
Figure 9A:
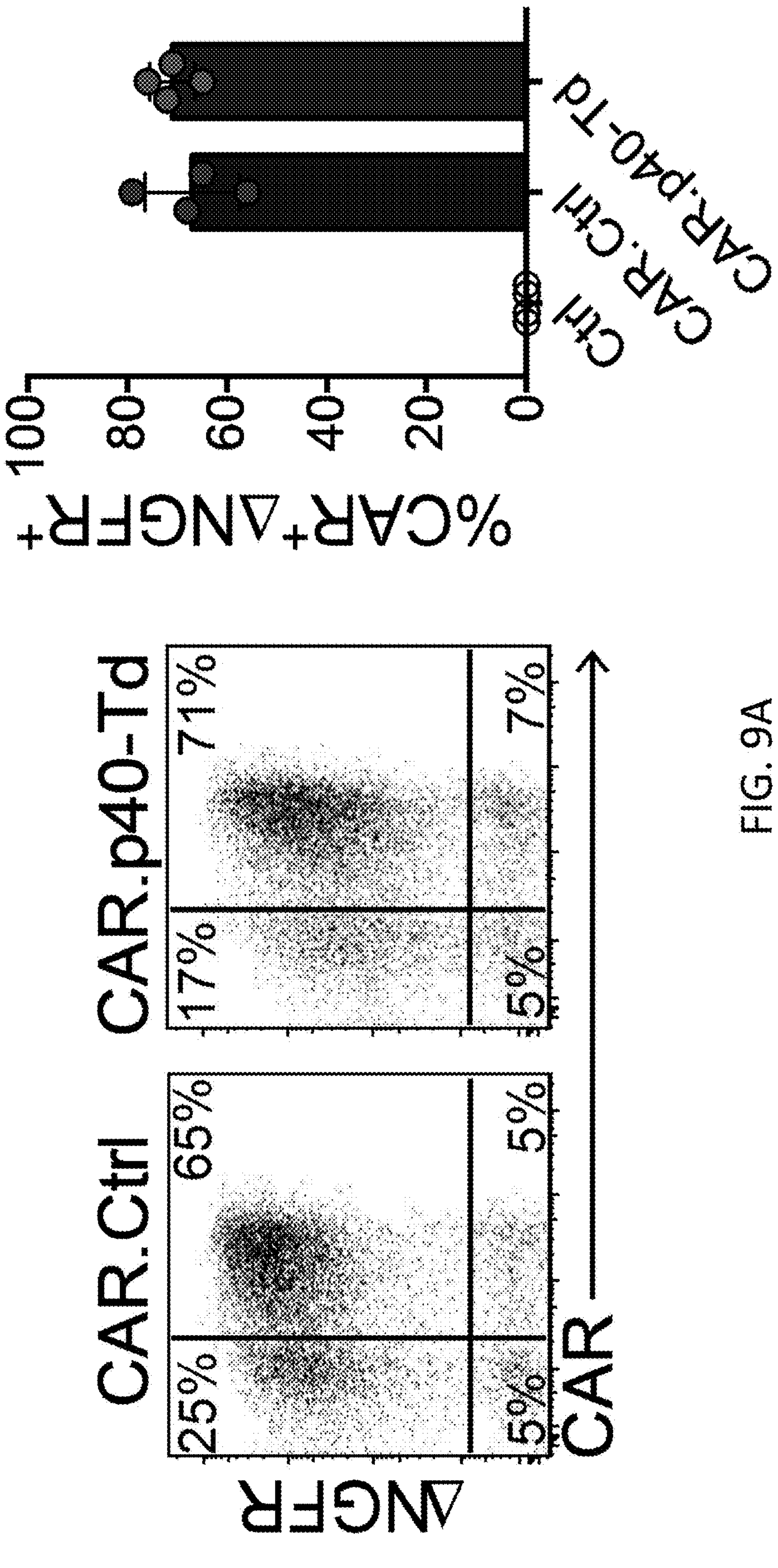
FIGS. 9A-9E demonstrate that p40 expression enhances the anti-tumor activity of CAR T cells in neuroblastoma.
Figure 9C:
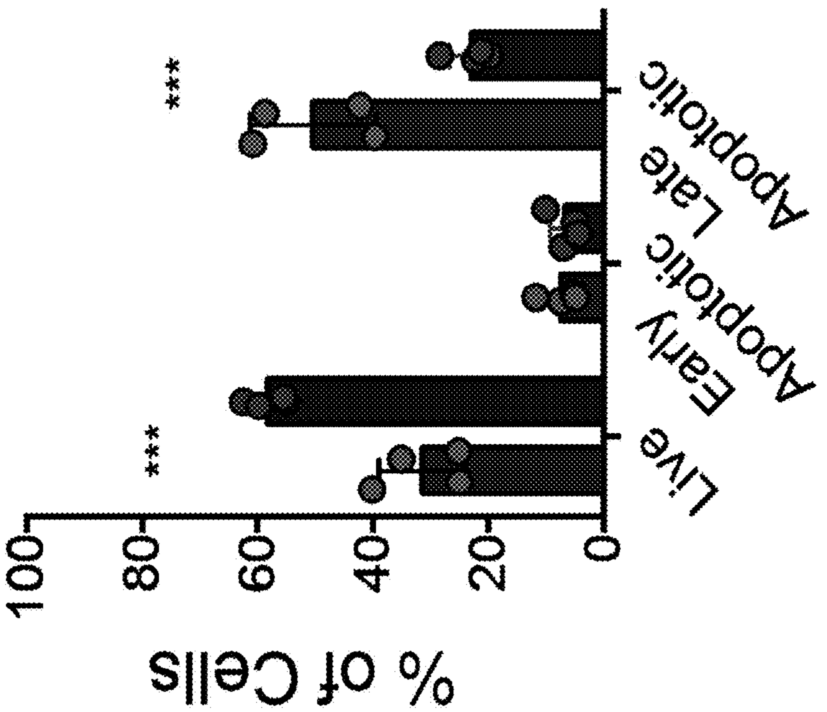
Figure 9B:
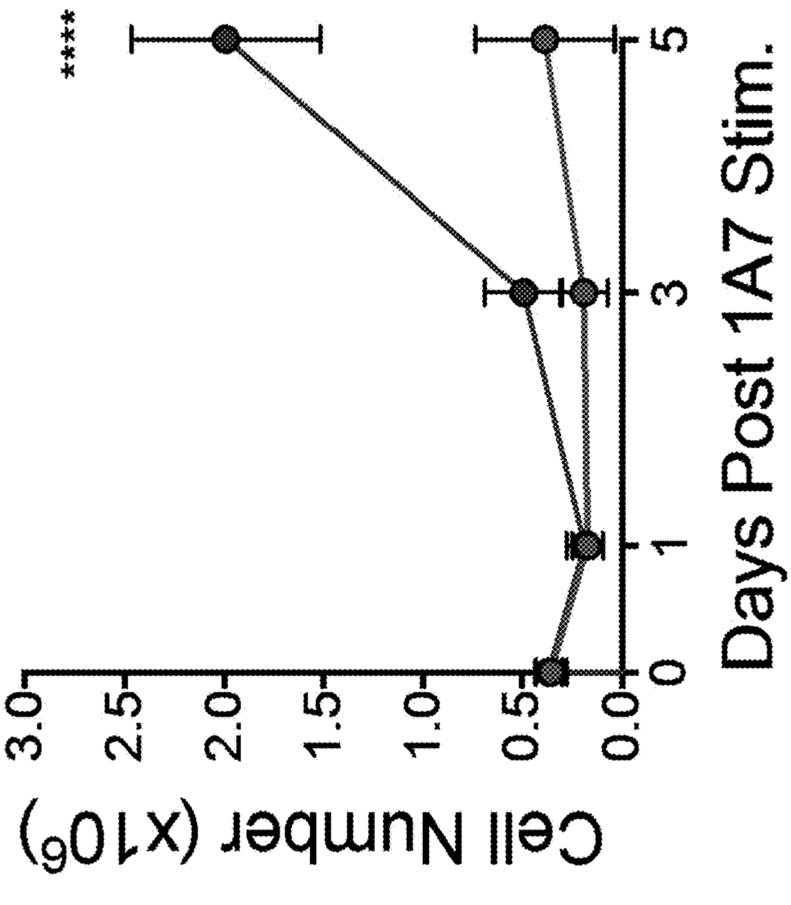
Figure 9D:
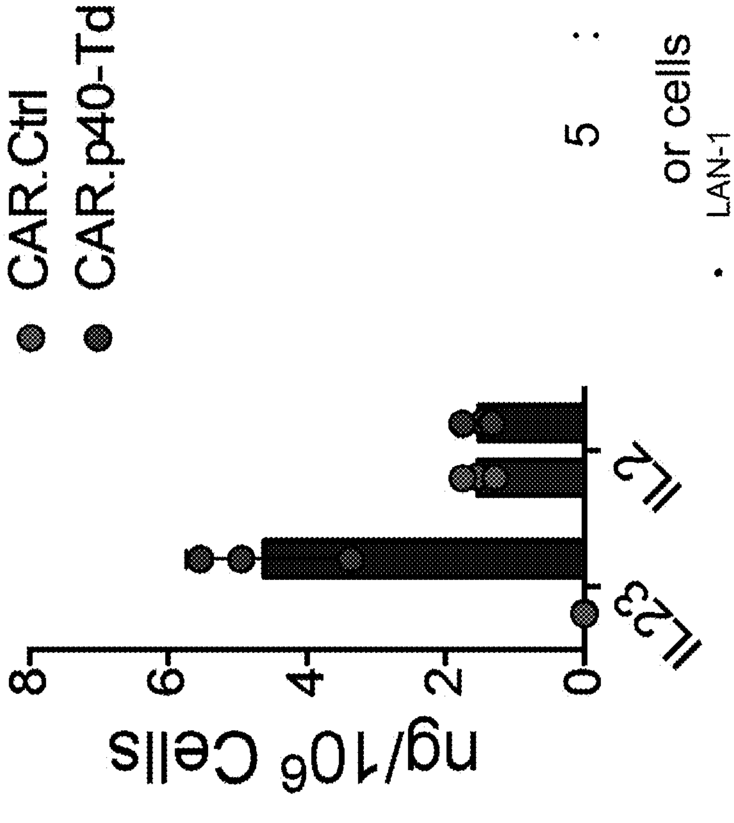
Figure 9E:
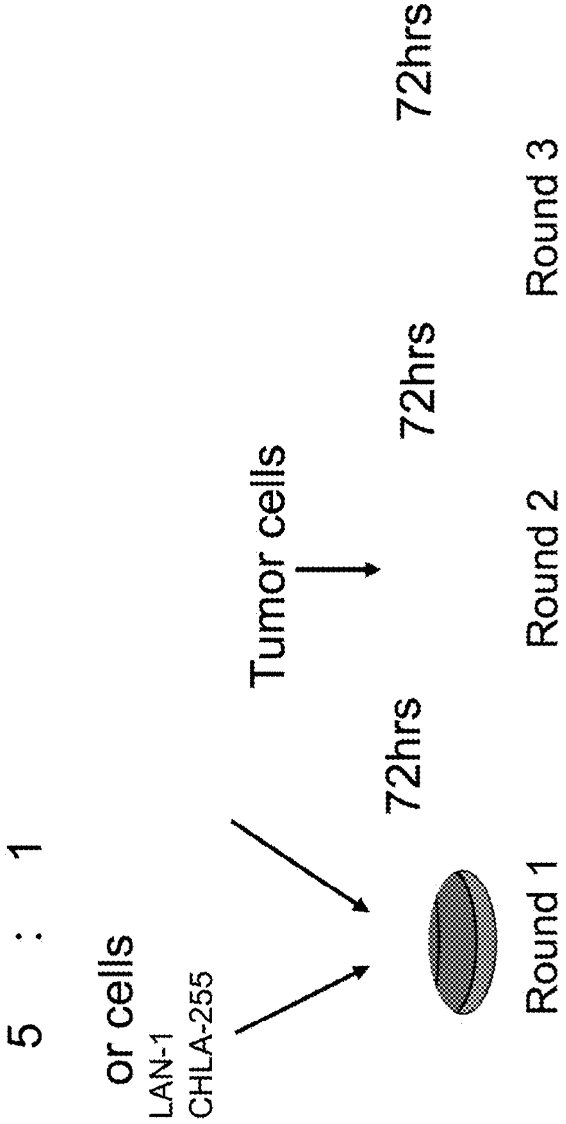

Whether IL23 p40 expression in CAR T cells improves their antitumor activity was assessed. p40 was expressed in CAR T cells (CAR.p40-Td) targeting the GD2 antigen expressed in neuroblastoma (NB) (FIG. 9A). CAR.p40-Td cells showed robust expansion (FIG. 9B) and reduced apoptosis (FIG. 9C) when stimulated in vitro with an anti-idiotype antibody that crosslinks the CAR [24], as compared to control CAR T cells (CAR.Ctrl cells). IL23 was only detected in activated CAR.p40-Td cells, while IL2 secretion remained unchanged (FIG. 9D). The anti-tumor effects of CAR T cells in vitro was assessed using repetitive tumor co-culture assays in which human NB cell lines (LAN-1 or CHLA-255) were used at high tumor to T cell ratio (FIG. 9E). In this stress culture condition test, CAR.Ctrl cells failed to control tumor growth after the first/second round of co-culture, while CAR.p40-Td cells remain effective (FIGS. 3A-3B). In parallel, the number of CAR.Ctrl cells gradually reduced after each round of co-culture, while CAR.p40-Td cells persisted (FIGS. 3C-3D). In addition to enhanced proliferation, the CAR.p40-Td cells showed superior effector functions at individual cell level. Specifically, CAR.p40-Td cells expressed higher level (percentage and MFI) of the lytic enzyme granzyme B (FIG. 3E) and reduced expression of the exhaustion markers PD1 and CD101 [27] (FIG. 3F), as compared to CAR.Ctrl cells. In addition, after repeated stimulation, CAR.Ctrl cells underwent progressive reduction of T cells producing IFNγ and TNFα, an indicator of functional exhaustion [28], while CAR.p40-Td cells continued to produce IFNγ and TNFα (FIG. 3G). In a metastatic NB model in NOD/SCID/IL-2R$^{null}$ (NSG) mice, treated with suboptimal doses (2×10$^6$ cells) of CAR T cells, CAR.p40-Td cells promoted enhanced tumor control and improved survival as compared to CAR.Ctrl cells (FIGS. 3H-3K). Consistently, CAR.p40-Td cells showed superior initial expansion (day 10) in vivo in peripheral blood, spleen and liver (FIG. 3L), and prolonged persistence in the same organs at the time of euthanasia (FIG. 3M). When a higher dose (4×10$^6$ cells) of CAR T cells was used in tumor-bearing mice, both CAR.Ctrl cells and CAR.p40-Td cells promoted tumor regression (FIGS. 3N-3P), but only the mice receiving CAR.p40-Td cells were protected from tumor re-challenge 4 weeks after T cell treatment (FIGS. 3N-3P). The enhanced anti-tumor activity of CAR.p40-Td cells was confirmed in a pancreatic ductal adenocarcinoma (PDAC) model using CAR T cells targeting the B7-H3 antigen [29]. CAR.p40-Td cells showed superior anti-tumor effects and better persistence in stressed coculture condition against the human PDAC cell line BXPC-3 compared to CAR.Ctrl cells (FIGS. 4A-4B). Furthermore, in an orthotopic PDAC model using the BXPC-3 cell line that constitutively express high level of PD-L1 and is more resistant to CAR T cell effects [29], CAR.p40-Td cells showed superior anti-tumor effects and better persistence when compared to CAR.Ctrl cells (FIGS. 4C-4G). Therefore, p40 engineering of CAR T cells promotes anti-tumor activity sustaining T cell persistence and expansion.

Incorporation of p40 in Murine T Cell Promotes Local Effects of IL23 in Syngeneic Tumor Models of Melanoma and Pancreatic Cancer.

Figure 5B:
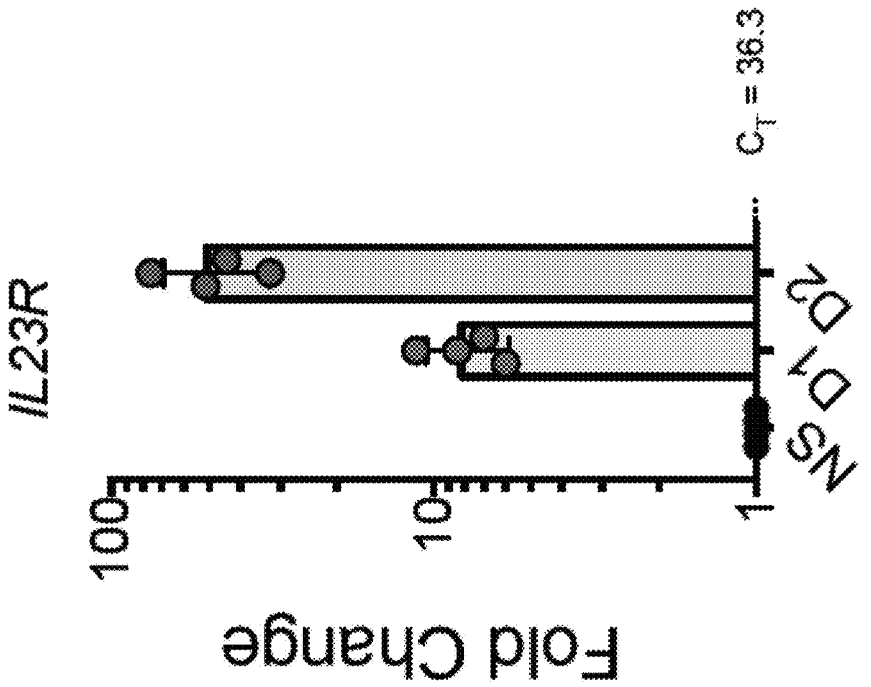
FIGS. 5A-5K demonstrate that p40 expression enhances the anti-tumor activity of T cells in syngeneic tumor models.
Figure 5A:
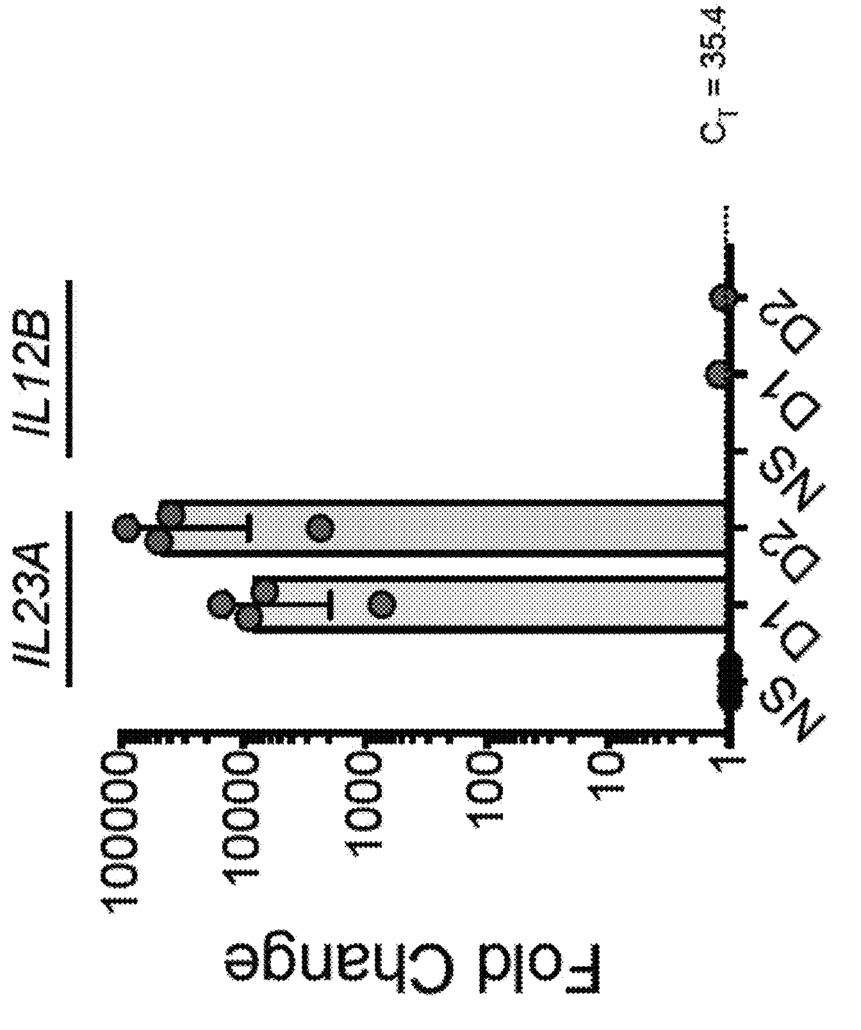
Figure 5C:
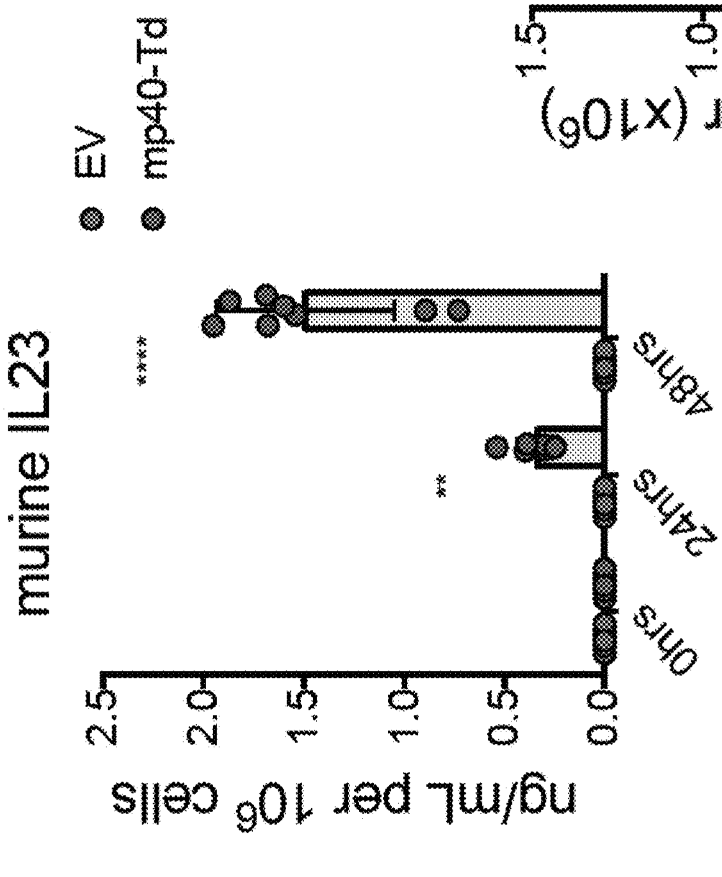
Figure 5D:
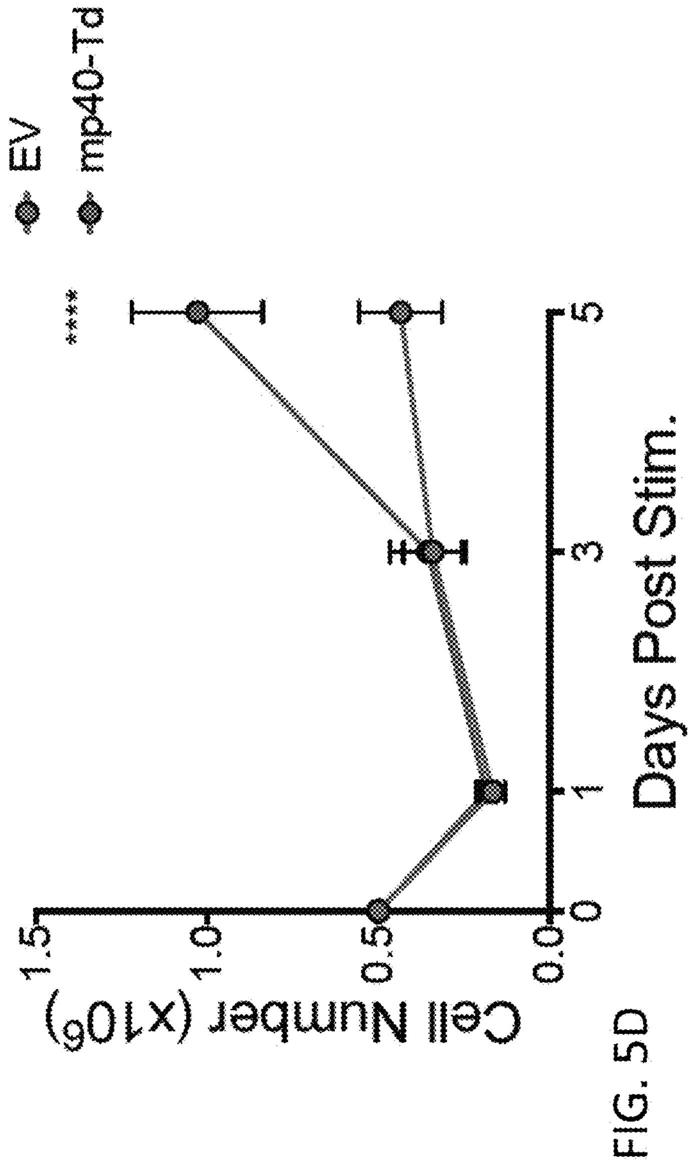
Figure 5E:
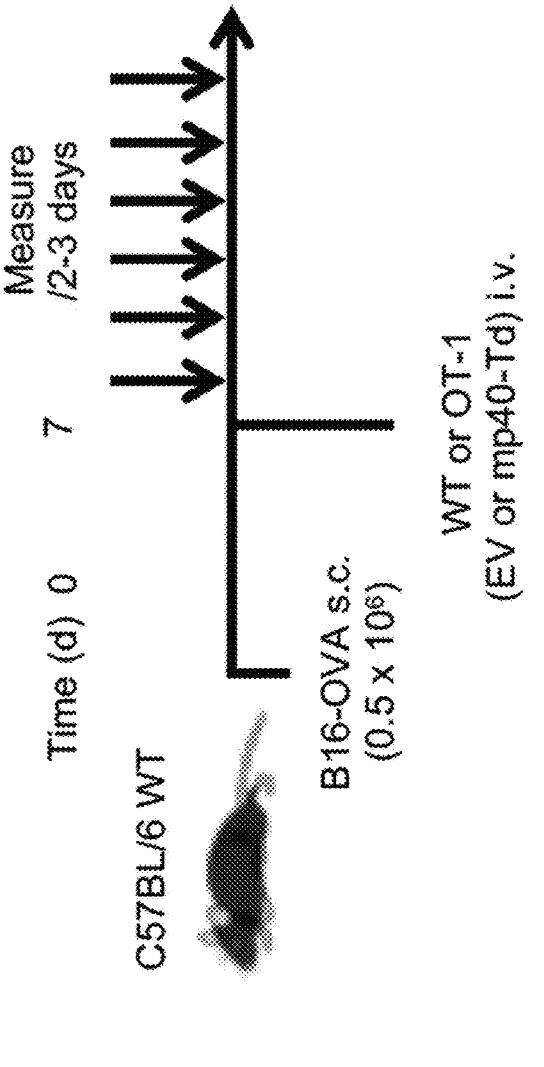
Figure 5F:
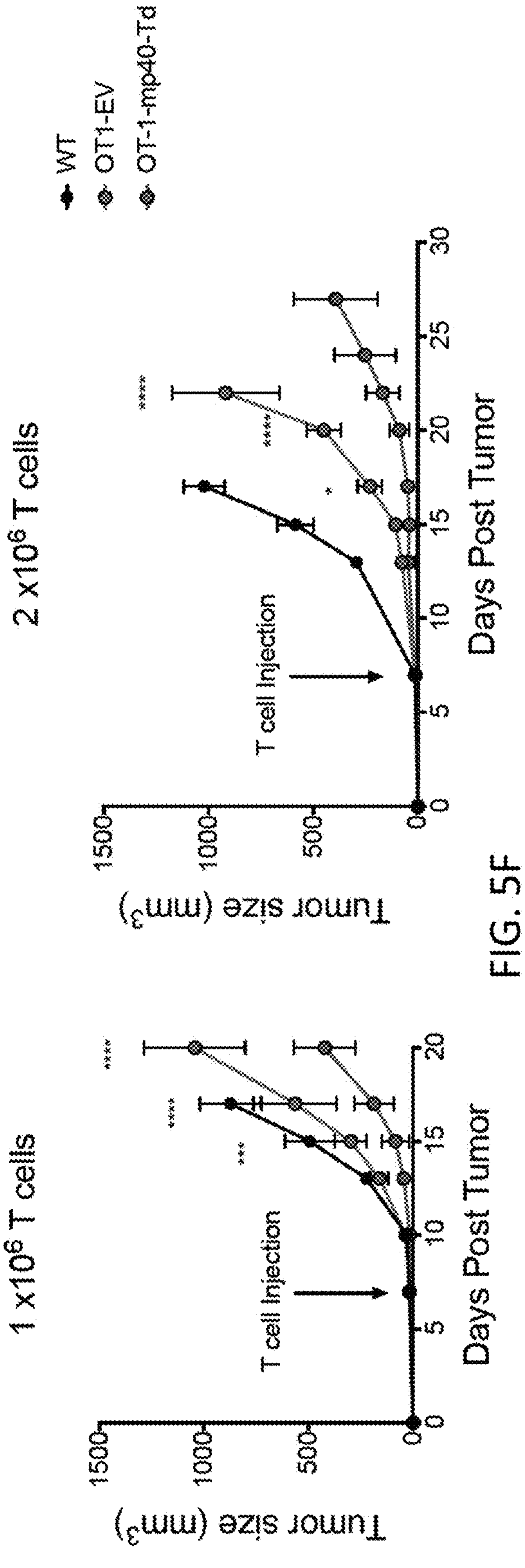
Figure 5H:
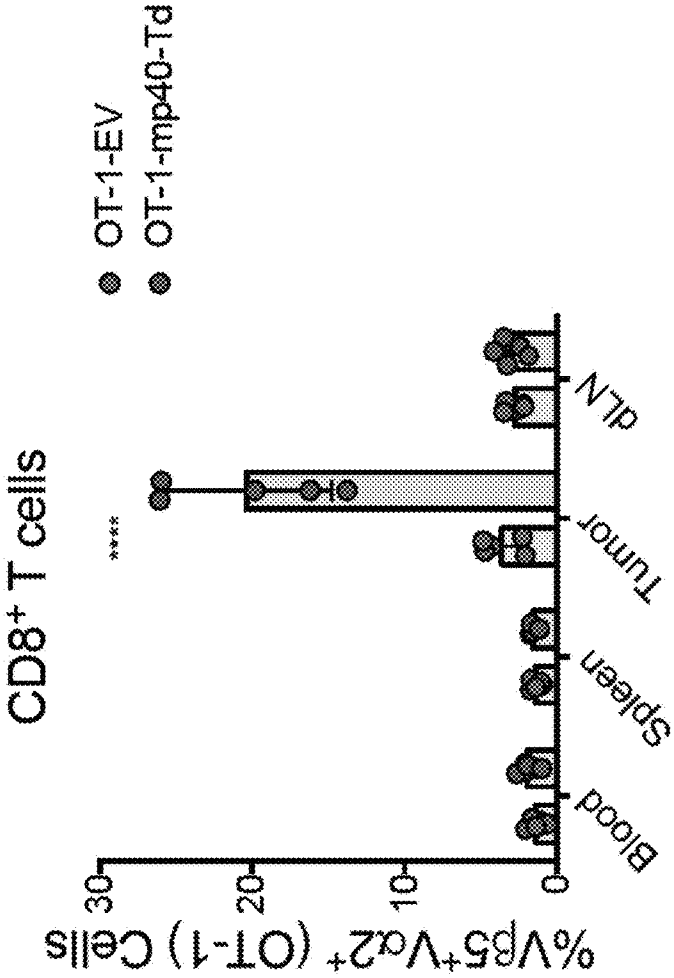
Figure 5G:
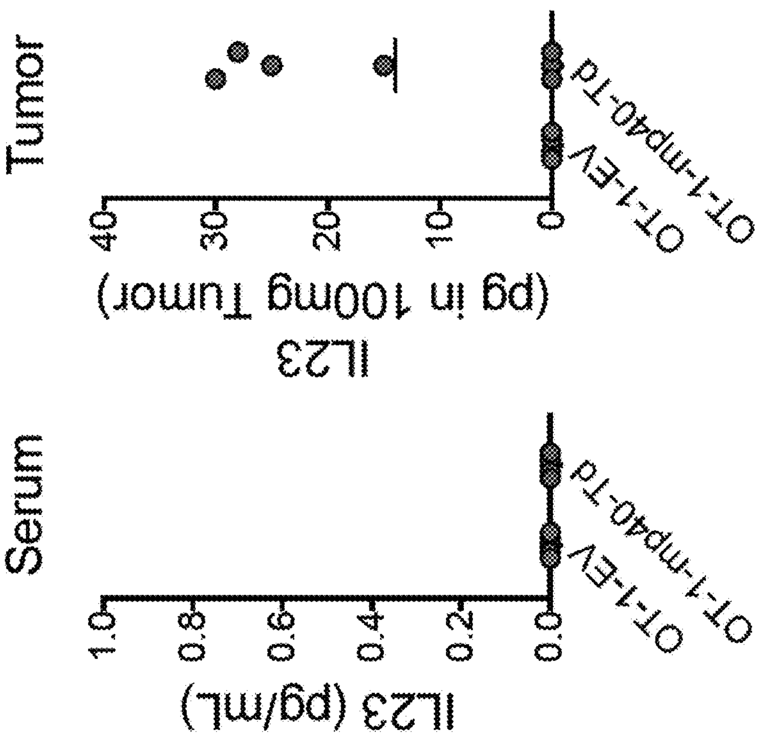
Figure 5I:
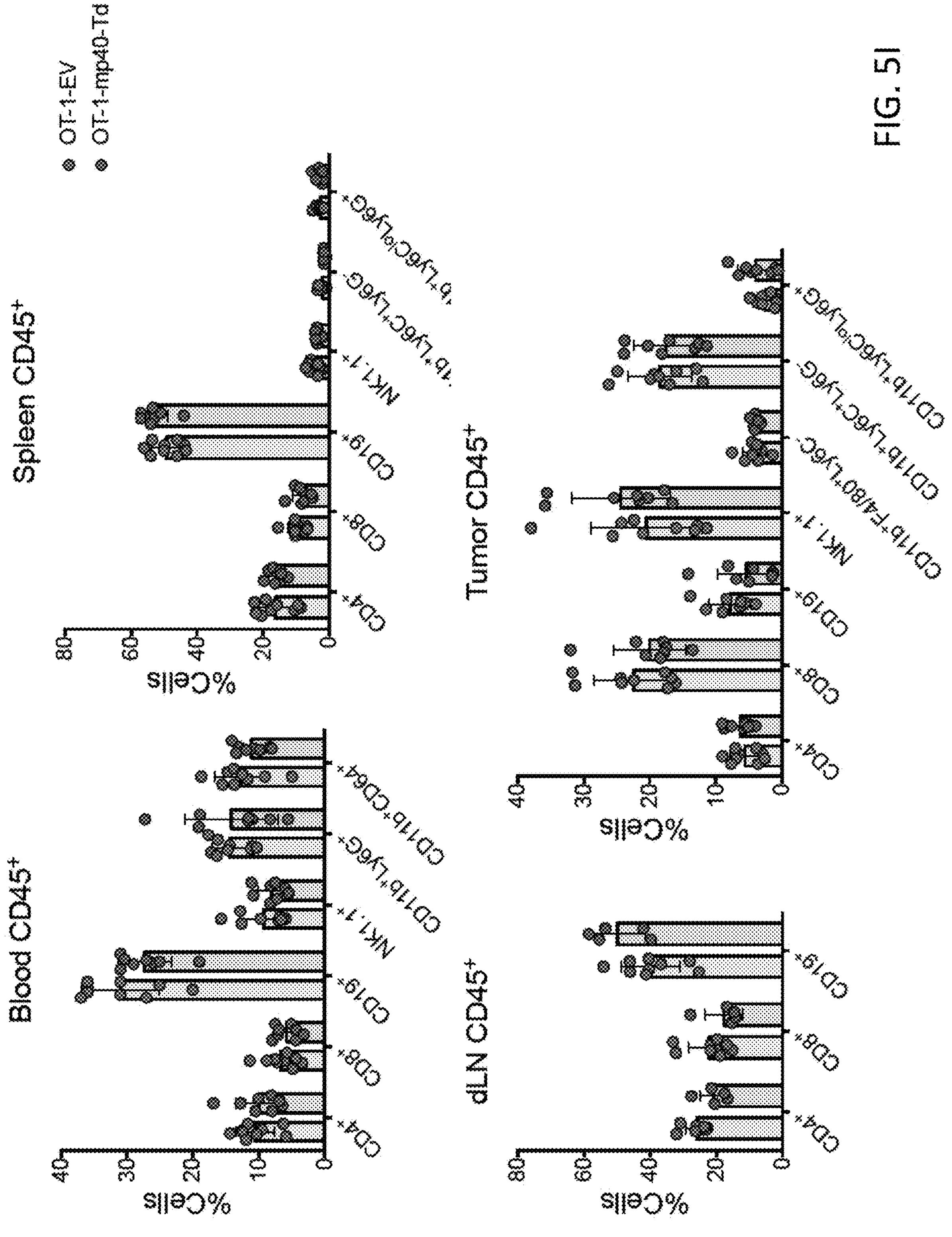
Figure 5J:
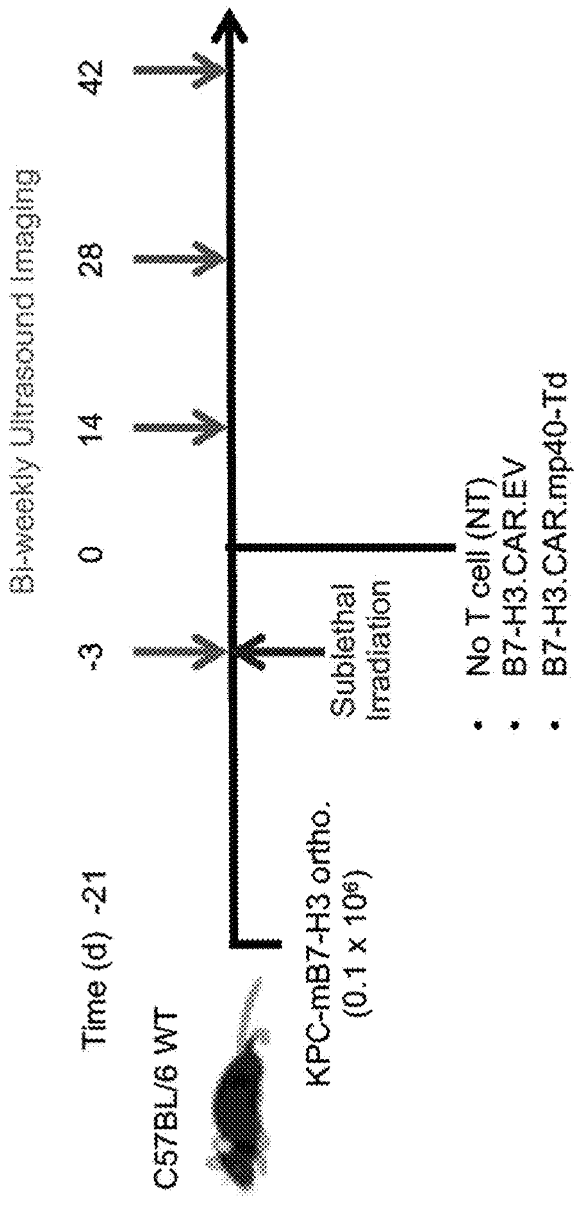
Figure 5K:
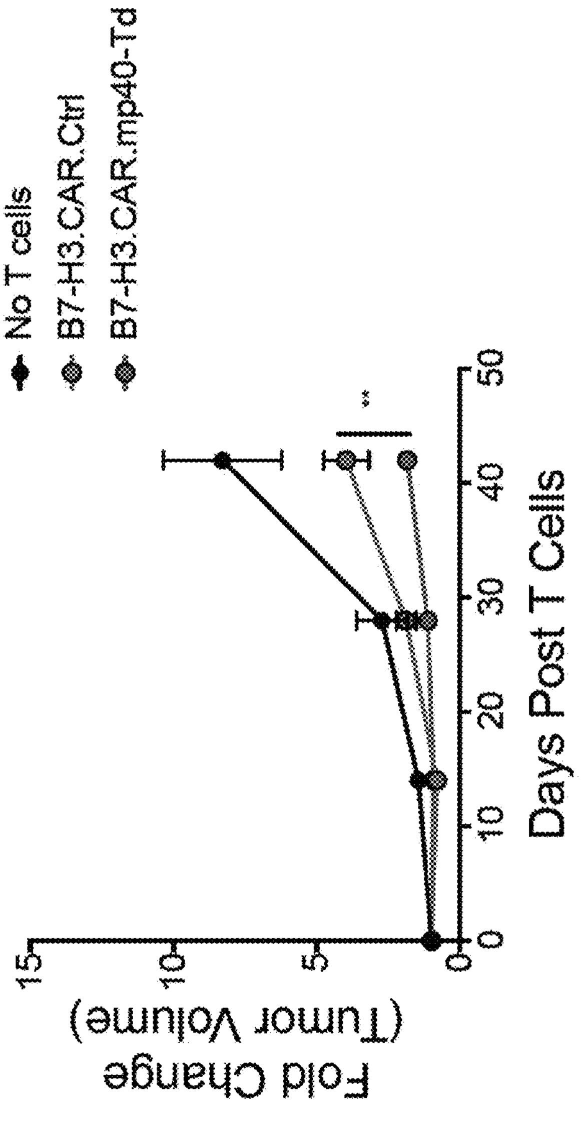

To evaluate the effects of IL23 in immune replete mice, syngeneic tumor models were implemented. It was first confirmed that IL23R, IL23A, but not IL12B genes are inducible in ex vivo activated murine T cells that resemble human ex-$T_M$ generated for adoptive T cell transfer (FIGS. 5A-5B). Recapitulating the observation in human ex-$T_M$, gene transfer of the murine IL12B in murine T cells resulted in the activation inducible IL23 secretion (FIG. 5C), and enhanced T cell expansion in vitro upon TCR stimulation (FIG. 5D). The anti-tumor effects of murine T cells expressing the murine p40 subunit were tested using the B16-OVA melanoma mouse model and adoptive transfer of ex vivo expanded OT-1 T cells (FIG. 5E). When B16-OVA bearing mice were treated with suboptimal doses (1×10$^6$ cells/mouse) of OT1 T cells, OT1 T cells engineered to express p40 (OT1-mp40-Td cells) had superior tumor control as compared to OT1 T cells transduced with the empty vector (OT1-EV) (FIG. 5F (left)). Treatment with a higher dose (2×10$^6$ cells/mouse) of OT1-mp40-Td showed sustained tumor control up to 30 days post tumor inoculation (FIG. 5F (right)). Notably, IL23 was only detected in the supernatant obtained from the tumor, but not in the serum of mice treated with OT1-mp40-Td cells (FIG. 5G). Correspondingly, in mice infused with OT1-mp40-Td cells, higher percentage of $CD8^+$OT1 T cells was observed within the tumor, but not in the blood, spleen and tumor draining lymph nodes (dLN) where the frequency of OT-1 T cells was similar to mice receiving control OT1-EV T cells (FIG. 5H). Furthermore, no alteration in the composition of CD4 and CD8 T cells, B cells, NK cells and myeloid cells was observed in the blood, spleen, tumor and draining lymph nodes (FIG. 5I). To further validate the approach using CAR T cells, a previously established syngeneic PDAC model and B7-H3-specific CAR-T cells was used [29] (FIG. 5J). Specifically, the KPC PDAC cell line expressing murine B7-H3 was orthotopically engrafted in C57BL/6 mice. Upon engraftment, mice were treated with murine T cells expressing the B7-H3-specific CAR co-expressing either an empty vector (B7-H3.CAR.EV) or the murine p40 subunit (B7-H3.CAR.mp40-Td). Mice treated with B7-H3.CAR.mp40-Td cells showed significantly better tumor control as compared to mice treated with B7-H3.CAR.EV cells (FIG. 5K). Collectively, it was demonstrated that p40 engineering in murine T cells expressing either a tumor specific TCR or CAR exert a local effect that enhances their anti-tumor activity without disturbance of global immune composition.

Engineered IL23 Functions Predominantly Through an Autocrine Mode of Action.

Figure 6A:
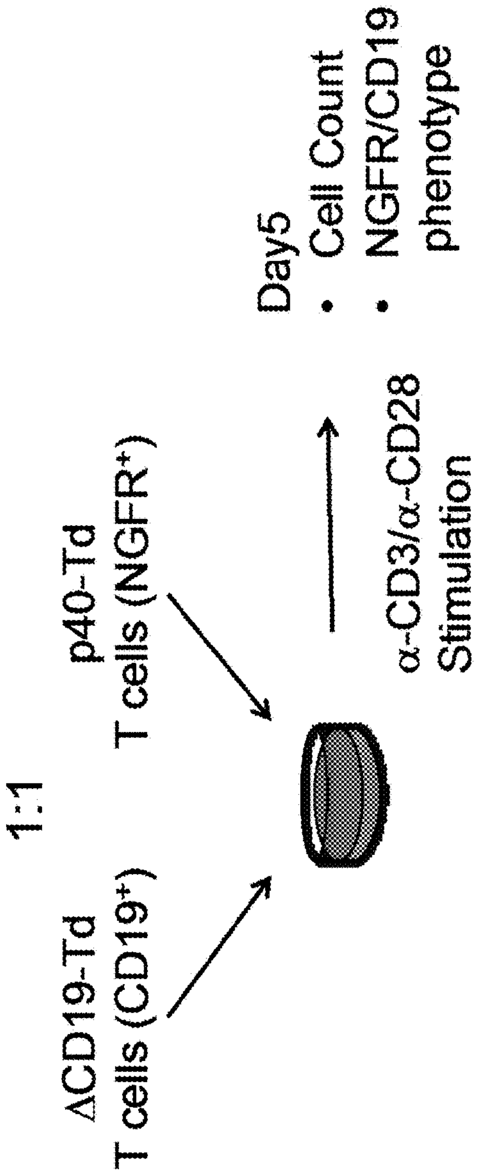
FIGS. 6A-6M demonstrate engineered IL23 functions predominantly through an autocrine mode of action.
Figure 6B:
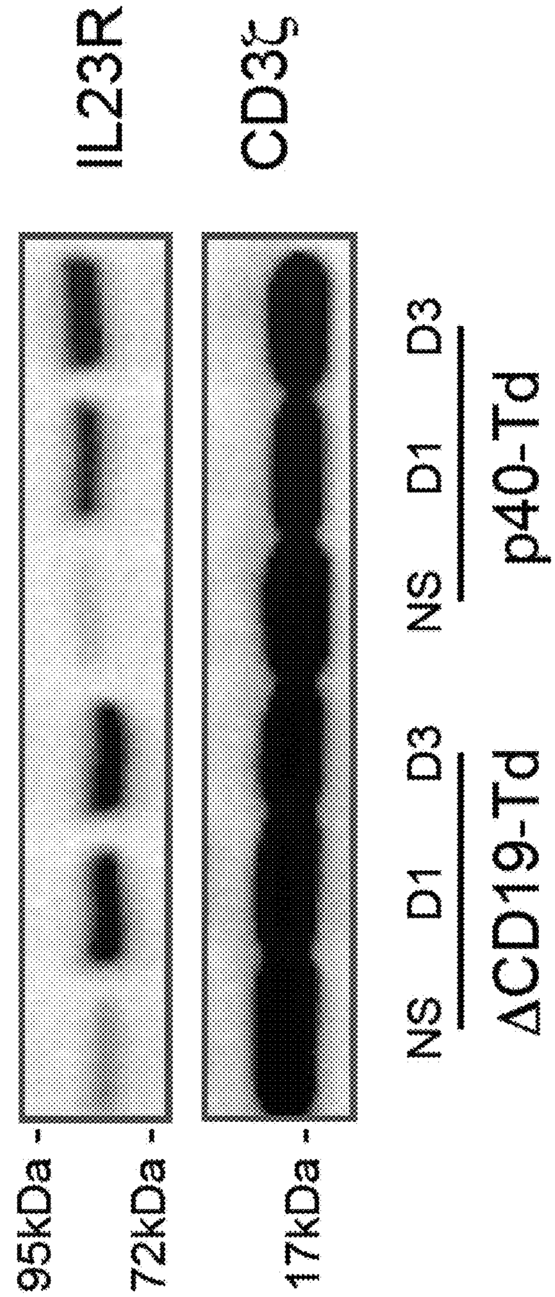
Figure 6C:
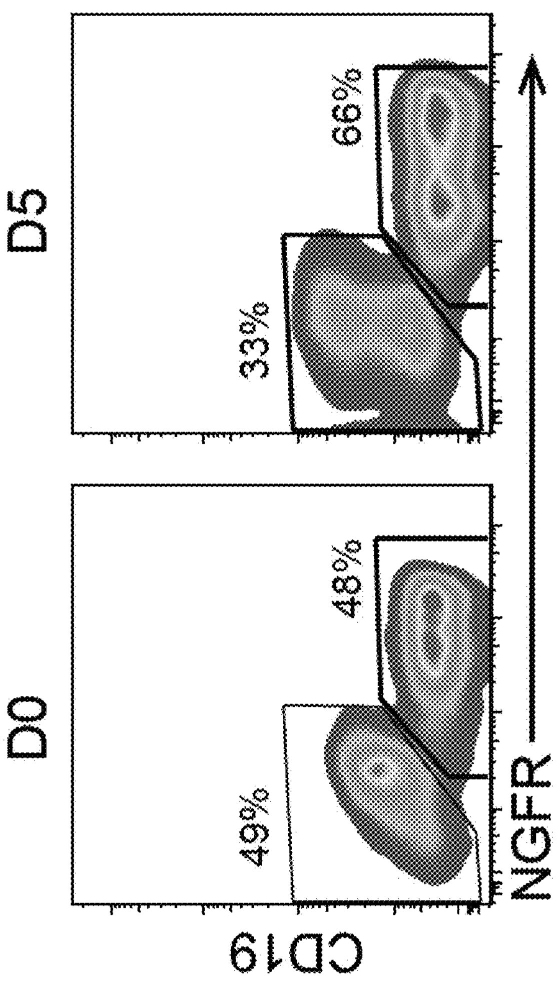
Figure 6D:
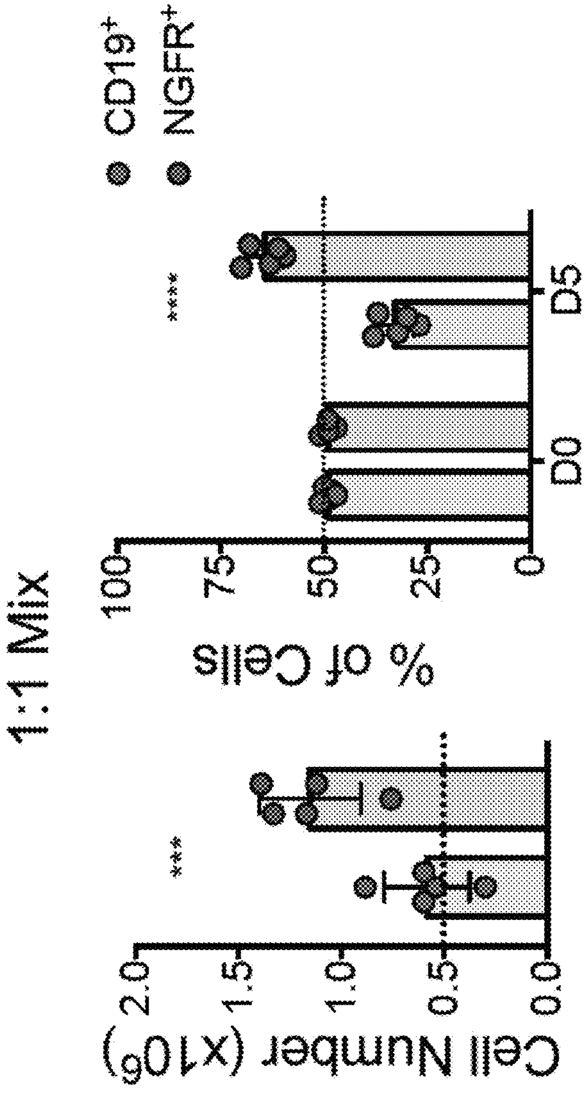
Figure 6E:
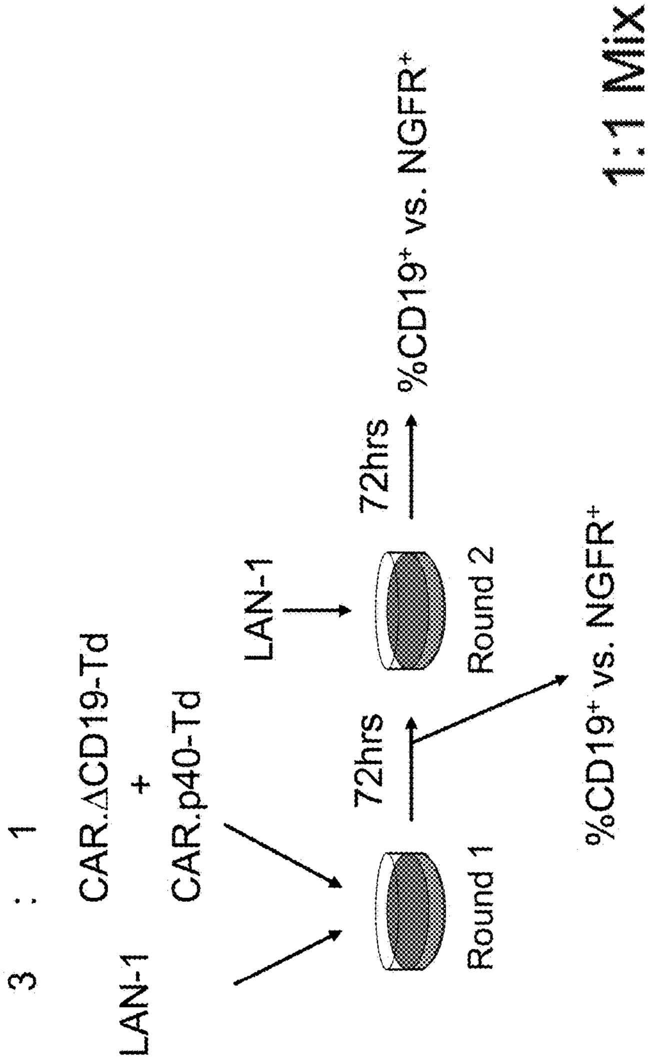
Figure 6F:
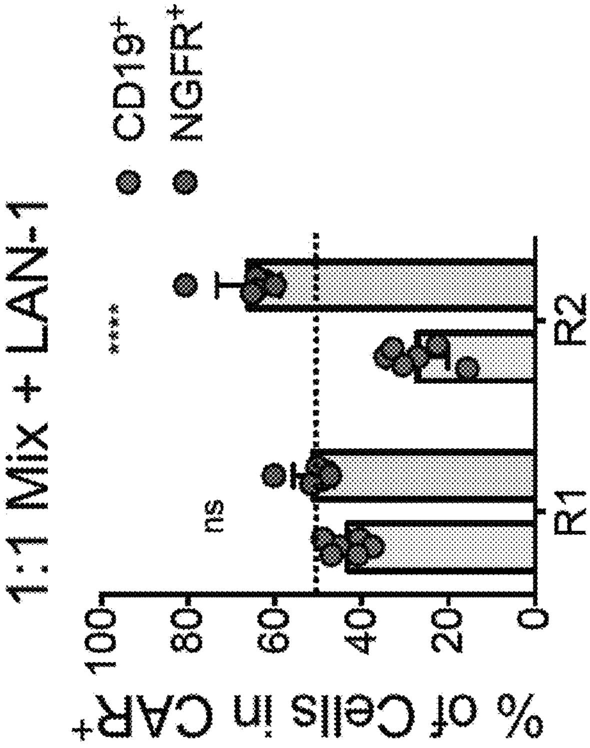
Figure 6G:
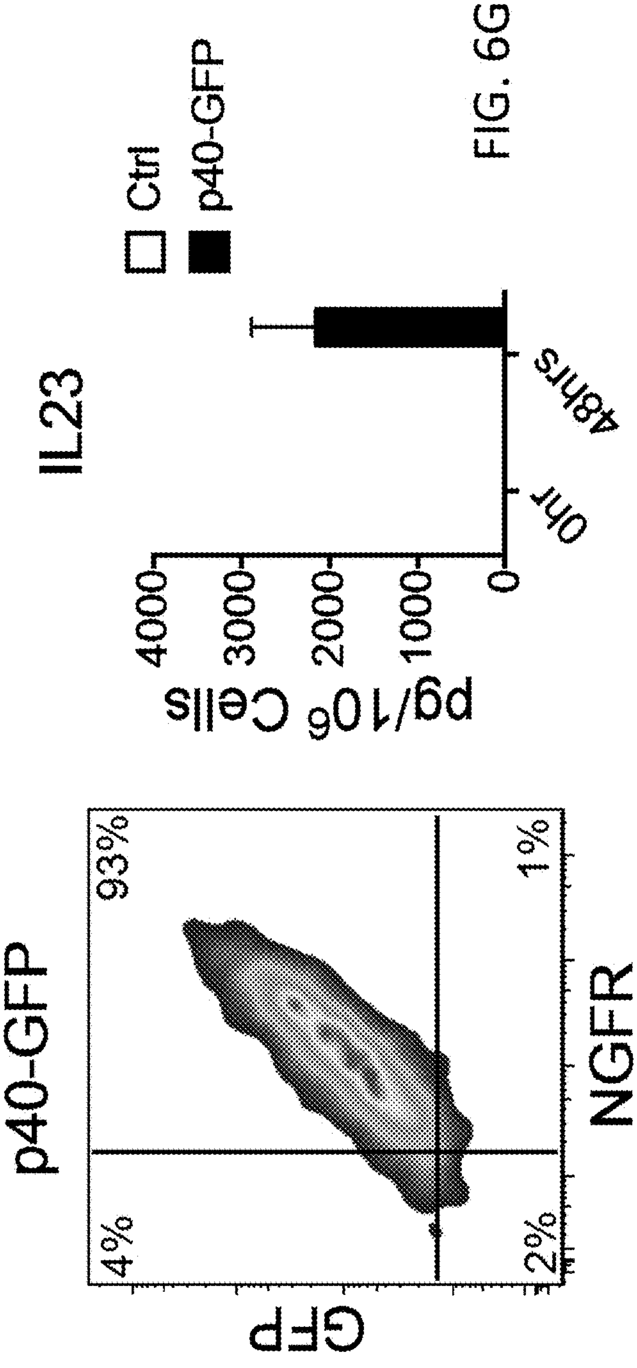
Figure 6H:
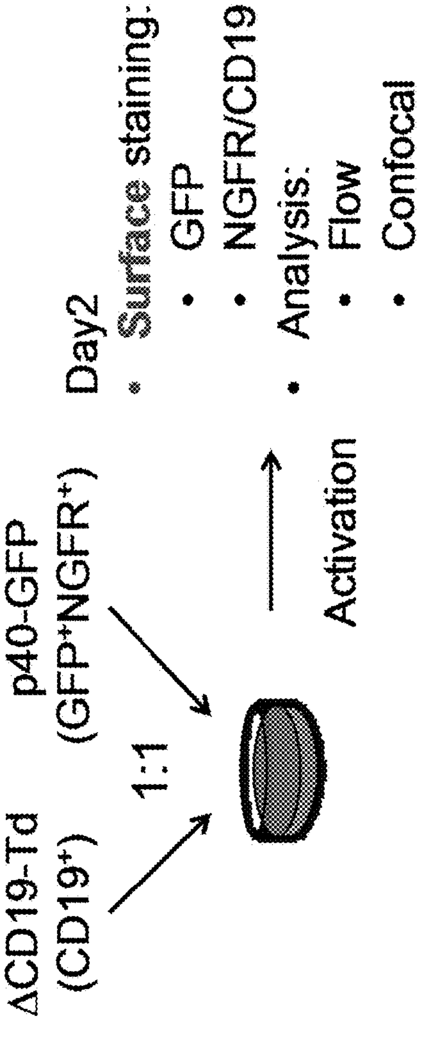
Figure 6I:
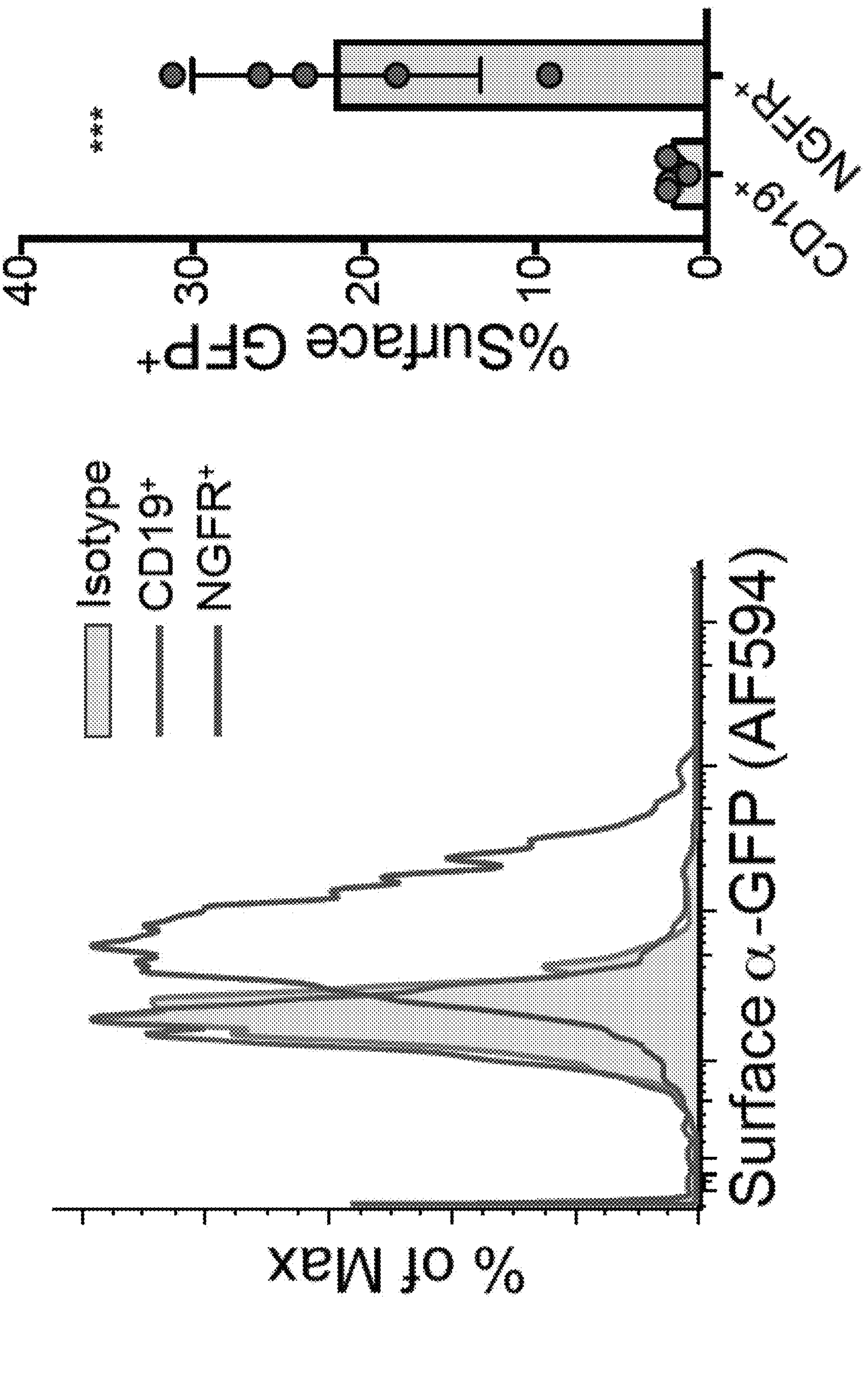
Figure 6J:
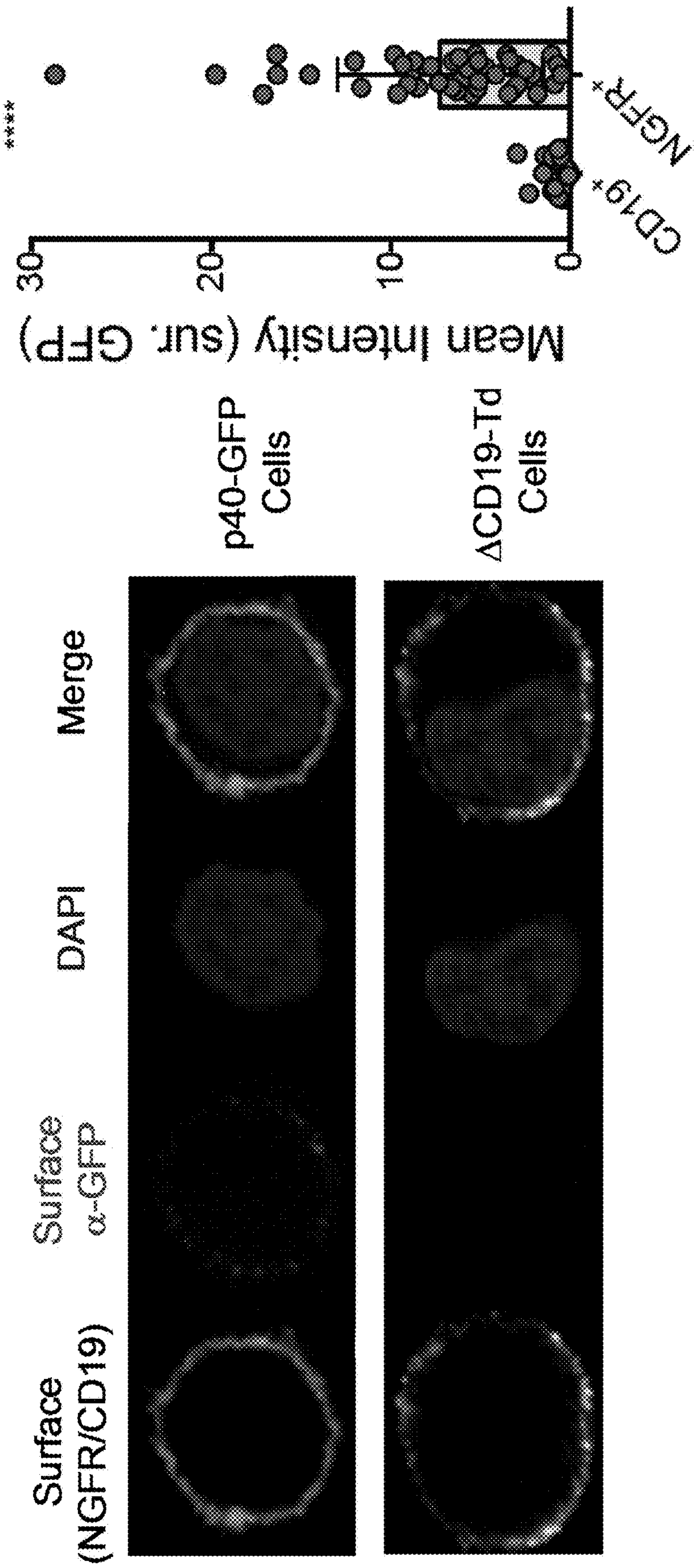
Figure 6L:
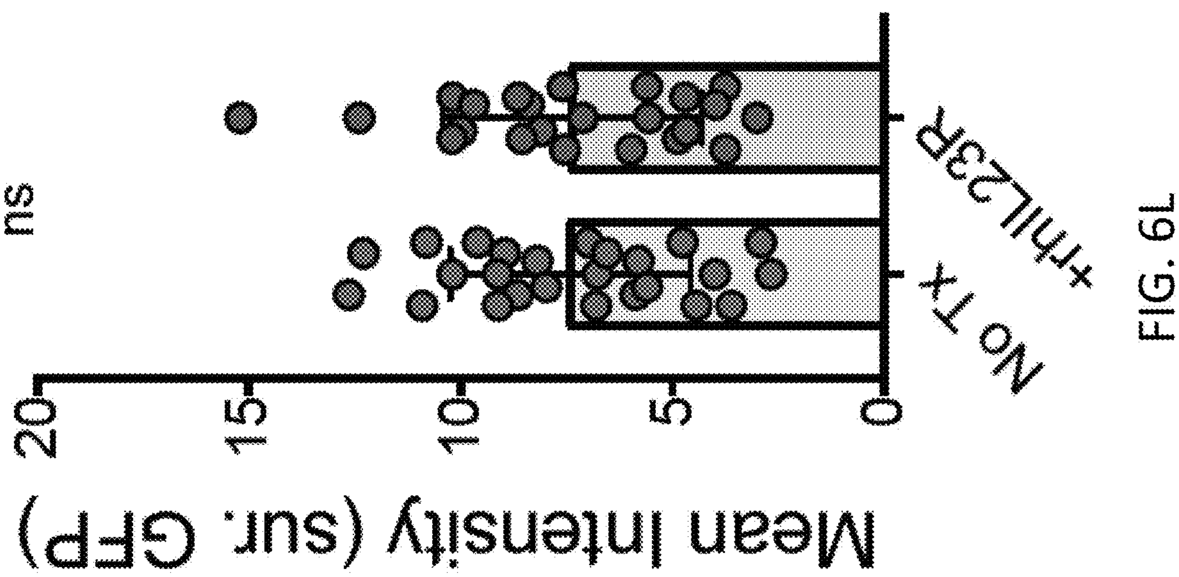
Figure 6K:
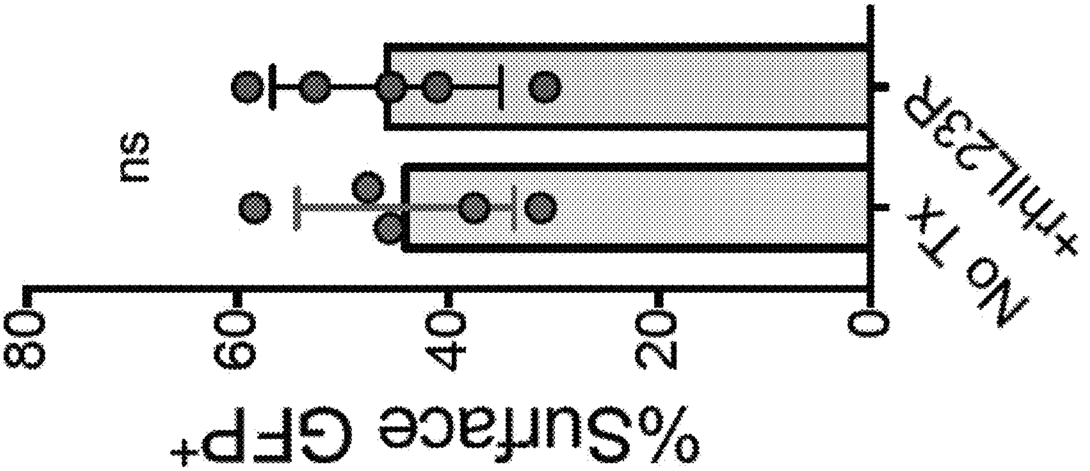
Figure 6M:
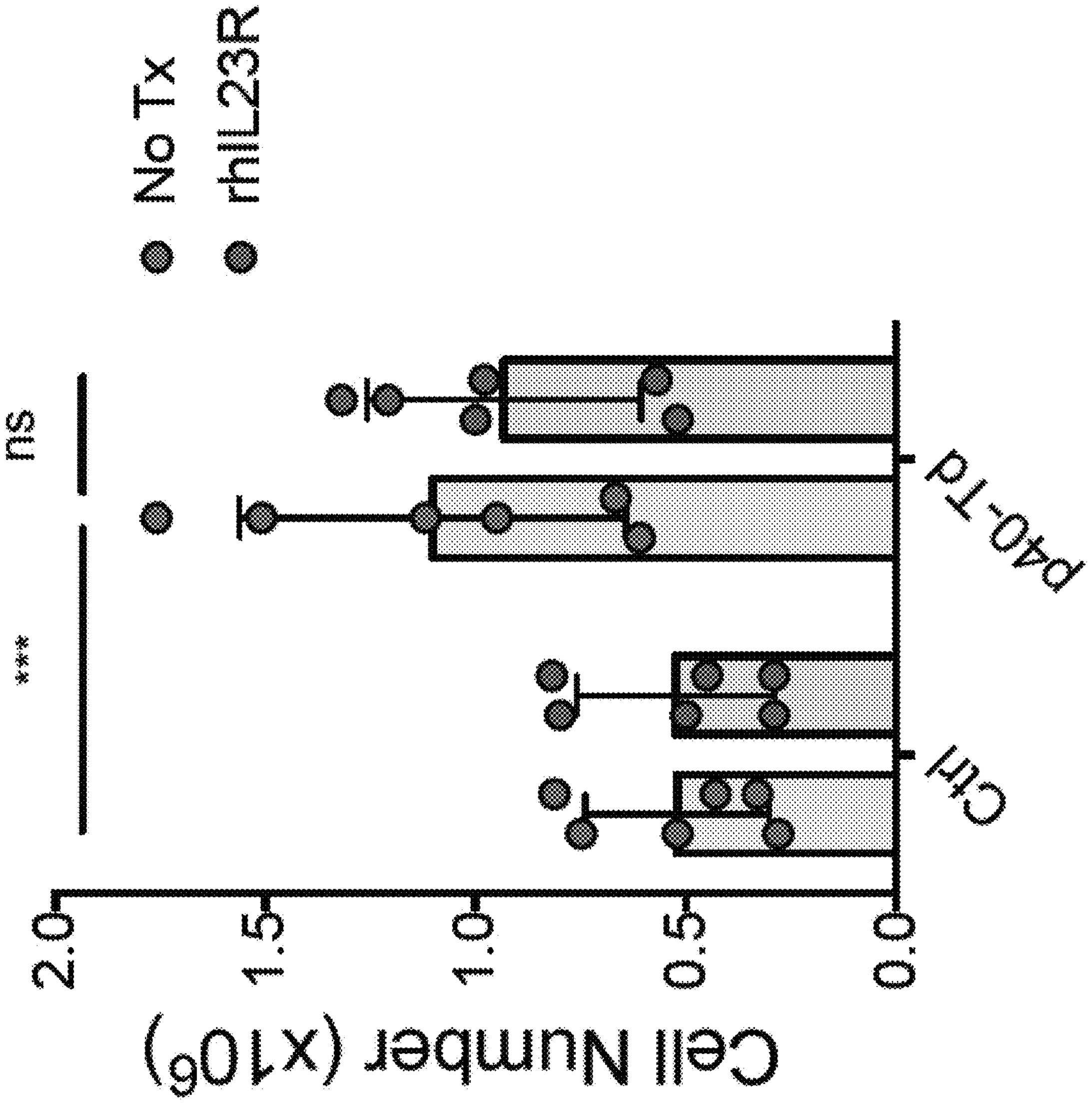
Figure 10:
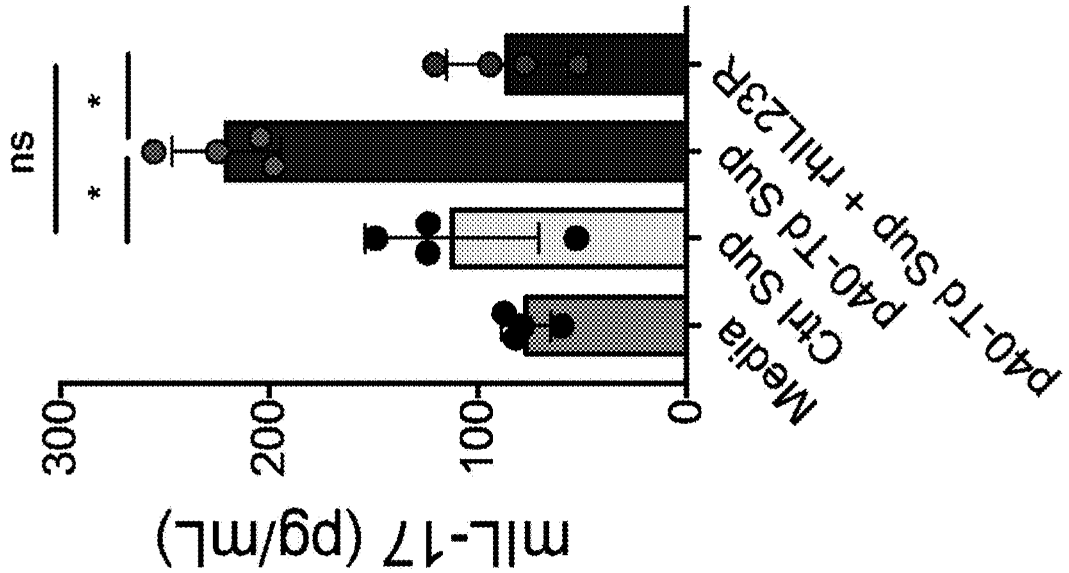
FIG. 10 demonstrates that recombinant human IL23R (rhIL23R) sequesters IL23. Supernatant of Ctrl or p40-Td cells were incubated with murine splenocytes with or without rhIL23R. Murine IL17 release by the splenocytes in response to IL23 was measured by ELISA. Data are presented as individual values and mean±SD (n=4). *p=0.0122 for Ctrl cells vs. p40-Td cells; *p=0.0308 for p40-Td cells vs. p40-Td cells plus rhIL23R. p values were determined by repeated measure 1-way NAOVA with Sidak post hoc test.

To better characterize the mode of action of IL23 in p40-expressing T cells, in vitro p40-Td cells, which are tagged with a truncated form of NGFR ($NGFR^+$) [30], were mixed with control T cells tagged with a truncated form of CD19 (ΔCD19-Td) [31] at 1:1 ratio and the mixed cells were stimulated with αCD3 and αCD28 Abs (FIG. 6A). Despite sharing the same culture media containing IL23 and expressing comparable levels of IL23R (FIG. 6B), p40-Td cells expanded more than ΔCD19-Td cells (FIGS. 6C-6D). Similarly, after multiple-round coculture assays with mixed CAR.p40-Td and control CAR.ΔCD19-Td cells, CAR.p40-Td cells preferentially expanded in response to tumor cells as compared to control CAR T cells (FIGS. 6E-6F). To further study the self-beneficial effects of IL23 in p40-Td cells, IL23 produced by p40-Td cells was evaluated to determine if it preferentially binds with the IL23R expressed by p40-Td cells rather than the IL23R expressed by bystander cells. A p40-GFP fusion protein was generated that allows for the tracking of the location of IL23 (p19-p40-GFP heterodimers) produced by T cells (FIG. 6G). p40-GFP-transduced (p40-GFP-Td) T cells were cocultured with CD19-tagged control T cells and measured the cell surface binding of the p40-GFP fusion protein using an anti-GFP antibody conjugated to a far-red fluorochrome to discriminate true extracellular binding of the p40-GFP protein from the GFP signal within the cells (FIG. 6H). Upon TCR stimulation, both flow cytometry (FIG. 6I) and confocal microscopy (FIG. 6J) showed abundant GFP surface binding on p40-GFP-Td cells, but not on ΔCD19-Td cells, even if the p19-p40-GFP heterodimers can be readily detected in the culture media (FIG. 6G). These data confirm the preferential binding of IL23 to T cells that are producing IL23. One possible explanation for the IL23 preferential binding to IL23-producing T cells is that IL23 is captured by IL23R in p40-Td cells before its diffusion. To test this hypothesis, a soluble recombinant human IL23R (rhIL23R) was used that binds IL23 preventing its engagement with the IL23R expressed by T cells (FIG. 10). It was found that even when IL23 proteins in diffusion were fully sequestered, the surface binding of p40-GFP to p40-Td cells remain unchanged as measured by both flow cytometry (FIG. 6K) and confocal microscopy (FIG. 6L). In addition, rhIL23R did not hamper IL23-mediated expansion of p40-Td cells (FIG. 6M), suggesting that the free IL23 does not contribute to the binding nor to the function of IL23 in p40-Td cells. Collectively, these data showed an autocrine mode of action of IL23 that has limited effects on bystander cells.

Discussion

In this study, it is demonstrated that providing the p40 subunit of IL23 to tumor-specific T cells is sufficient to cause the production and release of IL23. Furthermore, IL23 exerts its function exclusively through activated T cells because both the IL23 production and IL23R expression occur upon T cell activation. This tightly regulated IL23/IL23R engineered pathway is further controlled by an autocrine mode of action of the secreted IL23 that prevents cytokine usage by other bystander immune cells.

The role of IL23 in tumor cell growth remains controversial. Studies showed that low amounts of endogenous IL23 produced by either tumor associated macrophages, dendritic cells or tumor cells may promote inflammation favoring early tumor initiation and progression [19, 24, 25, 32]. IL23 was also reported to promote metastasis in some CRC models [33]. On the contrary, high levels of IL23, obtained either by IL23-engineered tumor cells or administration of rIL23, caused anti-tumor effects [34, 35]. The data in multiple mouse models demonstrated the anti-tumor benefit of IL23, when this cytokine is produced by engineered tumor-specific T cells, while exhibiting no obvious side effects. Furthermore, it was observed that IL23 by itself is not sufficient to promote the differentiation of ex vivo generated tumor-specific T cells into IL17 producing cells, the main culprit for promoting carcinogenesis in IL23 sensitive tumors, such as CRC [25].

The unexpected observation was made that the IL23A p19 gene, but not the IL12B p40 gene, is expressed in ex vivo generated tumor-specific T cells when these cells are activated either via engagement of the endogenous TCR or engagement of an inserted CAR. Furthermore, the observed activation-dependent p19 expression is conserved in both murine and human T cells, and especially in murine T cells where p19 expression is upregulated by more than 10000-fold upon activation. Notably, p19 is sufficiently expressed to allow functional production and release of IL23 if the p40 subunit is provided. It is generally believed that no specific functions have been attributed to the single p19 subunit. It is generally accepted that IL23 in its heterodimer form is assembled intracellularly and that p19 is not secreted as an independent protein nor in association with proteins other than p40 [16, 36]. However, one study showed that human gastric carcinoma cells can secret p19 in the absence of p40 subunit [37], which implies that the subunit may have IL23 independent functions. While the data suggest that IL23A knockdown does not cause detrimental effects in T cells, a more exhaustive assessment of the function p19 in T cells is warranted.

The p40 engineering proposed has multiple potential advantages. While a milieu of cytokines supporting T cell survival and proliferation is critical to obtain anti-tumor effects after T cell adoptive therapies, the clinical experience demonstrates that toxic effects secondary to systemic and uncontrolled cytokine spread occur. The proposed p40-engineering restricts cytokine spread because IL23 is released exclusively upon T cell activation within the TME. In fact, even if the p40 subunit is constitutively expressed in engineered T cells, IL23 is only assembled when the p19 subunit is upregulated in response to T cell activation. Upon secretion within the TME, $\gamma_c$-chain cytokines can be used by a variety of immune cells that express $\gamma_c$-chain receptor, which either amplify or attenuate T cell-mediated immune responses [38, 39]. In contrast, IL23R expression is much more restricted and T cells releasing IL23 express high levels of IL23R. This scenario was previously modeled in the context of IL2 and regulatory T cells, showing that it favors the preferential capture of the cytokine by its producing cells and limits diffusion and bystander effects [40, 41]. Indeed, IL23 released by p40-engineered T cells is preferentially bound to the IL23R expressed by the same cells. This model for IL23 was supported by the data showing that soluble IL23R sequestering soluble IL23 did not reduce its binding and activity in p40-Td cells. Therefore, this autocrine mode of action of IL23 further improves the specificity and safety of p40-engineering in tumor specific T cells.

The generation of autologous cellular T cell products in cancer patients has the caveats that T cells may be functionally impaired due to age, specific disease and previous therapy the patient may have received. It was recently shown that in patients with chronic lymphocytic leukemia, which is characterized by the presence of dysfunctional T cells, the activation of the STAT3 signaling pathways correlated with better performance of CAR T cells generated ex vivo. The data support the beneficial role of STAT3 associated pathways, which are induced by IL23 through p40-engineering. Downstream of STAT3 signaling, an enrichment of hypoxia related genes in p40-Td cells was also observed. It is speculated that this effect is possibly due to the cooperative transactivation of STAT3 and HIFs transcription factor [42, 43]. Furthermore, this molecular profile resembles the previously described hypoxia-signature in effector-memory T cells that likely contributes to the proliferative and anti-apoptotic functions of p40 [21].

In summary, a novel strategy is described to incorporate a highly regulated cytokine signaling into tumor-specific T cells that improves their efficacy. This approach has significant translational potential since it can be used for both CAR- and TCR-engineered T cells because both TCR and CAR activation allows upregulation of the IL23R and p19 subunits and the endogenous p19 subunit can be coupled with the ectopically expressed p40 subunit.

Methods

Cell Lines

The CHLA-255 neuroblastoma cell line was provided by L. S. Metelitsa of Baylor College of Medicine [44] and the LAN-1 cell line was obtained from M. Brenner at Baylor College of Medicine [45]. Human PDAC cell line BXPC-3 was purchased from American Type Culture Collection (ATCC). Tumor cell lines were transduced with eGFP or firefly luciferase (Ffluc) for coculture and mouse experiments, respectively as previously described [46]. Human tumor cell lines in this study (LAN-1, CHLA-255, BXPC-3) were maintained in complete RPMI medium (500 mL RPMI-1640 (Gibco), 10% FBS (Germini), 2 mM GlutaMAX (Gibco), 100 unit/mL of Penicillin and 100 μg/mL of streptomycin (Gibco)). Mouse melanoma B16-OVA was provided by Benjamin Vincent at University of North Carolina at Chapel Hill and was maintained in complete RPMI medium with addition of 100 μM β-mercaptoethanol (Fisher) and 500 ug/mL G418 (Gibco) to maintain OVA expression. Mouse PDAC cell line KPC-mB7-H3 was established and described previously [29] and maintained in complete RPMI media. All cell lines were routinely tested for mycoplasma and for surface expression of target antigens.

Plasmid Construction and Retrovirus Production.

The full-length human IL12B (accession number NM_002187.2) and murine IL12B (accession number NM_001303244.1) genes were amplified by PCR from cDNA clone purchased from Origene, and cloned into the retroviral vector SFG. Human IL12B were then subcloned into SFG vector containing the internal ribosomal entry site (IRES) and truncated NGFR selectable marker (p40(i) NGFR, FIG. 7A). As control, an empty vector containing the IRES and NGFR gene (Ctrl(i)NGFR) was used. The shRNA construct for IL23A gene was purchased from Origene (HuSH-29™) and the promoter and shRNA sequence were amplified by PCR and cloned into SFG vector following a reverse (3' to 5') orientation. The p40-GFP fusion protein was generated by fusing the coding region of IL12B (1-328 amino acids) with the GFP gene by fusion PCR, and cloned into the SFG(I)NGFR. The CAR constructs used in this study were described previously [47].

Retroviral supernatants used for the transduction were prepared as previously described [48]. To transduced human T cells, retrovirus with RD114 envelope was used. For murine T cells transduction, retrovirus was generated using packaging vector encoding Eco envelope protein.

Transduction and Expansion of Human T Cells.

Buffy coats from healthy donors were purchased from the Gulf Coast Regional Blood Center, Houston, TX Peripheral blood mononuclear cells (PBMCs) isolated with Lymphoprep density separation (Fresenius Kabi Norge) were activated on plates coated with 1 μg/mL CD3 (Miltenyi Biotec) and 1 μg/mL CD28 (BD Biosciences) agonistic mAbs. On day 2, T lymphocytes were transduced with retroviral supernatants using retronectin-coated plates (Takara Bio Inc.). On day 4, transduced T cells were collected from retronectin plate and expanded in complete T cell medium (45% RPMI-1640 and 45% Click's medium (Irvine Scientific), 10% FBS (Hyclone), 2 mM GlutaMAX, 100 unit/mL of Penicillin and 100 μg/mL of streptomycin) with IL-7 (10 ng/mL; PeproTech) and IL-15 (5 ng/mL; PeproTech), changing medium every 2-3 days [49]. On day 10-14 days post transduction, cells are collected for in vitro and in vivo experiments. T cells were cultured in IL-7/IL-15 depleted medium for one days prior to being used in in vitro assays.

Preparation of Ex Vivo Expanded Murine T Cells.

Murine T cells were isolated using Mojosort T cell isolation kit (Biolegend) from splenocytes obtained from C57BL/6J or C57BL/6-Tg(TcraTcrb)1100Mjb/J (OT-1) mice acquired from The Jackson Laboratory or in-house breeding. T cells were then stimulated on plates coated with 1 μg/mL mCD3 (eBioscience) and 1 μg/mL mCD28 mAbs (eBioscience) for 48 hours. Activated murine T lymphocytes were transduced with retroviral supernatants using retronectin-coated plates with the same protocol used to transduce human T cells. After removal from the retronectin plates, T cells were expanded in complete medium (RPMI-1640 (Gibco), 10% FBS (Hyclone), 2 mM GlutaMAX, 100 μM β-mercaptoethanol, 100 unit/mL of Penicillin and 100 μg/mL of streptomycin) with IL-7 (10 ng/mL) and IL-15 (5 ng/mL) changing medium every 2 days. On day 5, T cells were collected and used for subsequent assays.

Quantitative Real-Time PCR.

RNA was extracted from cells with RNeasy Plus Kit (Qiagen), quantified using Nanodrop or Qubit and reverse-transcribed into cDNA using Superscript VILO (Thermo). Quantitative real-time PCR was performed using QuantStudio 6 Flex real-time PCR system (Thermo). Taqman system was used in most assays except for the validation of RNA-Seq analysis (STAT3 regulated and hypoxia pathway genes), which used the SYBR Green system. For comparison of gene expression in human T cells, 18S RNA was used as housekeeping gene for normalization. For assays in mouse T cells, CD3E was used as housekeeping gene for normalization. For assays in patient specimens, absolute quantification of copies was conducted using standard curved generated with plasmid containing IL23A or IL12B cDNA.

The Taqman primers for the following genes were purchased from Applied Biosystem:

human IL23A (assay ID: Hs00372324_m1)
human IL12B (assay ID: Hs01011518_m1)
human 18S RNA (assay ID: Hs03003631_g1)
human IL23R (assay ID: Hs00332759_m1)
human TBX21 (assay ID: Hs00894392_m1)

human RORC (assay ID: Hs01076112_m1)
murine IL23A (assay ID: Mm00518984_m1)
murine IL12B (assay ID: Mm01288989_m1)
murine CD3E (assay ID: Mm01179194_m1)
murine IL23R (assay ID: Mm00519943_m1)

The SYBR Green primers for the following genes were purchased from Sigma:

```
18S
                                   (SEQ ID NO: 1)
F:          AACCCGTTGAACCCCATT;

                                   (SEQ ID NO: 2)
R:          CCATCCAATCGGTAGTAGCG;

SOX2
                                   (SEQ ID NO: 3)
F:          ATAATAACAATCATCGGCGG;

                                   (SEQ ID NO: 4)
R:          AAAAAGAGAGAGGCAAACTG;

SOCS3
                                   (SEQ ID NO: 5)
F:          CCTATTACATCTACTCCGGG;

                                   (SEQ ID NO: 6)
R:          ACTTTCTCATAGGAGTCCAG;

CEBPD
                                   (SEQ ID NO: 7)
F:          CAGACTTTTCAGACAAACCC;

                                   (SEQ ID NO: 8)
R:          TTTCGATTTCAAATGCTGC;

ABCA1
                                   (SEQ ID NO: 9)
F:          GTGTTTCTGGATGAACCC;

                                  (SEQ ID NO: 10)
R:          TTCCATTGACCATGATTGC;

IFIT1
                                  (SEQ ID NO: 11)
F:          CTGCCTAATTTACAGCAACC;

                                  (SEQ ID NO: 12)
R:          TGATCCAAGACTCTGTTTTC;

IFIT3
                                  (SEQ ID NO: 13)
F:          ATGAGTGAGGTCACCAAG;

                                  (SEQ ID NO: 14)
R:          CCTTGAAGTTCCAGGTG;

USP18
                                  (SEQ ID NO: 15)
F:          TGGTTTACACAACATTGGAC;

                                  (SEQ ID NO: 16)
R:          ATCCTCTTCAATATCCTGGTG;

CDKN2B
                                  (SEQ ID NO: 17)
F:          GACTAGTGGAGAAGGTGC;

                                  (SEQ ID NO: 18)
R:          TCATCATGACCTGGATCG;

HIF1A
                                  (SEQ ID NO: 19)
F:          AAAATCTCATCCAAGAAGCC;

                                  (SEQ ID NO: 20)
R:          AATGTTCCAATTCCTACTGC;
```

-continued

```
EPAS1
                                  (SEQ ID NO: 21)
F:          CAGAATCACAGAACTGATTGG;

                                  (SEQ ID NO: 22)
R:          TGACTCTTGGTCATGTTCTC;

BNIP3L
                                  (SEQ ID NO: 23)
F:          AGGCATCTATATTGGAAAGC;

                                  (SEQ ID NO: 24)
R:          GCTTACAATGGTCTCAAGTT;

PDK1
                                  (SEQ ID NO: 25)
F:          ATGATGTCATTCCCACAATG;

                                  (SEQ ID NO: 26)
R:          AAGAGTGCTGATTGAGTAAC;

DDIT3
                                  (SEQ ID NO: 27)
F:          CTTTTCCAGACTGATCCAAC;

                                  (SEQ ID NO: 28)
R:          GATTCTTCCTCTTCATTTCCAG;

DDIT4
                                  (SEQ ID NO: 29)
F:          AATGTAAGAGTAGGAAGGGG;

                                  (SEQ ID NO: 30)
R:          ACAGTTCTAGATGGAAGACC;

EGLN1
                                  (SEQ ID NO: 31)
F:          CCCAAATTTGATAGACTGCTG;

                                  (SEQ ID NO: 32)
R:          ACACCTTTTTCACCTGTTAG;

EGLN3
                                  (SEQ ID NO: 33)
F:          ATCATTCATAGCAGATGTGG;
and

                                  (SEQ ID NO: 34)
R:          ATATCTGGTTGCGTAAGAGG;
```

Immunoblotting Analysis.

Cellular protein was extracted from cells using RIPA buffer (Thermo) supplemented with proteinase and phosphatase inhibitor (Thermo). Same amount of protein was separated on pre-cast 4-15% gradient gels (BioRad) by SDS-PAGE and transferred to PVDF membranes (BioRad). The membranes were blocked with 5% Milk in TBS-5% Tween buffer and probed with primary antibodies at 4 degree overnight. Then, the membranes were washed and incubated with secondary antibodies conjugated to HRP. The following primary and secondary antibodies were used: anti-IL23R (Novus Biological 1:1000 Dilution), anti-GAPDH (clone 6C5, Santa Cruz, 1:1000 Dilution), anti-phospho-STAT3 (Tyr705) (clone D3A7, Cell Signaling Technology, 1:1000 dilution), anti-phospho-STAT3(Ser727) (clone 6E4, Cell Signaling Technology, 1:1000 Dilution), anti-STAT3 (clone D3Z2G, Cell Signaling Technology, 1:1000 Dilution) and anti-CD3 (clone 6B10.2, Santa Cruz, 1:1000 Dilution). Blot images were acquired with ChemiDoc MP system (BioRad) and the densitometry was calculated by Image Lab software (Bio-Rad).

Flow Cytometry.

For surface staining, cells were incubated with antibodies at room temperature for 15 mins or at 4° C. for 30 min. For intracellular staining, cells were fixed and permeabilized using Cytofix/CytoPerm (BD Biosciences) for 15 mins at room temperature and washed with 1×PermWash (BD Biosciences). Subsequent staining was performed using 1×PermWash as staining and wash buffer. For CellTrace Violet (CTV) staining, cells were labeled with 5 uM CTV (Thermo) before culture. In most assays, cells were stained with Zombie Aqua Live/Dead Discrimination dye (Biolegend) to gate out dead cells for analysis.

The following antibodies used for the flow cytometry analysis were obtained from BD Biosciences: APC-conjugated anti-CD4 (Clone RPA-T4), FITC-conjugated anti-CD8 (Clone RPA-T8), Alexa Fluor 700-conjugated anti-CD8 (Clone RPA-T8), PE-conjugated anti-IL17A (Clone SCPL1362), Alexa Fluor 647-conjugated anti-IFNγ (Clone B27), Alexa Fluor 647-conjugated anti-CD271 (NGFR, Clone C40-1457), APC-conjugated anti-CD45RO (Clone UCHL1), PE-conjugated anti-CD45RA (Clone H100), PE-Cy7-conjugated anti-CD28 (Clone CD28.2), BV421-conjugated anti-CD27 (Clone M-T271), PE-Cy7-conjugated anti-CD279 (PD1, Clone EH12.1), BV711-conjugated anti-Tim3 (Clone 7D3), PE-conjugated anti-CD223 (LAG3, Clone T47-530), Alexa Fluor 647-conjugated anti-Ki67 (Clone B56), PE-conjugated Annexin V, 7AAD, PE-conjugated rat-anti-mouse IgG1 (Clone X56), APC-Cy7-conjugated anti-CD3 (Clone SK7), PE-conjugated anti-granzyme B (Clone GB11), PE-conjugated anti-CD101 (Clone V7.1), PE-conjugated anti-TNF-α (Clone MAB11), PE-conjugated anti-CD45 (Clone HI30), FITC-conjugated rat anti-mouse CD19 (Clone 1D3), APC-Cy7-conjugated hamster anti-mouse CD3e (Clone 145-2C11), PE-conjugated rat anti-mouse Ly6G (Clone 1A8), BV421-conjugated rat anti-mouse Ly6C (Clone AL21), APC-Cy7 rat anti-mouse CD11b (Clone M1/70), PerCP-Cy5.5-conjugated hamster anti-mouse CD11 c (Clone HL3), PerCP-Cy5.5-conjugated rat anti-mouse CD4 (RM4-5), PE-conjugated rat anti-mouse Va2 TCR (Clone B20.1), FITC-conjugated rat anti-mouse Vb5.1 5.2 TCR (Clone MR9-4).

The following antibodies were obtained from Thermo: Alexa Fluor 647-conjugated anti-CD19 (Clone SJ25-$C_1$), Alexa Fluor 594-conjugated anti-GFP (Polyclonal).

The following antibodies were obtained from Biolegend: BV711-conjugated rat anti-mouse CD45 (Clone 30-F11), APC-conjugated rat anti-mouse CD8 (Clone 53-6.7), APC-conjugated rat anti-mouse CD64 (Clone X54-5/7.1), PE-Cy7-conjugated rat anti-mouse F4/80 (Clone BM8).

Flow cytometry data were collected on BD LSRFortessa (BD Biosciences) using BD FACSDIVA software and the flow data were analyzed by FlowJo software (v9.32, Tree Star).

Acquisition and Processing of Frozen Patient Tumor Samples.

Frozen patient tumor specimens and matching adjacent normal tissues were obtained from the Tissue Procurement Facility at University of North Carolina at Chapel Hill. For RNA extraction, 20-30 mg of frozen tissues were lysed using RLT buffer from RNeasy Plus Kit (Qiagen). To extract extracellular protein within interstitial fluid for IL23 ELISA, 40 mg of frozen tissues were incubated in DPBS to obtain single cell suspension and the supernatant was collected. Total protein amount was quantified using Bradford assay (Bioard) and 100 ug of protein was used for ELISA.

RNA Sequencing and GSEA.

Total RNA was extracted as described above and the library is prepared by the High Throughput Sequencing Facility (HTSF) at University of North Carolina at Chapel Hill using the KAPA Stranded mRNA-Seq Kit (Kapa Biosystem). 12 samples were pooled and sequenced using HiSeq 4000 (Illumina) with high output paired end 50 bp setting (>$20\times10^6$ reads per sample). Sequencing reads were aligned to the human genome (hg38) using STAR aligner (v2.4.2) [50] and subsequently quantified using Salmon (v0.8.2) [51]. The differential expression analysis was conducted using DESeq2 (v3.8) [52] running on R (ver 3.5.0). Genes having >1 log 2foldchange and an FDR rate less than 0.05 between Ctrl and p40-Td cells are being considered significant.

For visualization of PCA plot, genes with low expression (<20 counts across 6 samples (3 Ctrl and 3 p40-Td cells)) were filtered and data was transformed using regularized-logarithm transformation.

GSEA was performed using the GSEA v2 software (Broad Institute) on genes that are differentially expressed between day 5 activated Ctrl and p40-Td cells. Gene sets specified in this study are:

DAUER_STAT3_TARGETS_UP (M12391)—STAT3 Upregulated Genes [53];

DAUER_STAT3_TARGETS_DN (M13696)—STAT3 Downregulated Genes [53]; and

HALLMARK_HYPDXIA (M5891)—Genes upregulated in response to hypoxia.

Selected differentially expressed genes in STAT3 or hypoxia pathways identified in RNA-Seq were independently validated using qRT-PCR.

In Vitro Repetitive Coculture Assays.

$2.5\times10^6$ tumor cells (LA-N-1, CHLA-255 and BXPC-3, all labeled with GFP) were seeded in tissue culture treated 12 well plate for 24 hrs. $5\times10^4$ (E:T=1:5) or $1.25\times10^5$ (E:T=1:2) CART cells were then added to tumor cells. After 3-5 days (due to donor variability in cytotoxicity) when tumor cells were completely eradicated (Round 1, R1). All cells in the well were collected and washed with PBS, resuspended in fresh media and added to a new plate seeded with $2.5\times10^6$ tumor cells for 3 days (Round 2, R2). This procedure was repeated for one more time, if applicable (Round 3, R3). At the end of each round, a duplicate well was collected for counting of residual tumor cells ($GFP^+$) and CAR T cells ($CD3^+$) and other phenotypic analysis (Granzyme B, PD1, CD101) on CAR T cells by flow cytometry.

For cytokine production assay after repetitive coculture, $3\times10^6$ tumor cells (LA-N-1) were irradiated at 40Gy before seeding to reduce tumor burden for T cells. $1\times10^5$ (E:T=1:3) CAR T cells were cocultured with tumors in this assay.

Mouse Experiments

Male and female 6-8 weeks old NSG (NOD/SCID/IL-2Rnull) mice were purchased from the Animal Core Facility at UNC. Male and female 6-8 weeks old C57BL/6J and OT1 mice were purchased from The Jackson Laboratory. All the mice were housed in the Animal Core Facility at UNC. All mouse experiments were performed in accordance with UNC Animal Husbandry and Institutional Animal Care and Use Committee (IACUC) guidelines and were approved by UNC IACUC.

Xenogeneic Mouse Models.

For metastatic neuroblastoma models, CHLA-Ffluc ($2\times10^6$) tumor cells were injected intravenously into 8-10 weeks old female NSG mice. Two weeks later mice are infused intravenously with GD2-specific CAR.Ctrl cells or CAR.p40-Td cells. Tumor progression is monitored weekly by bioluminescence imaging using IVIS lumina II in vivo imaging system (PerkinElmer). For rechallenge experiment, another dose of CHLA-Ffluc ($3\times10^6$) cells were injected intravenously at 4 weeks post T cell infusion. Mice were euthanized when signs of discomfort were detected by the investigators or as recommended by the veterinarian who monitored the mice three times a week. Peripheral blood, spleen and liver (primary tumor site) were collected at indicated time points to measure the expansion and persistence of infused T cells ($hCD45^+hCD3^+$) by flow cytometry.

For orthotopic PDAC model, BxPC-3-Ffluc ($1\times10^5$) tumor cells were suspended in 25 μL DPBS, mixed with 25 μL Matrigel (Corning) and surgically implanted into the pancreas of 8-10 weeks old male NSG mice as previously described [29]. 14 days after tumor cell inoculation, control vector transduced T (Ctrl) cell, B7-H3 specific CAR.Ctrl or CAR.p40-Td cells were injected intravenously via tail injection (i.v.) ($2\times10^6$ cells/mouse). Tumor growth was monitored weekly by bioluminescence imaging using IVIS lumina II in vivo imaging system (PerkinElmer). In this model, the engraftment does not induce lethality of the mice even left untreated for more than 8 weeks post T cell infusion. The mice were arbitrarily considered dead in survival analysis when luciferase signal reached 15-fold over initial signal at week 0. All mice were euthanized at 8 weeks post T cell infusion and the peripheral blood, spleen and pancreas were collected to measure the persistence of infused T cells ($hCD45^+hCD3^+$) by flow cytometry.

Syngeneic Mouse Model.

B16-OVA cells ($5\times10^5$ cells/mouse) were suspended in 50 uL DPBS mixed with 50 uL Matrigel (Corning) and were subcutaneously injected into left flank of 7-8 weeks male C57BL/6 mice. Seven days post tumor engraftment, OT-1-TCR T cells were infused intravenously. Tumor size was monitored every 2-3 days after T cell infusion using a caliper. Tumor volume was calculated as length×width×width×0.5 as previously described [54], and mice with >1000 $cm^3$ were euthanized. After euthanization, blood, spleen, tumor and tumor dLN was collected for immunophenotyping by flow cytometry.

For the orthotopic PDAC model, the murine tumor cell line KPC-4662 was engineered to express mB7-H3, and implanted into pancreas of six week old C57BL/6J female mice by surgery ($1\times10^5$ cells/mouse). Eighteen days post tumor cell implantation, mice were irradiated with 400 cGy to create a lymphodepleted environment. Two days post-irradiation, mice were infused i.v. with syngeneic T cells ($1\times10^7$ cells/mouse). Tumor growth was monitored by US imaging biweekly.

Confocal Microscopy.

Cell were collected and split in half. One half was stained with Alexa594-conjugated mouse anti-GFP antibody (Thermo) and Alexa647-conjugated anti-NGFR (BD Biosciences) while the other half were stained with Alexa594-conjugated mouse anti-GFP antibody and Alexa647-conjugated anti-CD19 antibody (Thermo). Cells were stained for 30 min at 4° C. and subsequently washed with ice cold DPBS. Cells were then fixed with Cytofix (BD Biosciences) for 10 min at room temperature, washed with DPBS and loaded onto a glass slide using Cytospin Cytocentrifuge (Thermo). Prolong Diamond Antifade Mountant with DAPI (Thermo) was applied before sealing the slide with a category 1.5 cover slip (Thermo). The slides were imaged using Zeiss LSM710 and image data were analyzed with FIJI (Image J).

To quantify binding of p40-GFP fusion protein on cell surface, the cell membrane was first defined based on Alexa647 signal (anti-NGFR or anti-CD19 that marks p40-Td or ΔCD19-Td cells, respectively). In parallel, an irrelevant area (either area with no cell or intracellular space) was selected as background area. The mean fluorescence intensity (MFI) of Alexa594 signal (anti-GFP) was measured on membrane area and background area and the surface binding of p40-GFP was calculated as MFI(membrane)-MFI(background).

Statistical Analysis

Student's t test was used to determine statistically significant differences between 2 samples. When multiple comparison analyses were required, statistical significance was evaluated by ANOVA (one-way or two-way), followed by Sidak post-hoc analysis. If the data reflected measurement of 1 sample over time or under different conditions, repeated-measures ANOVA was used, followed by Sidak post-hoc analysis. All statistical analyses were performed with 2-tailed tests. Graph generation and statistical analyses were performed using GraphPad Prism, version 7 (GraphPad Software). A p value of less than 0.05 was considered statistically significant.

REFERENCE

1. Anderson, K. G., Stromnes, I. M. & Greenberg, P. D. Obstacles Posed by the Tumor Microenvironment to T cell Activity: A Case for Synergistic Therapies. *Cancer Cell* 31, 311-325 (2017).
2. Garber, K. Driving T-cell immunotherapy to solid tumors. *Nat Biotechnol* 36, 215-219 (2018).
3. D'Angelo, S. P., et al. Antitumor Activity Associated with Prolonged Persistence of Adoptively Transferred NY-ESO-1 (c259)T Cells in Synovial Sarcoma. *Cancer Discov* 8, 944-957 (2018).
4. Porter, D. L., Levine, B. L., Kalos, M., Bagg, A. & June, C. H. Chimeric antigen receptor-modified T cells in chronic lymphoid leukemia. *N Engl J Med* 365, 725-733 (2011).
5. Maude, S. L., Teachey, D. T., Porter, D. L. & Grupp, S. A. CD19-targeted chimeric antigen receptor T-cell therapy for acute lymphoblastic leukemia. *Blood* 125, 4017-4023 (2015).
6. Sanmamed, M. F. & Chen, L. A Paradigm Shift in Cancer Immunotherapy: From Enhancement to Normalization. *Cell* 175, 313-326 (2018).
7. Kershaw, M. H., Westwood, J. A. & Darcy, P. K. Gene-engineered T cells for cancer therapy. *Nat Rev Cancer* 13, 525-541 (2013).
8. Yao, X., et al. Levels of peripheral CD4(+)FoxP3(+) regulatory T cells are negatively associated with clinical response to adoptive immunotherapy of human cancer. *Blood* 119, 5688-5696 (2012).
9. Hurton, L. V., et al. Tethered IL-15 augments antitumor activity and promotes a stem-cell memory subset in tumor-specific T cells. *Proceedings of the National Academy of Sciences of the United States of America* 113, E7788-E7797 (2016).
10. Hoyos, V., et al. Engineering CD19-specific T lymphocytes with interleukin-15 and a suicide gene to enhance their anti-lymphoma/leukemia effects and safety. *Leukemia* 24, 1160-1170 (2010).
11. Waldmann, T. A., et al. Safety (toxicity), pharmacokinetics, immunogenicity, and impact on elements of the normal immune system of recombinant human IL-15 in rhesus macaques. *Blood* 117, 4787-4795 (2011).
12. Berger, C., et al. Safety and immunologic effects of IL-15 administration in nonhuman primates. *Blood* 114, 2417-2426 (2009).

13. Di Stasi, A., et al. Inducible apoptosis as a safety switch for adoptive cell therapy. *N Engl J Med* 365, 1673-1683 (2011).
14. Kagoya, Y., et al. A novel chimeric antigen receptor containing a JAK-STAT signaling domain mediates superior antitumor effects. *Nat Med* 24, 352-359 (2018).
15. Fraietta, J. A., et al. Determinants of response and resistance to CD19 chimeric antigen receptor (CAR) T cell therapy of chronic lymphocytic leukemia. *Nat Med* 24,
16. Oppmann, B., et al. Novel p19 protein engages IL-12p40 to form a cytokine, IL-23, with biological activities similar as well as distinct from IL-12. *Immunity* 13, 715-725 (2000).
17. Duvallet, E., Semerano, L., Assier, E., Falgarone, G. & Boissier, M. C. Interleukin-23: a key cytokine in inflammatory diseases. *Annals of medicine* 43, 503-511 (2011).
18. Ngiow, S. F., Teng, M. W. & Smyth, M. J. A balance of interleukin-12 and -23 in cancer. *Trends in immunology* 34, 548-555 (2013).
19. Iwakura, Y. & Ishigame, H. The IL-23/IL-17 axis in inflammation. *The Journal of clinical investigation* 116, 1218-1222 (2006).
20. Aggarwal, S., Ghilardi, N., Xie, M. H., de Sauvage, F. J. & Gurney, A. L. Interleukin-23 promotes a distinct CD4 T cell activation state characterized by the production of interleukin-17. *J Biol Chem* 278, 1910-1914 (2003).
21. Xu, Y., et al. Glycolysis determines dichotomous regulation of T cell subsets in hypoxia. *The Journal of clinical investigation* 126, 2678-2688 (2016).
22. Langrish, C. L., et al. IL-23 drives a pathogenic T cell population that induces autoimmune inflammation. *J Exp Med* 201, 233-240 (2005).
23. Zhu, J., Yamane, H. & Paul, W. E. Differentiation of effector CD4 T cell populations (*). *Annu Rev Immunol* 28, 445-489 (2010).
24. Langowski, J. L., et al. IL-23 promotes tumour incidence and growth. *Nature* 442, 461-465 (2006).
25. Grivennikov, S. I., et al. Adenoma-linked barrier defects and microbial products drive IL-23/IL-17-mediated tumour growth. *Nature* 491, 254-258 (2012).
26. Gargett, T., et al. GD2-specific CAR T Cells Undergo Potent Activation and Deletion Following Antigen Encounter but can be Protected From Activation-induced Cell Death by PD-1 Blockade. *Mol Ther* 24, 1135-1149 (2016).
27. Philip, M., et al. Chromatin states define tumour-specific T cell dysfunction and reprogramming. *Nature* 545, 452-456 (2017).
28. Wherry, E. J. T cell exhaustion. *Nat Immunol* 12, 492-499 (2011).
29. Du, H. H., K; Ahn, S; Kren, N. P.; Montgomery, S. A.; Wang, X H; Tiruthani, K; Mirlekar, R; Michaud, D; Greene, K; Herrera, S. G.; Sun, C; Chen, Y H; Xu Y; Ma, X C; Ferrone, C. R.; Pylayeva-Gupta, Y; and Yeh, J. J.; Liu, R H; Savoldo, B; Ferrone, S; Dotti, G. Antitumor Responses in the Absence of Toxicity in Solid Tumors by Targeting B7-H3 Via Chimeric Antigen Receptor T Cells *Cancer Cell* (2018).
30. Diaconu, I., et al. Inducible Caspase-9 Selectively Modulates the Toxicities of CD19-Specific Chimeric Antigen Receptor-Modified T Cells. *Mol Ther* 25, 580-592 (2017).
31. Tey, S. K., Dotti, G., Rooney, C. M., Heslop, H. E. & Brenner, M. K. Inducible caspase 9 suicide gene to improve the safety of allodepleted T cells after haploidentical stem cell transplantation. *Biol Blood Marrow Transplant* 13, 913-924 (2007).
32. Teng, M. W., et al. Opposing roles for IL-23 and IL-12 in maintaining occult cancer in an equilibrium state. *Cancer Res* 72, 3987-3996 (2012).
33. Zhang, L., et al. IL-23 selectively promotes the metastasis of colorectal carcinoma cells with impaired Socs3 expression via the STATS pathway. *Carcinogenesis* 35, 1330-1340 (2014).
34. Lo, C. H., et al. Antitumor and antimetastatic activity of IL-23. *Journal of immunology* 171, 600-607 (2003).
35. Overwijk, W. W., et al. Immunological and antitumor effects of IL-23 as a cancer vaccine adjuvant. *Journal of immunology* 176, 5213-5222 (2006).
36. Floss, D. M., Schroder, J., Franke, M. & Scheller, J. Insights into IL-23 biology: From structure to function. *Cytokine Growth Factor Rev* 26, 569-578 (2015).
37. Hor, Y. T., et al. A role for RUNX3 in inflammation-induced expression of IL23A in gastric epithelial cells. *Cell Rep* 8, 50-58 (2014).
38. Pulliam, S. R., Uzhachenko, R. V., Adunyah, S. E. & Shanker, A. Common gamma chain cytokines in combinatorial immune strategies against cancer. *Immunol Lett* 169, 61-72 (2016).
39. Rochman, Y., Spolski, R. & Leonard, W. J. New insights into the regulation of T cells by gamma(c) family cytokines. *Nat Rev Immunol* 9, 480-490 (2009).
40. Thurley, K., Gerecht, D., Friedmann, E. & Hofer, T. Three-Dimensional Gradients of Cytokine Signaling between T Cells. *PLoS Comput Biol* 11, e1004206
41. Oyler-Yaniv, A., et al. A Tunable Diffusion-Consumption Mechanism of Cytokine Propagation Enables Plasticity in Cell-to-Cell Communication in the Immune System. *Immunity* 46, 609-620 (2017).
42. Noman, M. Z., et al. The cooperative induction of hypoxia-inducible factor-1 alpha and STAT3 during hypoxia induced an impairment of tumor susceptibility to CTL-mediated cell lysis. *Journal of immunology* 182, 3510-3521 (2009).
43. Pawlus, M. R., Wang, L. & Hu, C. J. STAT3 and HIFlalpha cooperatively activate HIF1 target genes in MDA-MB-231 and RCC4 cells. Oncogene 33, 1670-1679 (2014).
44. Song, L., et al. Oncogene MYCN regulates localization of NKT cells to the site of disease in neuroblastoma. *The Journal of clinical investigation* 117, 2702-2712 (2007).
45. Tarek, N., et al. Unlicensed NK cells target neuroblastoma following anti-GD2 antibody treatment. *The Journal of clinical investigation* 122, 3260-3270 (2012).
46. Caruana, I., et al. Heparanase promotes tumor infiltration and antitumor activity of CAR-redirected T lymphocytes. *Nat Med* 21, 524-529 (2015).
47. Louis, C. U., et al. Antitumor activity and long-term fate of chimeric antigen receptor-positive T cells in patients with neuroblastoma. *Blood* 118, 6050-6056 (2011).
48. Vera, J., et al. T lymphocytes redirected against the kappa light chain of human immunoglobulin efficiently kill mature B lymphocyte-derived malignant cells. *Blood* 108, 3890-3897 (2006).
49. Xu, Y., et al. Closely related T-memory stem cells correlate with in vivo expansion of CAR.CD19-T cells and are preserved by IL-7 and IL-15. *Blood* 123, 3750-3759 (2014).
50. Dobin, A., et al. STAR: ultrafast universal RNA-seq aligner. *Bioinformatics* 29, 15-21 (2013).

51. Patro, R., Duggal, G., Love, M. I., Irizarry, R. A. & Kingsford, C. Salmon provides fast and bias-aware quantification of transcript expression. *Nat Methods* 14, 417-419 (2017).

52. Love, M. I., Huber, W. & Anders, S. Moderated estimation of fold change and dispersion for RNA-seq data with DESeq2. *Genome Biol* 15, 550 (2014).

53. Dauer, D. J., et al. Stat3 regulates genes common to both wound healing and cancer. *Oncogene* 24, 3397-3408 (2005).

54. Sockolosky, J. T., et al. Selective targeting of engineered T cells using orthogonal IL-2 cytokine-receptor complexes. *Science* 359, 1037-1042 (2018).

What is claimed is:

1. A modified chimeric antigen receptor (CAR) T cell comprising a cytokine, wherein the cytokine consists of an IL-12β p40 subunit , wherein the T cell, upon activation, produces IL-23.

2. The modified CAR T cell of claim 1, wherein the T cell exhibits one or more of increased cell division, reduced apoptosis, increased T cell proliferation, and increased anti-tumor activity.

3. The modified CAR T cell of claim 1, wherein the T cell, upon activation, exhibits one or more of increased STAT3 phosphorylation, differentiation expression of one or more STAT3 regulated genes selected from the group consisting of: SOX2, SOCS3, CEBPD, ABCA1, IFIT1, IFIT3, USP18, CDKN2B, and combinations thereof, and activation of the STAT3 pathway.

4. The modified CAR T cell of claim 1, wherein the T cell expresses high levels of lytic enzyme granzyme B, as compared to a control cell.

5. The modified CAR T cell of claim 1, wherein the T cell expresses reduced levels of exhaustion markers PD1 and/or CD101, as compared to a control cell.

6. The modified CAR T cell of claim 1, wherein the T cell maintains production of IFNγ and TNFα, as compared to a control cell.

7. The modified CAR T cell of claim 1, wherein the T cell promotes enhanced tumor control and improved survival, as compared to a control cell.

8. The modified CAR T cell of claim 1, wherein the T cell is a human T cell.

9. The modified CAR T cell of claim 1, wherein the cytokine is produced by transducing a T cell with a retroviral supernatant comprising an IL-12β p40 subunit of IL-12 or IL-23.

10. A method of increasing CAR T cell proliferation comprising modifying a T cell to comprise a cytokine, wherein the cytokine consists of an IL12β p40 subunit.

11. A method of treating cancer comprising administering to a subject a modified CAR T cell comprising a cytokine, wherein the cytokine consists of an IL-12β p40 subunit.

12. The method of claim 11, wherein upon activation of the modified T cell, the modified T cell produces IL-23.

13. The method of claim 11, wherein the modified T cell exhibits increased anti-tumor activity and/or increased T cell proliferation.

14. The method of claim 11, wherein the modified T cell promotes tumor regression.

15. The method of claim 11, wherein the modified T cell protects from tumor re-challenge.

16. The method of claim 11, wherein the cancer is selected from the group consisting of a melanoma, a pancreatic cancer, a hematologic malignancy, a multiple myeloma, a carcinoma, and a sarcoma.

17. The method of claim 11, wherein the subject is a mammal.

* * * * *

SEQUENCE LISTING

```
<160> NUMBER OF SEQ ID NOS: 34

<210> SEQ ID NO 1
<211> LENGTH: 18
<212> TYPE: DNA
<213> ORGANISM: Artificial
<220> FEATURE:
<223> OTHER INFORMATION: primer

<400> SEQUENCE: 1

aacccgttga accccatt                                                    18


<210> SEQ ID NO 2
<211> LENGTH: 20
<212> TYPE: DNA
<213> ORGANISM: Artificial
<220> FEATURE:
<223> OTHER INFORMATION: primer

<400> SEQUENCE: 2

ccatccaatc ggtagtagcg                                                  20


<210> SEQ ID NO 3
<211> LENGTH: 20
<212> TYPE: DNA
<213> ORGANISM: Artificial
<220> FEATURE:
<223> OTHER INFORMATION: primer

<400> SEQUENCE: 3

ataataacaa tcatcggcgg                                                  20


<210> SEQ ID NO 4
<211> LENGTH: 20
<212> TYPE: DNA
<213> ORGANISM: Artificial
<220> FEATURE:
<223> OTHER INFORMATION: primer

<400> SEQUENCE: 4

aaaaagagag aggcaaactg                                                  20


<210> SEQ ID NO 5
<211> LENGTH: 20
<212> TYPE: DNA
<213> ORGANISM: Artificial
<220> FEATURE:
<223> OTHER INFORMATION: primer

<400> SEQUENCE: 5

cctattacat ctactccggg                                                  20


<210> SEQ ID NO 6
<211> LENGTH: 20
<212> TYPE: DNA
<213> ORGANISM: Artificial
<220> FEATURE:
<223> OTHER INFORMATION: primer
```

<400> SEQUENCE: 6
actttctcat aggagtccag 20

<210> SEQ ID NO 7
<211> LENGTH: 20
<212> TYPE: DNA
<213> ORGANISM: Artificial
<220> FEATURE:
<223> OTHER INFORMATION: primer

<400> SEQUENCE: 7
cagacttttc agacaaaccc 20

<210> SEQ ID NO 8
<211> LENGTH: 19
<212> TYPE: DNA
<213> ORGANISM: Artificial
<220> FEATURE:
<223> OTHER INFORMATION: primer

<400> SEQUENCE: 8
tttcgatttc aaatgctgc 19

<210> SEQ ID NO 9
<211> LENGTH: 18
<212> TYPE: DNA
<213> ORGANISM: Artificial
<220> FEATURE:
<223> OTHER INFORMATION: primer

<400> SEQUENCE: 9
gtgtttctgg atgaaccc 18

<210> SEQ ID NO 10
<211> LENGTH: 19
<212> TYPE: DNA
<213> ORGANISM: Artificial
<220> FEATURE:
<223> OTHER INFORMATION: primer

<400> SEQUENCE: 10
ttccattgac catgattgc 19

<210> SEQ ID NO 11
<211> LENGTH: 20
<212> TYPE: DNA
<213> ORGANISM: Artificial
<220> FEATURE:
<223> OTHER INFORMATION: primer

<400> SEQUENCE: 11
ctgcctaatt tacagcaacc 20

<210> SEQ ID NO 12
<211> LENGTH: 20
<212> TYPE: DNA
<213> ORGANISM: Artificial
<220> FEATURE:
<223> OTHER INFORMATION: primer

<400> SEQUENCE: 12
tgatccaaga ctctgttttc 20

<210> SEQ ID NO 13
<211> LENGTH: 18

<212> TYPE: DNA
<213> ORGANISM: Artificial
<220> FEATURE:
<223> OTHER INFORMATION: primer

<400> SEQUENCE: 13
atgagtgagg tcaccaag 18

<210> SEQ ID NO 14
<211> LENGTH: 17
<212> TYPE: DNA
<213> ORGANISM: Artificial
<220> FEATURE:
<223> OTHER INFORMATION: primer

<400> SEQUENCE: 14
ccttgaagtt ccaggtg 17

<210> SEQ ID NO 15
<211> LENGTH: 20
<212> TYPE: DNA
<213> ORGANISM: Artificial
<220> FEATURE:
<223> OTHER INFORMATION: primer

<400> SEQUENCE: 15
tggtttacac aacattggac 20

<210> SEQ ID NO 16
<211> LENGTH: 21
<212> TYPE: DNA
<213> ORGANISM: Artificial
<220> FEATURE:
<223> OTHER INFORMATION: primer

<400> SEQUENCE: 16
atcctcttca atatcctggt g 21

<210> SEQ ID NO 17
<211> LENGTH: 18
<212> TYPE: DNA
<213> ORGANISM: Artificial
<220> FEATURE:
<223> OTHER INFORMATION: primer

<400> SEQUENCE: 17
gactagtgga gaaggtgc 18

<210> SEQ ID NO 18
<211> LENGTH: 18
<212> TYPE: DNA
<213> ORGANISM: Artificial
<220> FEATURE:
<223> OTHER INFORMATION: primer

<400> SEQUENCE: 18
tcatcatgac ctggatcg 18

<210> SEQ ID NO 19
<211> LENGTH: 20
<212> TYPE: DNA
<213> ORGANISM: Artificial
<220> FEATURE:
<223> OTHER INFORMATION: primer

<400> SEQUENCE: 19
aaaatctcat ccaagaagcc 20

<210> SEQ ID NO 20
<211> LENGTH: 20
<212> TYPE: DNA
<213> ORGANISM: Artificial
<220> FEATURE:
<223> OTHER INFORMATION: primer

<400> SEQUENCE: 20
aatgttccaa ttcctactgc 20

<210> SEQ ID NO 21
<211> LENGTH: 21
<212> TYPE: DNA
<213> ORGANISM: Artificial
<220> FEATURE:
<223> OTHER INFORMATION: primer

<400> SEQUENCE: 21
cagaatcaca gaactgattg g 21

<210> SEQ ID NO 22
<211> LENGTH: 20
<212> TYPE: DNA
<213> ORGANISM: Artificial
<220> FEATURE:
<223> OTHER INFORMATION: primer

<400> SEQUENCE: 22
tgactcttgg tcatgttctc 20

<210> SEQ ID NO 23
<211> LENGTH: 20
<212> TYPE: DNA
<213> ORGANISM: Artificial
<220> FEATURE:
<223> OTHER INFORMATION: primer

<400> SEQUENCE: 23
aggcatctat attggaaagc 20

<210> SEQ ID NO 24
<211> LENGTH: 20
<212> TYPE: DNA
<213> ORGANISM: Artificial
<220> FEATURE:
<223> OTHER INFORMATION: primer

<400> SEQUENCE: 24
gcttacaatg gtctcaagtt 20

<210> SEQ ID NO 25
<211> LENGTH: 20
<212> TYPE: DNA
<213> ORGANISM: Artificial
<220> FEATURE:
<223> OTHER INFORMATION: primer

<400> SEQUENCE: 25
atgatgtcat tcccacaatg 20

<210> SEQ ID NO 26
<211> LENGTH: 20
<212> TYPE: DNA
<213> ORGANISM: Artificial

<220> FEATURE:
<223> OTHER INFORMATION: primer

<400> SEQUENCE: 26
aagagtgctg attgagtaac 20

<210> SEQ ID NO 27
<211> LENGTH: 20
<212> TYPE: DNA
<213> ORGANISM: Artificial
<220> FEATURE:
<223> OTHER INFORMATION: primer

<400> SEQUENCE: 27
cttttccaga ctgatccaac 20

<210> SEQ ID NO 28
<211> LENGTH: 22
<212> TYPE: DNA
<213> ORGANISM: Artificial
<220> FEATURE:
<223> OTHER INFORMATION: primer

<400> SEQUENCE: 28
gattcttcct cttcatttcc ag 22

<210> SEQ ID NO 29
<211> LENGTH: 20
<212> TYPE: DNA
<213> ORGANISM: Artificial
<220> FEATURE:
<223> OTHER INFORMATION: primer

<400> SEQUENCE: 29
aatgtaagag taggaagggg 20

<210> SEQ ID NO 30
<211> LENGTH: 20
<212> TYPE: DNA
<213> ORGANISM: Artificial
<220> FEATURE:
<223> OTHER INFORMATION: primer

<400> SEQUENCE: 30
acagttctag atggaagacc 20

<210> SEQ ID NO 31
<211> LENGTH: 21
<212> TYPE: DNA
<213> ORGANISM: Artificial
<220> FEATURE:
<223> OTHER INFORMATION: primer

<400> SEQUENCE: 31
cccaaatttg atagactgct g 21

<210> SEQ ID NO 32
<211> LENGTH: 20
<212> TYPE: DNA
<213> ORGANISM: Artificial
<220> FEATURE:
<223> OTHER INFORMATION: primer

<400> SEQUENCE: 32
acaccttttt cacctgttag 20

-continued

```
<210> SEQ ID NO 33
<211> LENGTH: 20
<212> TYPE: DNA
<213> ORGANISM: Artificial
<220> FEATURE:
<223> OTHER INFORMATION: primer

<400> SEQUENCE: 33

atcattcata gcagatgtgg                                                20


<210> SEQ ID NO 34
<211> LENGTH: 20
<212> TYPE: DNA
<213> ORGANISM: Artificial
<220> FEATURE:
<223> OTHER INFORMATION: primer

<400> SEQUENCE: 34

atatctggtt gcgtaagagg                                                20
```